(12) United States Patent
Sun et al.

(10) Patent No.: US 8,801,626 B2
(45) Date of Patent: *Aug. 12, 2014

(54) FLEXIBLE NEURAL LOCALIZATION DEVICES AND METHODS

(75) Inventors: Benjamin Kao-Shing Sun, San Francisco, CA (US); Michael P. Wallace, Pleasanton, CA (US); Christopher D. Summa, Santa Cruz, CA (US); Jeffery L. Bleich, Palo Alto, CA (US)

(73) Assignee: Baxano Surgical, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/340,363

(22) Filed: Dec. 29, 2011

(65) Prior Publication Data

US 2012/0123294 A1 May 17, 2012

Related U.S. Application Data

(60) Continuation-in-part of application No. 12/724,315, filed on Mar. 15, 2010, which is a continuation-in-part
(Continued)

(51) Int. Cl.
*A61B 5/05* (2006.01)
*A61N 1/00* (2006.01)

(52) U.S. Cl.
USPC .......................................... 600/554; 607/117

(58) Field of Classification Search
USPC .................. 600/544–547, 554; 607/115–118
See application file for complete search history.

(56) References Cited

U.S. PATENT DOCUMENTS

| 184,804 A | 11/1876 | Stohlmann |
|---|---|---|
| 289,104 A | 11/1883 | How |

(Continued)

FOREIGN PATENT DOCUMENTS

| CN | 1338911 A | 3/2002 |
|---|---|---|
| CN | 101291633 A | 10/2008 |

(Continued)

OTHER PUBLICATIONS

Bleich et al.; U.S. Appl. No. 13/484,744 entitled "Devices and Methods for Tissue Modification," filed May 31, 2012.

(Continued)

*Primary Examiner* — Max Hindenburg
*Assistant Examiner* — John Pani
(74) *Attorney, Agent, or Firm* — Shay Glenn LLP

(57) ABSTRACT

Methods for determining if a nerve is nearby a device. The neural stimulation tools described herein are configured to be flexible and low-profile, so that they can be used within body regions that may be tortuous or difficult to reach, such as within a compressed or partially occluded neural foramen. In most cases, these tools described herein are ribbon-shaped and adapted to be manipulated bimanually, applying force to the ends of the devices from separate locations outside of the patient's body. Thus, the distal end region of the device may be configured to couple to the proximal end of a guidewire. One or more surfaces of the devices may include an electrode or multi-polar network of electrodes configured to stimulate only nerves within a predetermined distance of a particular face of the device. Methods of using these devices are described.

12 Claims, 38 Drawing Sheets

Related U.S. Application Data of application No. 12/504,545, filed on Jul. 16, 2009, now Pat. No. 8,419,653, which is a division of application No. 11/457,416, filed on Jul. 13, 2006, now Pat. No. 7,578,819, which is a continuation-in-part of application No. 11/251,205, filed on Oct. 15, 2005, now Pat. No. 7,918,849, said application No. 12/724,315 is a continuation-in-part of application No. 11/251,205, filed on Oct. 15, 2005, now Pat. No. 7,918,849.

(60) Provisional application No. 61/160,164, filed on Mar. 13, 2009, provisional application No. 61/220,314, filed on Jun. 25, 2009, provisional application No. 61/254,406, filed on Oct. 23, 2009, provisional application No. 61/292,840, filed on Jan. 6, 2010, provisional application No. 61/299,303, filed on Jan. 28, 2010, provisional application No. 61/301,568, filed on Feb. 4, 2010.

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,590,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,176 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |

(56) References Cited

U.S. PATENT DOCUMENTS

| | | | |
|---|---|---|---|
| 5,421,348 A | 6/1995 | Larnard | |
| 5,423,331 A | 6/1995 | Wysham | |
| 5,437,661 A | 8/1995 | Rieser | |
| 5,439,464 A | 8/1995 | Shapiro | |
| 5,441,044 A | 8/1995 | Tovey et al. | |
| 5,441,510 A | 8/1995 | Simpson et al. | |
| 5,454,815 A | 10/1995 | Geisser et al. | |
| 5,456,254 A | 10/1995 | Pietroski et al. | |
| 5,496,325 A | 3/1996 | McLees | |
| 5,512,037 A | 4/1996 | Russell et al. | |
| 5,515,848 A | 5/1996 | Corbett, III et al. | |
| 5,531,749 A | 7/1996 | Michelson | |
| 5,534,009 A | 7/1996 | Lander | |
| 5,546,958 A | 8/1996 | Thorud et al. | |
| 5,554,110 A | 9/1996 | Edwards et al. | |
| 5,555,892 A | 9/1996 | Tipton | |
| 5,560,372 A | 10/1996 | Cory | |
| 5,562,695 A | 10/1996 | Obenchain | |
| 5,571,181 A | 11/1996 | Li | |
| 5,582,618 A | 12/1996 | Chin et al. | |
| 5,591,170 A | 1/1997 | Spievack et al. | |
| 5,598,848 A | 2/1997 | Swanson et al. | |
| 5,620,447 A | 4/1997 | Smith et al. | |
| 5,630,426 A | 5/1997 | Eggers et al. | |
| 5,634,475 A | 6/1997 | Wolvek | |
| 5,643,304 A | 7/1997 | Schechter et al. | |
| 5,651,373 A | 7/1997 | Mah | |
| 5,656,012 A | 8/1997 | Sienkiewicz | |
| 5,680,860 A | 10/1997 | Imran | |
| 5,681,324 A | 10/1997 | Kammerer et al. | |
| 5,697,889 A | 12/1997 | Slotman et al. | |
| 5,709,697 A | 1/1998 | Ratcliff et al. | |
| 5,725,530 A | 3/1998 | Popken | |
| 5,735,792 A | 4/1998 | Vanden Hoek et al. | |
| 5,755,732 A | 5/1998 | Green et al. | |
| 5,759,159 A | 6/1998 | Masreliez | |
| 5,762,629 A | 6/1998 | Kambin | |
| 5,766,168 A | 6/1998 | Mantell | |
| 5,769,865 A | 6/1998 | Kermode et al. | |
| 5,775,331 A * | 7/1998 | Raymond et al. | 600/554 |
| 5,779,642 A | 7/1998 | Nightengale | |
| 5,788,653 A | 8/1998 | Lorenzo | |
| 5,792,044 A | 8/1998 | Foley et al. | |
| 5,795,308 A | 8/1998 | Russin | |
| 5,800,350 A | 9/1998 | Coppleson et al. | |
| 5,803,902 A | 9/1998 | Sienkiewicz et al. | |
| 5,803,904 A | 9/1998 | Mehdizadeh | |
| 5,807,263 A | 9/1998 | Chance | |
| 5,810,744 A | 9/1998 | Chu et al. | |
| 5,813,405 A | 9/1998 | Montano, Jr. et al. | |
| 5,824,040 A | 10/1998 | Cox et al. | |
| 5,830,151 A | 11/1998 | Hadzic et al. | |
| 5,830,157 A | 11/1998 | Foote | |
| 5,830,188 A | 11/1998 | Abouleish | |
| 5,833,692 A | 11/1998 | Cesarini et al. | |
| 5,836,810 A | 11/1998 | Asum | |
| 5,836,948 A | 11/1998 | Zucherman et al. | |
| 5,843,110 A | 12/1998 | Dross et al. | |
| 5,846,196 A | 12/1998 | Siekmeyer et al. | |
| 5,846,244 A | 12/1998 | Cripe | |
| 5,851,191 A | 12/1998 | Gozani | |
| 5,851,209 A | 12/1998 | Kummer et al. | |
| 5,851,214 A | 12/1998 | Larsen et al. | |
| 5,853,373 A | 12/1998 | Griffith et al. | |
| 5,865,844 A | 2/1999 | Plaia et al. | |
| 5,868,767 A | 2/1999 | Farley et al. | |
| 5,879,353 A | 3/1999 | Terry | |
| 5,885,219 A | 3/1999 | Nightengale | |
| 5,895,417 A | 4/1999 | Pomeranz et al. | |
| 5,897,583 A | 4/1999 | Meyer et al. | |
| 5,899,909 A | 5/1999 | Claren et al. | |
| 5,904,657 A | 5/1999 | Unsworth et al. | |
| 5,916,173 A | 6/1999 | Kirsner | |
| 5,918,604 A | 7/1999 | Whelan | |
| 5,919,190 A | 7/1999 | VanDusseldorp | |
| 5,928,158 A | 7/1999 | Aristides | |
| 5,928,159 A | 7/1999 | Eggers et al. | |
| 5,941,822 A | 8/1999 | Skladnev et al. | |
| 5,961,522 A | 10/1999 | Mehdizadeh | |
| 5,972,013 A | 10/1999 | Schmidt | |
| 5,976,110 A | 11/1999 | Greengrass et al. | |
| 5,976,146 A | 11/1999 | Ogawa et al. | |
| 6,002,964 A | 12/1999 | Feler et al. | |
| 6,004,326 A | 12/1999 | Castro et al. | |
| 6,004,330 A | 12/1999 | Middleman et al. | |
| 6,010,493 A | 1/2000 | Snoke | |
| 6,015,406 A | 1/2000 | Goble et al. | |
| 6,022,362 A | 2/2000 | Lee et al. | |
| 6,030,383 A | 2/2000 | Benderev | |
| 6,030,401 A | 2/2000 | Marino | |
| 6,038,480 A | 3/2000 | Hrdlicka et al. | |
| 6,048,345 A | 4/2000 | Berke et al. | |
| 6,068,642 A | 5/2000 | Johnson et al. | |
| 6,073,051 A | 6/2000 | Sharkey et al. | |
| 6,099,514 A | 8/2000 | Sharkey et al. | |
| 6,102,930 A | 8/2000 | Simmons, Jr. | |
| 6,106,558 A | 8/2000 | Picha | |
| 6,113,534 A | 9/2000 | Koros et al. | |
| D432,384 S | 10/2000 | Simons | |
| 6,132,387 A | 10/2000 | Gozani et al. | |
| 6,136,014 A | 10/2000 | Sirimanne et al. | |
| 6,142,993 A | 11/2000 | Whayne et al. | |
| 6,142,994 A | 11/2000 | Swanson et al. | |
| 6,146,380 A | 11/2000 | Racz et al. | |
| 6,152,894 A | 11/2000 | Kubler | |
| 6,169,916 B1 | 1/2001 | West | |
| 6,205,360 B1 | 3/2001 | Carter | |
| 6,214,001 B1 | 4/2001 | Casscells et al. | |
| 6,214,016 B1 | 4/2001 | Williams et al. | |
| 6,236,892 B1 | 5/2001 | Feler | |
| 6,251,115 B1 | 6/2001 | Williams et al. | |
| 6,256,540 B1 | 7/2001 | Panescu et al. | |
| 6,259,945 B1 | 7/2001 | Epstein et al. | |
| 6,261,582 B1 | 7/2001 | Needham et al. | |
| 6,266,551 B1 | 7/2001 | Osadchy et al. | |
| 6,266,558 B1 | 7/2001 | Gozani et al. | |
| 6,267,760 B1 | 7/2001 | Swanson | |
| 6,272,367 B1 | 8/2001 | Chance | |
| 6,277,094 B1 | 8/2001 | Schendel | |
| 6,280,447 B1 | 8/2001 | Marino et al. | |
| 6,292,702 B1 | 9/2001 | King et al. | |
| 6,298,256 B1 | 10/2001 | Meyer | |
| 6,312,392 B1 | 11/2001 | Herzon | |
| 6,324,418 B1 | 11/2001 | Crowley et al. | |
| 6,324,432 B1 | 11/2001 | Rigaux et al. | |
| 6,325,764 B1 * | 12/2001 | Griffith et al. | 600/554 |
| 6,334,068 B1 | 12/2001 | Hacker | |
| 6,343,226 B1 | 1/2002 | Sunde et al. | |
| 6,358,254 B1 | 3/2002 | Anderson | |
| 6,360,750 B1 | 3/2002 | Gerber et al. | |
| 6,364,886 B1 | 4/2002 | Sklar | |
| 6,368,324 B1 | 4/2002 | Dinger et al. | |
| 6,370,411 B1 | 4/2002 | Osadchy et al. | |
| 6,370,435 B2 | 4/2002 | Panescu et al. | |
| 6,383,509 B1 | 5/2002 | Donovan et al. | |
| 6,390,906 B1 | 5/2002 | Subramanian | |
| 6,391,028 B1 | 5/2002 | Fanton et al. | |
| 6,416,505 B1 | 7/2002 | Fleischman et al. | |
| 6,423,071 B1 | 7/2002 | Lawson | |
| 6,423,080 B1 | 7/2002 | Gellman et al. | |
| 6,425,859 B1 | 7/2002 | Foley et al. | |
| 6,425,887 B1 | 7/2002 | McGuckin et al. | |
| 6,428,486 B2 | 8/2002 | Ritchart et al. | |
| 6,436,101 B1 | 8/2002 | Hamada | |
| 6,442,848 B1 | 9/2002 | Dean | |
| 6,446,621 B1 | 9/2002 | Svensson | |
| 6,451,335 B1 | 9/2002 | Goldenheim et al. | |
| 6,454,767 B2 | 9/2002 | Alleyne | |
| 6,464,682 B1 | 10/2002 | Snoke | |
| 6,466,817 B1 | 10/2002 | Kaula et al. | |
| 6,468,289 B1 | 10/2002 | Bonutti | |
| 6,470,209 B2 | 10/2002 | Snoke | |
| 6,478,805 B1 | 11/2002 | Marino et al. | |
| 6,487,439 B1 | 11/2002 | Skladnev et al. | |

(56) References Cited

U.S. PATENT DOCUMENTS

| | | | |
|---|---|---|---|
| 6,488,636 | B2 | 12/2002 | Bryan et al. |
| 6,491,646 | B1 | 12/2002 | Blackledge |
| 6,500,128 | B2 | 12/2002 | Marino |
| 6,500,189 | B1 | 12/2002 | Lang et al. |
| 6,512,958 | B1 | 1/2003 | Swoyer et al. |
| 6,516,223 | B2 | 2/2003 | Hofmann |
| 6,520,907 | B1 | 2/2003 | Foley et al. |
| 6,527,786 | B1 | 3/2003 | Davis et al. |
| 6,533,749 | B1 | 3/2003 | Mitusina et al. |
| 6,535,759 | B1 | 3/2003 | Epstein et al. |
| 6,540,742 | B1 | 4/2003 | Thomas et al. |
| 6,540,761 | B2 | 4/2003 | Houser |
| 6,546,270 | B1 | 4/2003 | Goldin et al. |
| 6,558,353 | B2 | 5/2003 | Zohmann |
| 6,558,390 | B2 | 5/2003 | Cragg |
| 6,562,033 | B2 | 5/2003 | Shah et al. |
| 6,564,078 | B1 | 5/2003 | Marino et al. |
| 6,564,079 | B1 | 5/2003 | Cory et al. |
| 6,564,088 | B1 | 5/2003 | Soller et al. |
| 6,569,160 | B1 | 5/2003 | Goldin et al. |
| 6,575,979 | B1 | 6/2003 | Cragg |
| 6,579,291 | B1 | 6/2003 | Keith et al. |
| 6,584,345 | B2 | 6/2003 | Govari |
| 6,592,559 | B1 | 7/2003 | Pakter et al. |
| 6,595,932 | B2 | 7/2003 | Ferrera |
| 6,597,955 | B2 | 7/2003 | Panescu et al. |
| 6,606,523 | B1 | 8/2003 | Jenkins |
| 6,607,530 | B1 | 8/2003 | Carl et al. |
| 6,609,018 | B2 | 8/2003 | Cory et al. |
| 6,610,066 | B2 | 8/2003 | Dinger et al. |
| 6,620,129 | B2 | 9/2003 | Stecker et al. |
| 6,622,731 | B2 | 9/2003 | Daniel et al. |
| 6,624,510 | B1 | 9/2003 | Chan et al. |
| 6,626,916 | B1 | 9/2003 | Yeung et al. |
| 6,632,184 | B1 | 10/2003 | Truwit |
| 6,638,233 | B2 | 10/2003 | Corvi et al. |
| RE38,335 | E | 11/2003 | Aust et al. |
| 6,648,883 | B2 | 11/2003 | Francischelli et al. |
| 6,666,874 | B2 | 12/2003 | Heitzmann et al. |
| 6,673,063 | B2 | 1/2004 | Brett |
| 6,673,068 | B1 | 1/2004 | Berube |
| 6,678,552 | B2 | 1/2004 | Pearlman |
| 6,682,535 | B2 | 1/2004 | Hoogland |
| 6,682,536 | B2 | 1/2004 | Vardi et al. |
| 6,685,709 | B2 | 2/2004 | Sklar |
| 6,699,246 | B2 | 3/2004 | Zucherman et al. |
| 6,723,049 | B2 | 4/2004 | Skladnev et al. |
| 6,726,531 | B1 | 4/2004 | Harrel |
| 6,726,685 | B2 | 4/2004 | To et al. |
| 6,733,496 | B2 | 5/2004 | Sharkey et al. |
| 6,736,815 | B2 | 5/2004 | Ginn |
| 6,736,835 | B2 | 5/2004 | Pellegrino et al. |
| 6,746,451 | B2 | 6/2004 | Middleton et al. |
| 6,752,814 | B2 | 6/2004 | Gellman et al. |
| 6,760,616 | B2 | 7/2004 | Hoey et al. |
| 6,764,491 | B2 | 7/2004 | Frey et al. |
| 6,772,012 | B2 | 8/2004 | Ricart et al. |
| 6,776,765 | B2 | 8/2004 | Soukup et al. |
| 6,786,876 | B2 | 9/2004 | Cox |
| 6,788,966 | B2 | 9/2004 | Kenan et al. |
| 6,790,210 | B1 | 9/2004 | Cragg et al. |
| 6,795,737 | B2 | 9/2004 | Gielen et al. |
| 6,805,695 | B2 | 10/2004 | Keith et al. |
| 6,805,697 | B1 | 10/2004 | Helm et al. |
| 6,807,444 | B2 | 10/2004 | Tu et al. |
| 6,830,561 | B2 | 12/2004 | Jansen et al. |
| 6,830,570 | B1 | 12/2004 | Frey et al. |
| 6,832,111 | B2 | 12/2004 | Tu et al. |
| 6,845,264 | B1 | 1/2005 | Skladnev et al. |
| 6,847,849 | B2 | 1/2005 | Mamo et al. |
| 6,851,430 | B2 | 2/2005 | Tsou |
| 6,865,409 | B2 | 3/2005 | Getsla et al. |
| 6,872,204 | B2 | 3/2005 | Houser |
| 6,875,221 | B2 | 4/2005 | Cull |
| 6,882,879 | B2 | 4/2005 | Rock |
| 6,884,220 | B2 | 4/2005 | Aviv et al. |
| 6,890,353 | B2 | 5/2005 | Cohn et al. |
| 6,895,283 | B2 | 5/2005 | Erickson et al. |
| 6,899,716 | B2 | 5/2005 | Cragg |
| 6,907,884 | B2 | 6/2005 | Pellegrino et al. |
| 6,911,003 | B2 | 6/2005 | Anderson et al. |
| 6,911,016 | B2 | 6/2005 | Balzum et al. |
| 6,916,328 | B2 | 7/2005 | Brett |
| 6,923,813 | B2 | 8/2005 | Phillips et al. |
| 6,929,647 | B2 | 8/2005 | Cohen |
| 6,949,104 | B2 | 9/2005 | Griffis et al. |
| 6,953,461 | B2 | 10/2005 | McClurken et al. |
| 6,962,587 | B2 | 11/2005 | Johnson et al. |
| 6,969,392 | B2 | 11/2005 | Gitis et al. |
| 6,971,986 | B2 | 12/2005 | Staskin et al. |
| 6,972,199 | B2 | 12/2005 | Lebouitz et al. |
| 6,973,342 | B1 | 12/2005 | Swanson |
| 6,976,986 | B2 | 12/2005 | Berube |
| 6,991,643 | B2 | 1/2006 | Saadat |
| 6,994,693 | B2 | 2/2006 | Tal |
| 6,997,934 | B2 | 2/2006 | Snow et al. |
| 6,999,820 | B2 | 2/2006 | Jordan |
| 7,001,333 | B2 | 2/2006 | Hamel et al. |
| 7,008,431 | B2 | 3/2006 | Simonson |
| 7,010,352 | B2 | 3/2006 | Hogan |
| 7,011,635 | B1 | 3/2006 | Delay |
| 7,011,663 | B2 | 3/2006 | Michelson |
| 7,014,616 | B2 | 3/2006 | Ferrera |
| 7,033,373 | B2 | 4/2006 | de la Torre et al. |
| 7,041,099 | B2 | 5/2006 | Thomas et al. |
| 7,047,084 | B2 | 5/2006 | Erickson et al. |
| 7,048,682 | B2 | 5/2006 | Neisz et al. |
| 7,050,848 | B2 | 5/2006 | Hoey et al. |
| 7,063,682 | B1 | 6/2006 | Whayne et al. |
| 7,069,083 | B2 | 6/2006 | Finch et al. |
| 7,070,556 | B2 | 7/2006 | Anderson et al. |
| 7,070,596 | B1 | 7/2006 | Woloszko et al. |
| 7,079,883 | B2 | 7/2006 | Marino et al. |
| 7,081,122 | B1 | 7/2006 | Reiley et al. |
| 7,087,053 | B2 | 8/2006 | Vanney |
| 7,087,058 | B2 | 8/2006 | Cragg |
| 7,107,104 | B2 | 9/2006 | Keravel et al. |
| 7,118,576 | B2 | 10/2006 | Gitis et al. |
| 7,141,019 | B2 | 11/2006 | Pearlman |
| 7,166,073 | B2 | 1/2007 | Ritland |
| 7,166,081 | B2 | 1/2007 | McKinley |
| 7,166,107 | B2 | 1/2007 | Anderson |
| 7,169,107 | B2 | 1/2007 | Jersey-Willuhn et al. |
| 7,169,147 | B2 | 1/2007 | Nosel |
| 7,172,562 | B2 | 2/2007 | McKinley |
| 7,177,677 | B2 | 2/2007 | Kaula et al. |
| 7,181,289 | B2 | 2/2007 | Pflueger et al. |
| 7,189,240 | B1 | 3/2007 | Dekel |
| 7,192,430 | B2 | 3/2007 | Truckai et al. |
| 7,198,598 | B2 | 4/2007 | Smith et al. |
| 7,198,626 | B2 | 4/2007 | Lee et al. |
| 7,207,949 | B2 | 4/2007 | Miles et al. |
| 7,211,082 | B2 | 5/2007 | Hall et al. |
| 7,214,186 | B2 | 5/2007 | Ritland |
| 7,214,197 | B2 * | 5/2007 | Prass .......................... 600/554 |
| 7,216,001 | B2 | 5/2007 | Hacker et al. |
| 7,223,278 | B2 | 5/2007 | Davison et al. |
| 7,236,832 | B2 | 6/2007 | Hemmerling et al. |
| 7,238,189 | B2 | 7/2007 | Schmieding et al. |
| 7,239,911 | B2 | 7/2007 | Scholz |
| 7,245,789 | B2 | 7/2007 | Bates et al. |
| 7,270,658 | B2 | 9/2007 | Woloszko et al. |
| 7,270,659 | B2 | 9/2007 | Ricart et al. |
| 7,282,033 | B2 | 10/2007 | Urmey |
| 7,282,061 | B2 | 10/2007 | Sharkey et al. |
| 7,295,881 | B2 | 11/2007 | Cohen et al. |
| 7,318,823 | B2 | 1/2008 | Sharps et al. |
| 7,337,005 | B2 | 2/2008 | Kim et al. |
| 7,337,006 | B2 | 2/2008 | Kim et al. |
| 7,367,972 | B2 | 5/2008 | Francischelli et al. |
| 7,383,639 | B2 | 6/2008 | Malandain |
| 7,390,330 | B2 | 6/2008 | Harp |
| 7,419,487 | B2 | 9/2008 | Johnson et al. |
| 7,449,019 | B2 | 11/2008 | Uchida et al. |

(56) References Cited

U.S. PATENT DOCUMENTS

| | | |
|---|---|---|
| 7,452,351 B2 | 11/2008 | Miller et al. |
| 7,470,236 B1 | 12/2008 | Kelleher et al. |
| 7,476,226 B2 | 1/2009 | Weikel et al. |
| 7,494,473 B2 | 2/2009 | Eggers et al. |
| 7,500,977 B2 | 3/2009 | Assell et al. |
| 7,503,920 B2 | 3/2009 | Siegal |
| 7,507,218 B2 | 3/2009 | Aliski et al. |
| 7,522,953 B2 | 4/2009 | Gharib et al. |
| 7,553,307 B2 | 6/2009 | Bleich et al. |
| 7,555,343 B2 | 6/2009 | Bleich |
| 7,578,819 B2 * | 8/2009 | Bleich et al. ............... 606/53 |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 7,959,577 B2 * | 6/2011 | Schmitz et al. ............... 600/554 |
| 7,963,915 B2 | 6/2011 | Bleich |
| 8,048,080 B2 | 11/2011 | Bleich et al. |
| 8,062,298 B2 | 11/2011 | Schmitz et al. |
| 8,062,300 B2 | 11/2011 | Schmitz et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2002/0022788 A1 | 2/2002 | Corvi et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0074037 A1 | 4/2003 | Moore et al. |
| 2003/0105503 A1 | 6/2003 | Marino |
| 2003/0113906 A1 | 6/2003 | Sangha et al. |
| 2003/0130655 A1 | 7/2003 | Woloszko |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0030330 A1 | 2/2004 | Brassell et al. |
| 2004/0049208 A1 | 3/2004 | Hill et al. |
| 2004/0059260 A1 | 3/2004 | Truwit |
| 2004/0064058 A1 | 4/2004 | McKay |
| 2004/0097927 A1 | 5/2004 | Yeung et al. |
| 2004/0098074 A1 | 5/2004 | Erickson et al. |
| 2004/0106940 A1 | 6/2004 | Shaolian et al. |
| 2004/0111084 A1 | 6/2004 | Brett |
| 2004/0122433 A1 | 6/2004 | Loubens et al. |
| 2004/0122482 A1 | 6/2004 | Tung et al. |
| 2004/0127893 A1 | 7/2004 | Hovda |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0220576 A1 | 11/2004 | Sklar |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0149035 A1 | 7/2005 | Pimenta et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095028 A1 | 5/2006 | Bleich |
| 2006/0095059 A1 | 5/2006 | Bleich et al. |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0258951 A1 * | 11/2006 | Bleich et al. ............... 600/546 |
| 2006/0264952 A1 | 11/2006 | Nelson et al. |
| 2006/0264994 A1 | 11/2006 | Schomer et al. |
| 2006/0271080 A1 | 11/2006 | Suddaby |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |

(56) References Cited

U.S. PATENT DOCUMENTS

| | | |
|---|---|---|
| 2007/0106219 A1 | 5/2007 | Grabinsky |
| 2007/0123766 A1 | 5/2007 | Whalen, III et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213795 A1 | 9/2007 | Bradley et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0293782 A1 | 12/2007 | Marino |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058820 A1 | 3/2008 | Harp |
| 2008/0058874 A1 | 3/2008 | Westlund et al. |
| 2008/0064945 A1 | 3/2008 | Marino et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0036936 A1 | 2/2009 | Solsberg et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0177241 A1 | 7/2009 | Bleich et al. |
| 2009/0182382 A1 | 7/2009 | Justis et al. |
| 2009/0192403 A1 | 7/2009 | Gharib et al. |
| 2009/0204016 A1 | 8/2009 | Gharib et al. |
| 2009/0204119 A1 | 8/2009 | Bleich et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0046613 A1 | 2/2011 | Schmitz et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat |
| 2011/0196257 A1 | 8/2011 | Schmitz et al. |
| 2011/0224709 A1 | 9/2011 | Bleich |
| 2011/0224710 A1 | 9/2011 | Bleich |
| 2012/0016368 A1 | 1/2012 | Bleich et al. |
| 2012/0078255 A1 | 3/2012 | Bleich et al. |
| 2012/0184809 A1 | 7/2012 | Bleich et al. |
| 2012/0191003 A1 | 7/2012 | Garabedian et al. |
| 2013/0012831 A1 | 1/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |
| 2014/0012239 A1 | 1/2014 | Schmitz et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO97/14362 A1 | 4/1997 |
| WO | WO-97/34536 A2 | 9/1997 |
| WO | WO-99/18866 A1 | 4/1999 |
| WO | WO-99/21500 A1 | 5/1999 |
| WO | WO-00/67651 A1 | 11/2000 |
| WO | WO-01/08571 A1 | 2/2001 |
| WO | WO-01/62168 A2 | 8/2001 |
| WO | WO-02/07901 A1 | 1/2002 |
| WO | WO-02/34120 A2 | 5/2002 |
| WO | WO-02/076311 A2 | 10/2002 |
| WO | WO-03/026482 A2 | 4/2003 |
| WO | WO-03/066147 A1 | 8/2003 |
| WO | WO-2004/002331 A1 | 1/2004 |
| WO | WO-2004/028351 A2 | 4/2004 |
| WO | WO-2004/043272 A1 | 5/2004 |
| WO | WO-2004/056267 A1 | 7/2004 |
| WO | WO-2004/078066 A2 | 9/2004 |
| WO | WO-2004/080316 A1 | 9/2004 |
| WO | WO-2004/096080 A2 | 11/2004 |
| WO | WO-2005/009300 A1 | 2/2005 |
| WO | WO-2005/057467 A2 | 6/2005 |
| WO | WO-2005/077282 A1 | 8/2005 |
| WO | WO-2005/089433 A2 | 9/2005 |
| WO | WO-2006/009705 A2 | 1/2006 |
| WO | WO-2006/015302 A1 | 2/2006 |

(56) References Cited

FOREIGN PATENT DOCUMENTS

| | | |
|---|---|---|
| WO | WO-2006/017507 A2 | 2/2006 |
| WO | WO-2006/039279 A2 | 4/2006 |
| WO | WO-2006/042206 A2 | 4/2006 |
| WO | WO-2006/044727 A2 | 4/2006 |
| WO | WO-2006/047598 A1 | 5/2006 |
| WO | WO-2006/058079 A3 | 6/2006 |
| WO | WO-2006/058195 A2 | 6/2006 |
| WO | WO-2006/062555 A2 | 6/2006 |
| WO | WO-2006/086241 A2 | 8/2006 |
| WO | WO-2006/099285 A2 | 9/2006 |
| WO | WO-2006/102085 A2 | 9/2006 |
| WO | WO-2007/008709 A2 | 1/2007 |
| WO | WO-2007/021588 A1 | 2/2007 |
| WO | WO-2007/022194 A2 | 2/2007 |
| WO | WO-2007/059343 A2 | 2/2007 |
| WO | WO-2007/067632 A2 | 6/2007 |
| WO | WO-2008/008898 A2 | 1/2008 |
| WO | WO2008/070867 A2 | 6/2008 |
| WO | WO-2008/157513 A1 | 12/2008 |
| WO | WO-2009/012265 A2 | 1/2009 |
| WO | WO-2009/018220 A1 | 2/2009 |
| WO | WO-2009/021116 A2 | 2/2009 |
| WO | WO-2009/036156 A1 | 3/2009 |
| WO | WO-2009/046046 A1 | 4/2009 |
| WO | WO-2009/058566 A1 | 5/2009 |
| WO | WO-2009/151926 A2 | 12/2009 |
| WO | WO-2010/014538 | 4/2010 |

OTHER PUBLICATIONS

Schmitz et al.; U.S. Appl. No. 13/232,882 entilted "Tissue Modification Devices," filed Sep. 14, 2011.
Schmitz et al.; U.S. Appl. No. 13/267,683 entitled "Flexible Tissue Removal Devices and Methods," filed Oct. 6, 2011.
Sun et al.; U.S. Appl. No. 13/340,363 entitled "Flexible Neural Localization Devices and Mehtods," filed Dec. 29, 2011.
Wallace et al.; U.S. Appl. No. 13/338,103 entitled "Tissue Modification Devices and Methods," filed Dec. 27, 2011.
Wallace et al.; U.S. Appl. No. 13/338,134 entitled "Surgical Tools for Treatment of Spinal Stenosis," filed Dec. 27, 2011.
US Surgical Kerrison Spinal Rongeur K943116 [online] Retrieved from the internet: <URL: http://www.ussurg.com/uss/index.html> Jul. 27, 1994.
Edwards et al; "T-Saw Laminoplasty for the Management of Cervical Spondylotic Myelopathy," SPINE, Lippincott Williams & Wilkins, Inc., 2000, vol. 25 (14): 1788-1794, Jan. 1, 2000.
Honl et al; "The Use of Water-Jetting Technology in Prostheses Revision Surgery—First Results of Parameter Studies on Bone and Bone Cement," J. Biomed Mater Res (Applied Biomaterials), John Wiley & Sons, Inc, 2000, 53, 6: 781-790 Jan. 1, 2000.
Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917-922. Jan. 1, 2000.
Abdel-Wanis et al., "Tumor growth potential after tumoral and instrumental contamination: an in-vivo comparative study of T-saw, Gigli saw, and scalpel," Journal of orthopaedic science, 2001, vol. 6, 424-429. Jan. 1, 2001.
Hara et al., "En Bloc Laminoplasty Performed with Threadwire Saw: Technical Note," Neurosurgery, Jan. 2001, vol. 48, No. 1, pp. 235-239. Jan. 1, 2001.
Hata et al; "A less invasive surgery for rotator cuff tear: Mini-open repair," Journal of Shoulder and Elbow Surgery, 2001, vol. 10 No. 1, 11-16. Jan. 1, 2001.
Sen, Cengiz, Tibia proksimalinde Gigli testeresi ile yapılanperkutan osteotominin güvenilirligi: Kadavra calismasi, Acta orthopaedica et traumatologica turcica, 2002, vol. 36, 136-140; (In Russian w/ Eng Summary) Jan. 1, 2002.
Shiraishi T., "A new technique for exposure of the cervical spine laminate," Journal of neurosurgery, Spine, 2002, vol. 96(1), 122-126. Jan. 1, 2002.
Shiraishi T., Skip laminectomy—a new treatment for cervical spondylotic myelopathy, preserving bilateral muscular attachments to the spinous processes; a preliminary report, Spine, 2002, vol. 2(2), 108-115. Jan. 1, 2002.
Tomita et al., "The Use of the T-Saw for Expansive Midline laminoplasty in the Treatment of Cervical Myelopathy," Orthopedics and Traumatology, No. 3, pp. 169-178, 2002. Jan. 1, 2002.
Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680-684. Jan. 1, 2003.
Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187-E190. Jan. 1, 2003.
Shiraishi et al., "Results of Skip Laminectomy -Minimium 2-Yeat Follow-up Study Compared with Open-Door Laminoplasty," Spine, Lippincott Williams & Wilkins Inc., 2003, vol. 28 No. 24, 2667-2672. Jan. 1, 2003.
Takada et al., "Unusual Metastasis to the Cauda Equina From Renal Cell Carcinoma," SPINE, Lippincott Williams & Wilkins, Inc., 2003, vol. 26 No. 6, E114-E117. Jan. 1, 2003.
Eralp et al., "A comparison of two osteotomy techniques for tibial lengthening," Archives of orthopardic and trauma surgery, 2004, vol. 124:298-300, Jan. 1, 2004.
Skippen et al., "The Chain Saw—A Scottish Invention," Scottish Medical Journal, 2004, vol. 49(2), 72-75. Jan. 1, 2004.
Bohinski et al., "Novel use of a threadwire saw for high sacral amputation," Journal of neurosurgery: Spine, 2005, vol. 3, 71-78. Jan. 1, 2005.
Nakagiri et al., "Thoracoscopic Rib Resection Using a Gigli Saw," The Annals of Thoracic Surgery, 2005, vol. 80, 755-756. Jan. 1, 2005.
Osaka et al., "Clinical signifance of a wide excision policy for sacrococcygeal chordoma," J Cancer Res Clin Oncol, 2005, Total pp. 6. Jan. 1, 2005.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_ste Jan. 1, 2006.
Park et al; "Cases of the Excision of Carious Joints," John Scrymgeour, Glasgow, 1806, Total pp. 6, Jan. 1, 1806.
Pancoast, Joseph, "A Treatise on Operative Surgery," Carey and Hart, Philadelphia, 1844, Total pp. 11. Jan. 1, 1844.
Truax, Charles, "The Mechanics of Surgery," Chicago, IL; 1899, Total pp. 3. Jan. 1, 1899.
Burrows, Harold, "Surgical instruments and appliances used in operations," Faber and Faber, London, 1937, total pp. 4. Jan. 1, 1937.
Wilkins, Robert H, "Neurosurgical Classics," Johnson Reprint Corporation, New York, 1965, 377-382. Jan. 1, 1965.
Dammann, Gordon, Pictorial Encyclopedia of Civil War Medical Instruments and Equipment, Pictorial Histories Publishing Company, Missoula, Montana, 1983, Total pp. 2. Jan. 1, 1983.
Barer Malvin, "Instrument to Enhance Passage of the Gigli Saw," Journal of Pediatric Orthopedics, Raven Press, New York, 1984, 4:762-763. Jan. 1, 1984.
Paley et al., "Percutaneous Osteotomies," Orthopedics Clinics of North America, 1991, vol. 22 No. 4, 613-624. Jan. 1, 1991.
Paktiss et al., "Afghan Percutaneous Osteotomy," Journal of Pediatric Orthopaedics, Raven Press Ltd, New York, 1993, vol. 13 No. 4, 531-533. Jan. 1, 1993.
Peltier, Leonard Orthopedics: A History and Iconography, Norman Publishing, San Francisco, 1993, Total pp. 3. Jan. 1, 1993.
Rutkow, Ira, "Surgery An Illustrated History," Mosby—Year Book, Inc., St. Louis, 1993, Total pp. 4. Jan. 1, 1993.
Goel, Atul, "Neurosurgical forum, Supraorbital Craniotomy," Journal of Neurosurgery, 1994, vol. 81, 642-643. Jan. 1, 1994.
Tomita et al., "Total eb bloc spondylectomy and circumspinal decompression for solitary spinal metastasis," Paralegia, 1994, 32:36-46. Jan. 1, 1994.
Tomita K. et al., "Total en bloc spondylectomy for solitary spinal metastases," International Orthopaedics (SICOT), 1994, 18: 291-298. Jan. 1, 1994.

(56) References Cited

OTHER PUBLICATIONS

Brunori et al., "Celebrating the centennial (1894-1994): Leonardo Gigli and his wire saw," J. Neurosurg, 1995, 82:1086-1090. Jan. 1, 1995.

Tomita et al., "The Threadwire Saw: a New Device for Cutiing Bone," The Journal of Bone and Joint Surgery, 1996, vol. 78, 1915-1917. Jan. 1, 1996.

Baumgart et al., "Indikation and Technik der Knochendurchtrennung," Der Chirurg, 1998, vol. 69:1188-1196. (in German with Eng Summary). Jan. 1, 1998.

Stevens et al., "Calvarial Bone Graft Harvest Using the Gigli Saw," Journal of Oral and Maxillofacial Surgery, 1998, vol. 56, 798-799. Jan. 1, 1998.

Tomita et al., "Expansive Midline T-Saw Laminoplasty (Modified Spinour Process-Splitting for the Management for Cervical Myelopathy," SPINE, Lippincott Williams & Wilkins, Inc, 1998, 23(1), 32-37. Jan. 1, 1998.

Fujita et al., "Chordoma in the Cervical Spine Managed with En Bloc Excision," SPINE, Lippincott Williams & Wilkins Inc, 1999, 24 (17), 1848-1851. Jan 1, 1999.

Gore Smoother User Manual, W. L. Gore & Associates Inc. Flagstaff, AZ, Dec. 1999. Total pp. 3. Jan. 1, 1999.

Kawahara et al., "Recapping T-Saw Laminoplasty for Spinal Cord Tumors," SPINE, 1999, vol. 24 No. 13, pp. 1363-1370. Jan. 1, 1999.

Peavy et al., "Comparison of Cortical Bone Abiations by Using Infrared Laser Wavelengths 2.9 to 9.2 μm, Lasers in Surgery and Medicine," 1999, vol. 26, 421-434. Jan. 1, 1999.

Zeppelin Laminectomy Rongeur K901372, [online]Retrieved from the internet <URL: http://www.zeppelin-medical.com/download/instrument.pdf>, Oct. 24, 2006.

Reckling Frederick, "Modified Stethoscope Earpiece Makes Excellent Gigli Saw Guide," J Bone and Joint Surgery Am, Dec. 1972, 54-A(8), 1787-1788. Dec. 1, 1972.

Ellman Int. Disc-FX System Accessories K052241 [online]Retrieved from the Internet: <URL: http://www.ellman.com/_medical/ >. Feb. 27, 2006.

Bartol et al., "Arthoroscopic Microscopic Discectomy in Awake Patients: The Effectiveness of Local/Neurolept Anaesthetic," Canadian Spine Society Meeting, Vernon BC, Canada, Mar. 2002.

Bartol et al., "Use of Neve Stimulator to Localise the Spinal Nerce Root During Arthroscopic Discectomy Procedures," Canadian Spine Society Meeting, Vernon BC, Canada, Mar. 2002.

Ohta et al., "Superimposed Mechanomygraphic Response at Different Contraction Intensity in Medial Gastrocnemius and Soleus Muscles," International Journal of Sport and Health Science: vol. 5, 63-70, 2007.

Schwieger et al., "Abrasive Water Jet Cutting as a New Procedure for Cutting Cancellous Bone—In Vitro Testing in Comparison with the Oscillating Saw," Wiley Interscience, www.interscience.wiley.com. Sep. 20, 2004, 223-228, Sep. 20, 2004.

Mopec Bone-Cutting tool, Product brochure, Total pp.4, First accessed Dec. 15, 2005.

Codman Laminectomy Shaver ( a Johnson & Johnson company www.codman.com) catalogue, pp. 416-431, [online] Retrieved from the internet: <URL: http:llwww.codman.com/PDFs/Catalog_04_R.pdf> First accessed Oct. 24, 2006.

Integra Ruggles TM Kerrison Rongeurs [online ]Retrieved from the internet <URL: http://www.integra-ls.com/products!? product=22>. First accessed Oct. 24, 2006.

Herkowitz, "The Cervical Spine Surgery Atlas", Herkowtiz,"*The Cervical Spine Surgery Atlas*", 2004, 2nd Edition Jan. 1, 2004, 203-206, 208.

Schmitz et al.; U.S. Appl. No. 13/588,969 entitled "Access and Tissue Modification Systems and Methods," filed Aug. 17, 2012.

Saadat et al.; U.S. Appl. No. 13/913,801 entitled "Powered Tissue Modification Devices and Methods," filed Jun. 10, 2013.

Leguidleguid et al.; U.S. Appl. No. 14/061,641 entitled "Tissue Modification Devices," filed Oct. 23, 2013.

Schmitz et al.; U.S. Appl No. 14/064,085 entitled "Access and Tissue Modification Systems and Methods," filed Oct. 25, 2013.

Schmitz et al.; U.S. Appl. No. 14/082,052 entitled "Flexible Tissue Removal Devices and Methods," filed Nov. 15, 2013.

Bleich et al.; U.S. Appl. No. 14/180,221 entitled "Flexible tissue rasp," filed Feb. 13, 2014.

* cited by examiner

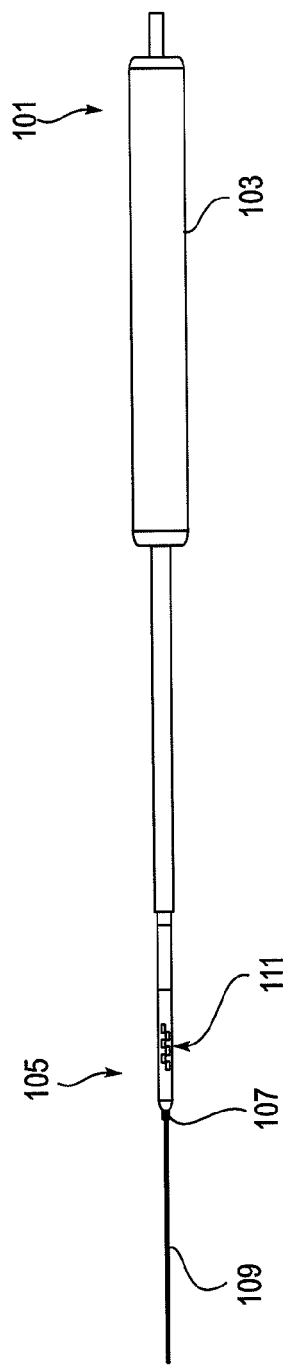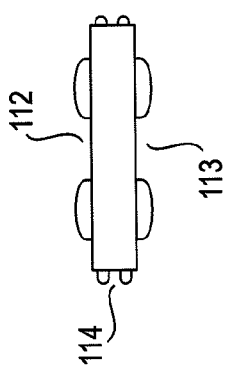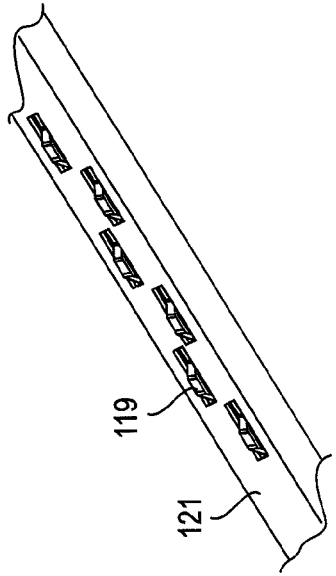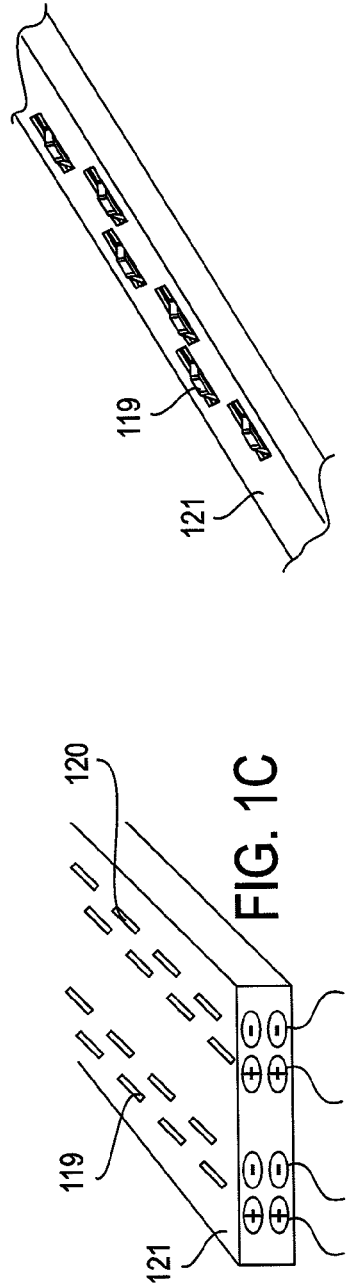

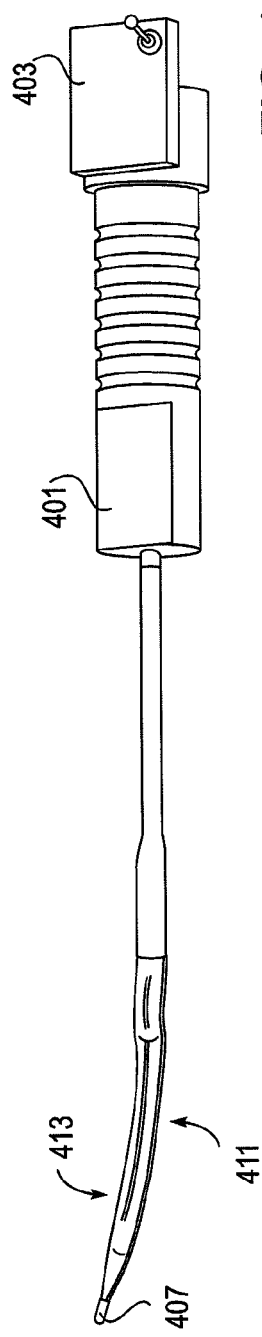
FIG. 4A
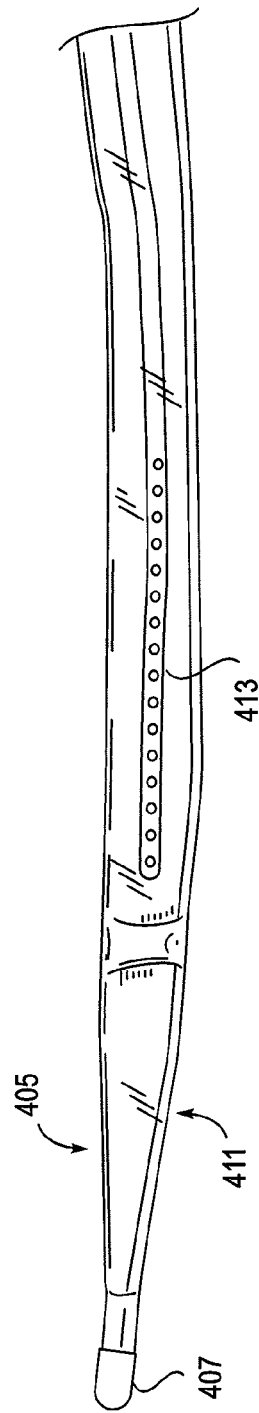
FIG. 4B
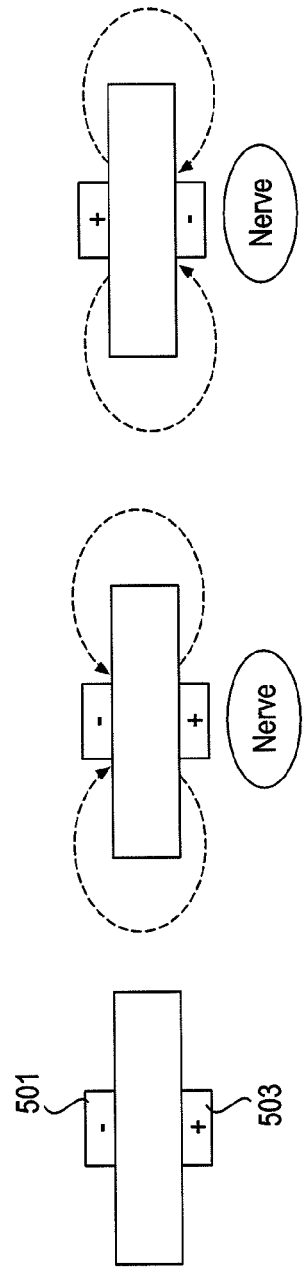
FIG. 5C
FIG. 5B
FIG. 5A

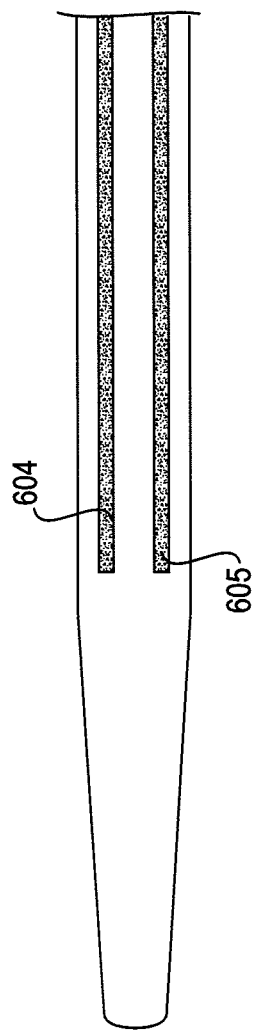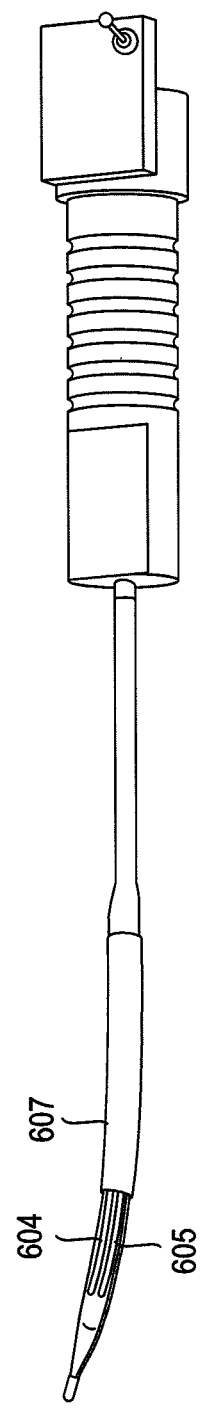

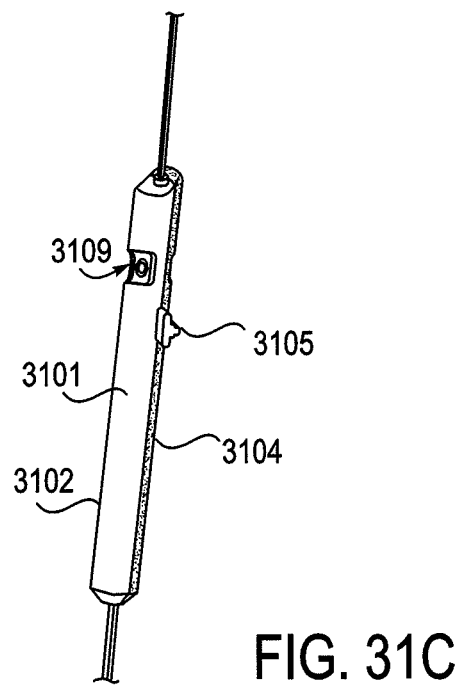
FIG. 31C
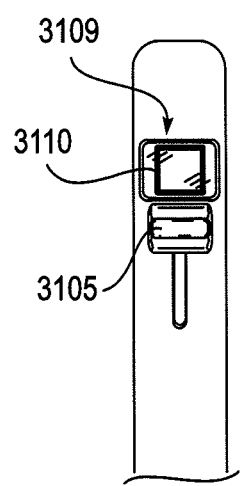
FIG. 32A
FIG. 32B
FIG. 32C

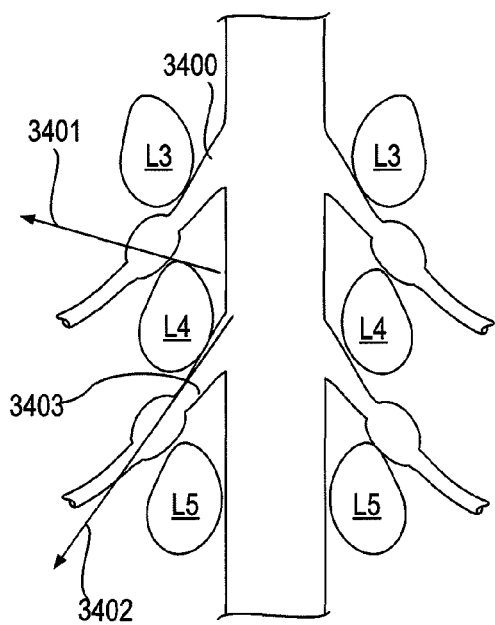 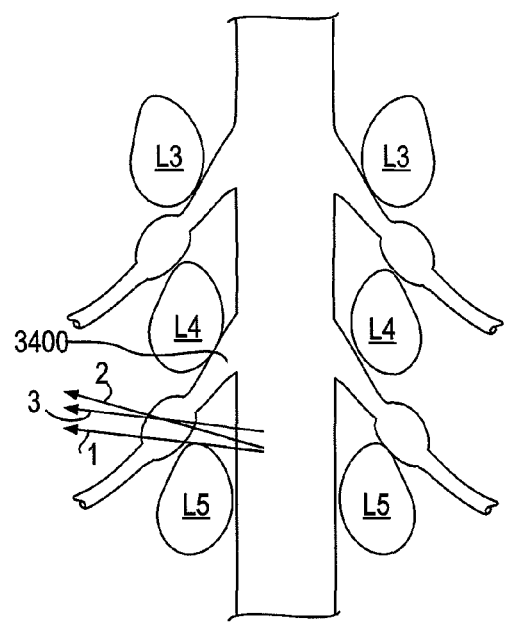
FIG. 34A  FIG. 34B
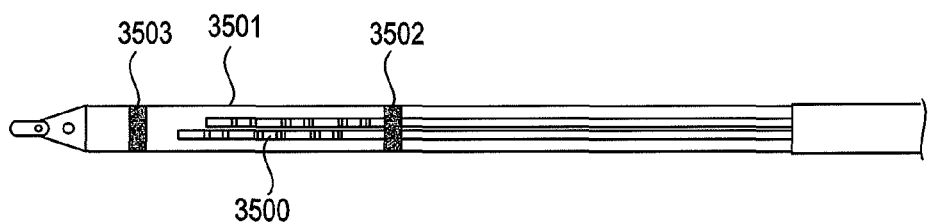
FIG. 35

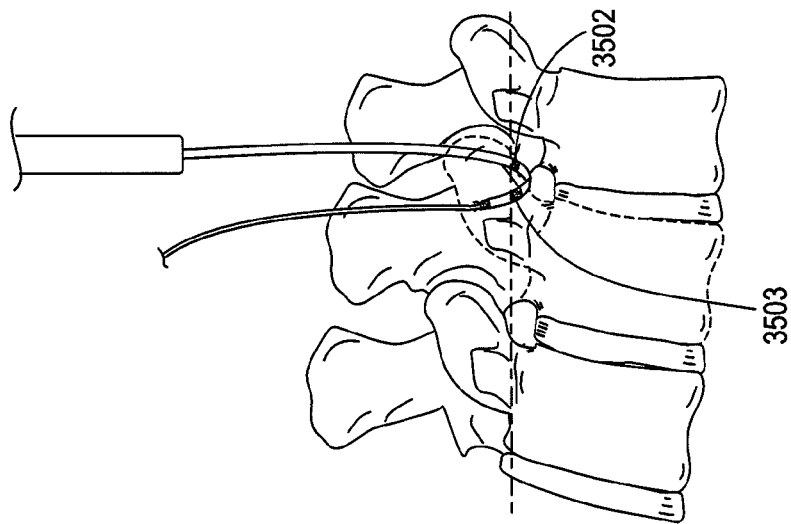
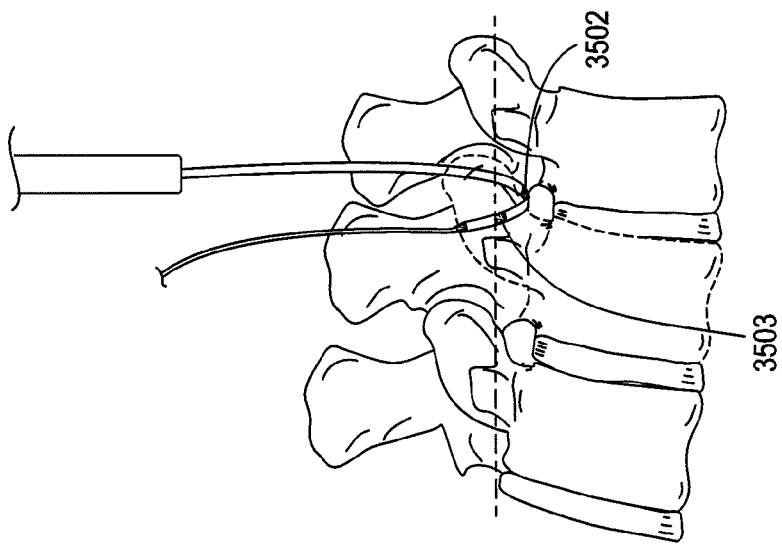
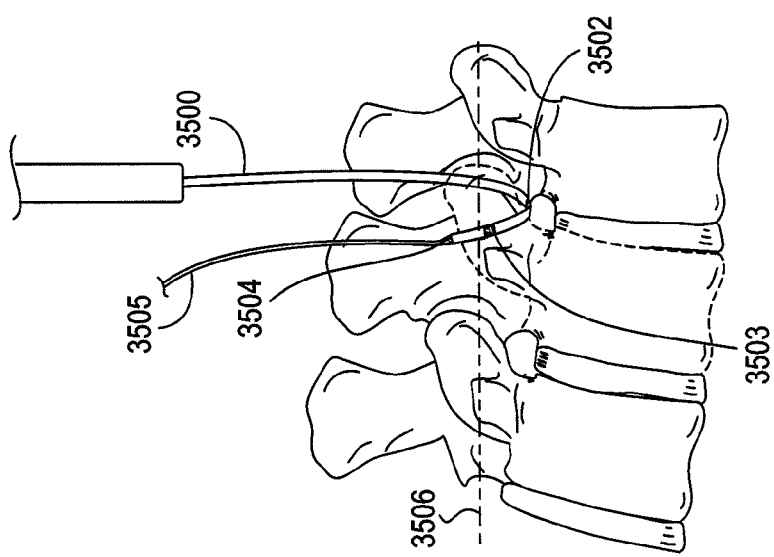
FIG. 36C
FIG. 36B
FIG. 36A

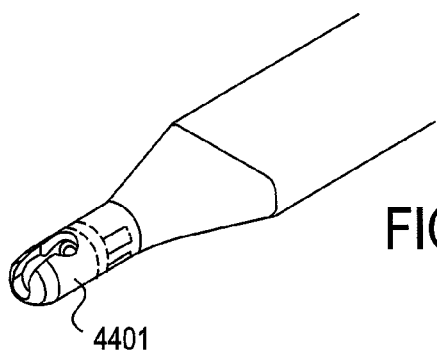
FIG. 43
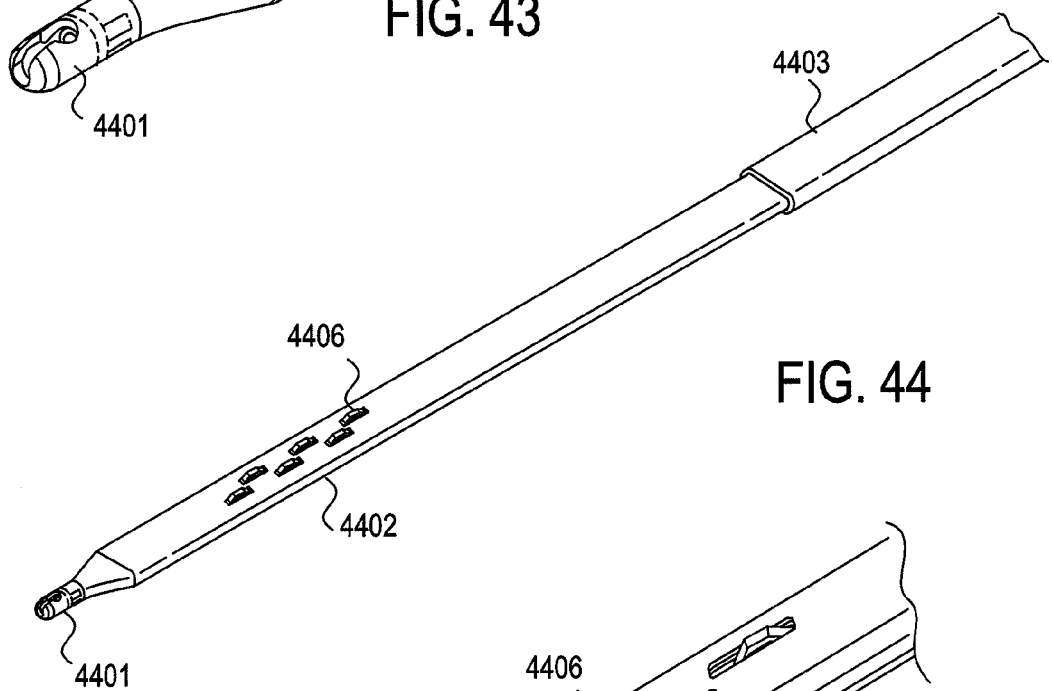
FIG. 44
FIG. 45
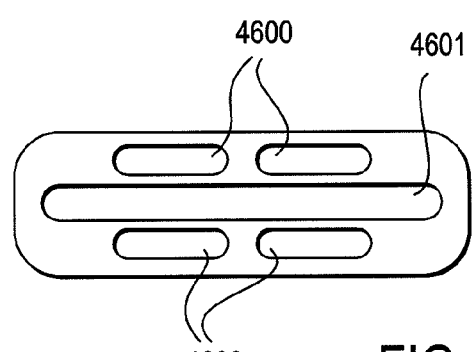
FIG. 46

FLEXIBLE NEURAL LOCALIZATION DEVICES AND METHODS

CROSS REFERENCE TO RELATED APPLICATIONS

This patent application is a continuation-in-part of U.S. patent application Ser. No. 12/724,315, titled "FLEXIBLE NEURAL LOCALIZATION DEVICES AND METHODS", filed on Mar. 15, 2010, now Publication No. U.S.-2011-0004207-A1; which is a continuation-in-part of U.S. patent application Ser. No. 12/504,545, titled "SPINAL ACCESS AND NEURAL LOCALIZATION", filed on Jul. 16, 2009 now U.S. Pat. No. 8,419,653 , now Publication No. U.S.-2010-0010334-A1; which is a divisional of U.S. patent application Ser. No. 11/457,416, titled "SPINAL ACCESS AND NEURAL LOCALIZATION", filed on Jul. 13, 2006, now U.S. Pat. No. 7,578,819; which is a continuation-in-part of U.S. patent application Ser. No. 11/251,205, titled "DEVICES AND METHODS FOR TISSUE ACCESS", filed on Oct. 15, 2005, now U.S. Pat. No. 7,918,849. Each of these applications is herein incorporated by reference in its entirety.

U.S. patent application Ser. No. 12/724,315 is also a continuation-in-part of U.S. patent application Ser. No. 11/251,205, titled "DEVICES AND METHODS FOR TISSUE ACCESS", filed on Oct. 15, 2005, now U.S. Pat. No. 7,918,849, each of these applications is herein incorporated by reference in its entirety.

U.S. patent application Ser. No. 12/724,315 also claims the benefit of U.S. Provisional Patent Application No. 61/160,164, titled "FLEXIBLE NEURAL LOCALIZATION DEVICES AND METHODS", filed on Mar. 13, 2009; U.S. Provisional Patent Application No. 61/220,314, titled "SURGICAL TOOLS FOR TREATMENT OF SPINAL STENOSIS", filed on Jun. 25, 2009; U.S. Provisional Patent Application No. 61/254,406, titled "FLEXIBLE NEURAL LOCALIZATION DEVICES AND METHODS", filed on Oct. 23, 2009; U.S. Provisional Patent Application No. 61/292,840, titled "BIO-IMPEDANCE NEURAL LOCALIZATION DEVICES AND METHODS", filed on Jan. 6, 2010; U.S. Provisional Patent Application No. 61/299,303, titled "NEURAL LOCALIZATION DEVICES AND METHODS", filed on Jan. 28, 2010; and U.S. Provisional Patent Application No. 61/301,568, titled "DEVICES AND METHODS FOR TISSUE ACCESS AND MODIFICATION", filed on Feb. 4, 2010, each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are flexible devices, and methods of using them, for determining if a nerve is nearby a region of the device as part of a surgical procedure, specifically which side of a device a nerve or nerve root (e.g., spinal nerve) is on relative to the device. In particular, described herein are flexible neural localization devices that may be used during a spinal decompression procedure.

BACKGROUND

Surgical intervention may require the manipulation of one or more medical devices in close proximity to a nerve or nerves, which may risk damage to the nerve tissue. For example, medical devices may be used to cut, extract, suture, coagulate, or otherwise manipulate tissue including tissue near or adjacent to neural tissue. Spinal decompressions, which may be preformed to remove tissue that is impinging on a spinal nerve is another such example. It would therefore be beneficial to precisely determine the location and/or orientation of neural tissue when performing a medical procedure to prevent damage to the neural tissue.

For example, knowing the location or orientation of a nerve in relation to a medical device (e.g., a probe, retractor, scalpel, etc.) would enable more accurate medical procedures, and may prevent unnecessary damage to nearby nerves. Although systems for monitoring neural tissue have been described, these systems are typically imprecise. Further, many of these systems require large current densities (which may also damage tissue) and may be severely limited in their ability to accurately guide surgical procedures. For example, in many such systems a current is applied from an electrode (e.g., a needle electrode) in order to evoke an efferent muscular response such as a twitch or EMG response. Such systems typically broadcast, via the applied current, from the electrode and the current passes through nearby tissue until it is sufficiently near a nerve that the current density is adequate to depolarize the nerve.

Because the conductance of biological tissue may vary between individuals, over time in the same individual, and within different tissue regions of the same individual, it has been particularly difficult to predictably regulate the applied current. Furthermore, the broadcast fields generated by such systems are typically limited in their ability to spatially resolve nerve location and/or orientation with respect to the medical device.

For example, U.S. patent application 2005/0075578 to Gharib et. al. and US 2005/0182454 to Gharib et al. describe a system and related methods to determine nerve proximity and nerve direction. Similarly, U.S. Pat. No. 6,564,078 to Marino et al. describes a nerve surveillance cannula system and U.S. 2007/016097 to Farquhar et al. describes a system and method for determining nerve proximity and direction. These devices generally apply electrical current to send current into the tissue and thereby depolarize nearby nerves. Although multiple electrodes may be used to stimulate the tissue, the devices, systems and methods described are do not substantially control the broadcast field. Thus, these systems may be limited by the amount of current applied, and the region over which they can detect nerves.

In addition, many surgical manipulations, particularly spinal decompressions, must be performed in difficult to reach regions, and the surgical procedures performed may necessarily need to navigate narrow and tortuous pathways. Thus, it would be of particular interest to provide devices that are extremely low profile, and/or are adapted for use with existing low-profile surgical devices and systems. Furthermore, it would be of particular interest to provide extremely low profile devices that are flexible and can be moved toward and away from a nerve or nerve root to increase their ability to spatially resolve nerve location and/or orientation with respect to the medical device.

Described herein are devices, systems and methods that may address many of the problems and identified needs described above.

SUMMARY OF THE DISCLOSURE

Described herein are devices, systems and methods for determining which direction a nerve is located relative to a device or portion of a device, or along a pathway through the tissue. The neural stimulation tools described herein are configured to be flexible and low-profile, so that they can be used within body regions that may be tortuous or difficult to reach, such as within a compressed or partially occluded neural foramen. In most cases, these tools described herein are adapted to be manipulated bimanually, for example, by applying force to both of the ends of the devices from separate locations, usually from outside the body. Thus, in many of the exemplary devices (tools) described herein, the distal end region of the tools are configured to couple to the proximal end of a guidewire, and the methods of using such devices may include the step of pulling the devices into position by pulling and/or pushing from either or both the distal and/or proximal ends.

The devices and tools described herein may generally be referred to as "neural localization ribbon" (or "NLR") tools or devices, or alternatively as "neural localization" devices, or "neuro localization" devices. In general, these devices have a flexible body supporting one or more electrodes. The electrodes may be configured to project an electromagnetic field that can controllably stimulate a nearby nerve (e.g., a nerve that is within a predetermined distance from a portion of the device). The electrodes may be configured to stimulate only nerves nearby the NLR device based on one or more of: the size of the exposed electrode surface; and the position of the electrode(s), including the distance of the electrode(s) from the edges of the NLR device and/or the spacing between electrodes (including the spacing between electrodes in bipolar or other multi-polar configurations). The power (e.g., current or voltage) applied may also be regulated or limited to control the broadcast field.

As mentioned, the flexible body may be a flexible ribbon-shaped body. For example, the body may be elongate and very thin, with a width greater than the thickness, and a length much greater than the width. The device may be more flexible in some directions than in others. For example, the device may be very flexible in the direction perpendicular to the width, but not in the direction parallel to the width.

The NLR devices described herein may be stand-alone tools, and/or they may be configured to couple with one or more other tools, including tissue modification tools. In some variations, the NLR devices may be integrated with a tissue modification tool. For example, a device may include an NLR region distal to a tissue modification region.

In general, these devices may include multiple electrodes arranged along one or more surfaces of the NLR device. For example, the devices may include a series of bipolar electrodes (such as alternating anodes and cathodes) to form one variation of a bipole network. Other multipolar (e.g., tripolar, quadrapolar, etc.) configurations may also be used. Thus, the stimulation electrodes may be arranged in a monopolar, bipolar, tripolar, quadrapolar, or other configuration. In particular, a set of electrodes may be arranged in a line or pattern that extends at least partially across or along a surface of the device. The set of electrodes may include a plurality of electrodes that are electrically coupled (e.g., connected to the same annodal or cathodal source). Thus, the electrode or set of electrodes may create a broadcast field that extends a controlled (typically small) distance from the flexible body, allowing the device to reliably determine proximity of a nerve. The NLR devices described herein may also include multiple sets of electrodes for applying neural stimulation. For example, in some variations, a first stimulation electrode or set of electrodes are included on a first side (e.g., the top) of the device and a second set of separately controllable electrodes are included on a second side (e.g., the bottom) of the device.

As mentioned, the devices described herein may be configured as a stand-alone NLR device that may be used independently of a tissue modification device. Such NLR devices typically include a flexible body region that has a first (e.g., top) side and a second (e.g., bottom) side, a distal end region that is configured to releasably couple to a guidewire, and a proximal end region that is configured to include or engage with a handle. An electrode or set of electrodes may be arranged on at least one side of the neural localization ribbon device.

The neural localization devices described herein are generally adapted for use in tortuous and narrow body regions, such as through a neural foramen of the spine. For example, the devices described herein may be flexible enough so that they can be drawn (e.g., pulled) through a narrow and bending body region to determine if a nerve is nearby. Thus, the devices described herein may be adapted for use with a bimanual system for positioning and operating tissue modification devices. A bimanual device may be pulled or drawn against a target tissue by pulling both end regions of the device from opposite directions. For example, a bimanual device may be positioned within a patient by first passing a guidewire from outside of the patient, around a target tissue, and back outside of the patient. The guidewire may then be used to pull a device, such as the flexible tissue localization devices described herein, or a tissue modification device, or both, into position near the target region. For example, the distal end region of the tissue modification device and/or neural localization device may be coupled to the guidewire, and the guidewire may be pulled from the patient (distally) to position the device. The guidewire may also be used to manipulate or operate other devices, particularly tissue modification devices that are reciprocated against the tissue.

In some variations, the NLR devices described herein are configured to be used in combination with one or more other devices, including tissue modification devices. For example, the NLR device may be adapted to couple with the end, e.g., the distal end, of a tissue modification device. Examples of tissue modification devices may be found in many of the patent applications previously incorporated by reference, for example, U.S. Ser. No. 12/324,147. The NLR device may be a separate device that couples with a tissue modification device, or it may be an integral portion of the tissue modification device. For example, a tissue modification device may include a distal region including a flexible NLR region.

An NLR device may couple with a tissue modification device in any appropriate manner. For example, a flexible neural localization device may be coupled to a tissue modification device by coupling to the distal end of the tissue modification device. The coupling may be an attachment such as the guidewire attachment region of a tissue modification device. Thus, the same coupler at the distal end of a tissue modification device may be used to couple to a guidewire and to an NLR device (or an adapter for coupling to an NLR device). In some variations the flexible neural localization device is configured as a sleeve into which at least a portion of the tissue modification device fits. The NLR device may be a tear-away cover or sleeve. For example, a tear-away sleeve may cover all or a portion of a tissue modification device but is removable by either pulling it distally or pulling it off through a slit or frangible region of the NLR device. In some variations, the NLR device includes a track or channel through which the tissue modification device may fit.

The flexible NLR devices described herein may also be adapted to expand or measure a body region. For example, a flexible NLR device may be adapted to dilate a body region. The flexible neural localization device may include a wedge-shaped, and/or expandable region. The flexible neural localization devices described herein may also be adapted to provide drug delivery (e.g., including one or more channels for drug delivery). In some variations, the flexible neural localization devices described may also include additional electrodes, or be adapted for their own electrodes, to apply radio-frequency (RF) energy to coagulate or ablate tissue.

Examples of many of these variations are illustrated below. It should be understood that aspects of the illustrated examples may be omitted, duplicated or combined with other features of flexible neural localization devices and still be within the scope of the devices, systems and methods described herein.

For example, described herein are ribbon neural localization devices capable of determining if a nerve is nearby a region of the device, the device comprising: a ribbon-shaped flexible elongate body having a first side and a second side, wherein the first and second sides are substantially parallel; a stimulation region on the first side including a stimulation electrode that is configured to emit a limited neural stimulation field along at least a portion of the length of the first side; and a guidewire coupler at the distal end region of the elongate body.

In another example, the flexible neural localization devices capable of determining if a nerve is nearby a region of the device include: a flexible elongate body having an axial length, a width and a thickness, wherein the axial length is greater than the width, and the width is greater than the thickness; a stimulation region of the elongate body including a bipolar network, wherein the bipolar network comprises an anode and a cathode configured to form a bipole field; and a guidewire coupler at the distal end region of the elongate body.

In yet another example, the flexible neural localization devices capable of determining if a nerve is nearby one or more regions of the device include: a flexible elongate body having a first side and a second side, wherein the first and second sides are substantially parallel; a first bipole network arranged along the first side and configured to emit an effectively continuous bipole field along at least a portion of the first side; a second bipole network arranged along the second side and configured to emit an effectively continuous bipole field along at least a portion of the second side; and a guidewire coupler at the distal end region of the elongate body.

In any of these variations, the bipolar electrode pair may be located at the distal end of the elongate body. The elongate body may be ribbon-shaped. In some variations, the width of the elongate body varies along the length of the elongate body. For example, the width of the distal portion of the elongate body may be less than the width of the proximal portion of the elongate body. The thickness of the elongate body may vary along the length of the elongate body. For example, the thickness of the distal portion of the elongate body may be less than the thickness of the proximal portion of the elongate body. The devices may include one or more radio-opaque markers distributed along the length of the elongate body.

Any of the NLR devices described herein may also include a handle or a handle attachment region at the proximal end region of the device. Some variations of the NLR devices described herein may include an expandable balloon along at least a portion of the length, and/or a channel disposed along the length of the elongate body. For example, the device may include a channel in fluid communication with a drug reservoir, an irrigation fluid reservoir, and/or a suction device.

The stimulation region of the NLR device may be arranged on one or more surface of the NLR device. For example, the NLR device may include a first surface on the flexible elongate body, wherein the stimulation region is arranged on the first surface.

The electrodes (e.g., the bipole network) on the NLR device may comprises a plurality of anodes and a plurality of cathodes, wherein the plurality of anodes and the plurality of cathodes are configured to form an effectively continuous bipole field along a portion of the flexible elongate body. The plurality of anodes may be in electrical communication with a first anodal conductor. The plurality of cathodes may be in electrical communication with a first cathodal conductor.

In some variations, the anodes are arranged in a line, and/or the cathodes are arranged in a line. Other arrangement of anodes and cathodes may be used. In general, the cathodes and anodes forming a bipole network may extend along a portion of the length of the NLR device.

Also described herein are methods of determining if a nerve is nearby a region of a device, the method including the steps of: passing a ribbon neural localization device at least partially around a target tissue, wherein the ribbon neural localization device comprises a ribbon-shaped flexible elongate body having a first side and a second side that are substantially parallel and a stimulation region on the first side having a stimulation electrode; energizing the stimulation electrode to emit a limited neural stimulation field along at least a portion of the length of the first side; and determining if a nerve has been stimulated by the emitted field.

The step of passing the ribbon neural localization device at least partially around the target tissue may include passing a guidewire at least partially around the target tissue and pulling the device around the target tissue using the guidewire. The step of passing the ribbon neural localization device may comprise applying tension to both the proximal end and the distal end of the ribbon neural localization device.

For any of the methods involving the NLR devices (or systems including an NLR device), the target tissue may be any appropriate tissue, including tissue to be modified or removed. For example, the target tissue may comprise tissue within a spinal foramen. The target tissue may include, but is not limited to, spinal ligament (such as ligamentum flavum) and/or bony tissue (such as an superior articular process, inferior articular process, pedicle, lamina, or any other suitable vertebral bony tissue). Non-target tissue may include nerve (neural) tissue.

Also described herein are methods of modifying tissue, the method comprising the steps of: passing a ribbon neural localization device at least partially around a target tissue, wherein the ribbon neural localization device comprises a ribbon-shaped flexible elongate body having a first side and a second side that are substantially parallel and a stimulation region on the first side having a stimulation electrode; energizing the stimulation electrode to emit a limited neural stimulation field along at least a portion of the length of the first side; determining that a nerve is not adjacent to the first side of the ribbon neural localization device; passing a flexible tissue-modification device at least partially around the target tissue along the same pathway through the tissue as the neural localization device, wherein the flexible tissue-modification device comprises a flexible elongate body having a tissue modification region including at least one cutting edge oriented in the same direction as the first side of the ribbon neural localization device; urging the tissue-modification device against the target tissue by pulling the tissue-modification device from at least one end of the device; and cutting the target tissue with the cutting edge.

The step of passing the ribbon neural localization device at least partially around the target tissue may include: passing a guidewire around the target tissue; and pulling the neural localization device around the target tissue using the guidewire.

Any of the methods described herein may also include the steps of removing the ribbon neural localization device by pulling on the proximal end of the neural localization device and uncoupling the ribbon neural localization device from the guidewire. Similarly, the methods may include the step of coupling the flexible tissue-modification device to the guidewire.

The step of passing the flexible tissue-modification device may also include pulling the flexible tissue-modification device around the target tissue using a second guidewire, wherein the ribbon neural localization device is anterior to the flexible tissue-modification device.

The flexible tissue-modification device may be passed at least partially around the target tissue by: passing a guidewire around the target tissue; and pulling the flexible tissue-modification device around the target tissue using the guidewire. Thus, the proximal end of the guidewire may be coupled to the distal end of the neural localization device in a fixed manner. The tissue-modification device may be urged against the target tissue by applying tension to both the proximal end region and the distal end region of the tissue-modification device. Tension may be applied by pulling the distal end of the guidewire and the proximal end of the neural localization device.

Also described herein are systems capable of determining if a nerve is nearby one or more regions of a device, comprising: a neural localization device, a controller configured to apply energy to emit the bipole field of the first bipole network, and a guidewire configured to couple to the guidewire coupler on the neural localization (NLR) device. The neural localization device may include a flexible elongate body having an outer surface with a first region and a second region; a guidewire coupler at the distal end of the elongate body; and a first bipole network including a plurality of anodes and a plurality of cathodes, wherein the plurality of anodes and the plurality of cathodes are configured to emit an effectively continuous bipole field along the first region of outer surface.

The system may also include a power source connected to the controller. In some variations, the NLR device is configured to be powered from the distal end; in other variations, the NDR device is configured to provide power by a connection to the electrode(s) made at the distal end of the NLR device. For example, the NLR device may include an attachment region at the distal end for connecting to the electrode(s).

In some variations, the system may include a sensor for detecting stimulation of a nerve. Sensors may detect movement (e.g., muscle twitch, gross muscle movement, etc.), EMG, or the like.

The system may also include a handle or a handle attachment region at the proximal end of the NLR device.

In some variations, the system includes a tissue modification region proximal to the first region of the outer surface of the neural localization device. In some variations, the system includes a tissue modification device. The NLR device may be configured to couple to the tissue modification device, or the two may be configured to operate separately.

Also described herein are neural localization devices capable of determining if a nerve is nearby a region of the device. These devices may include: a flexible elongate body having a first side and a second side, wherein the first and second sides are substantially parallel; a stimulation region on the first side including a bipole pair that is configured to emit a limited neural stimulation field along at least a portion of the length of the first side; a proximal coupler at the proximal end region of the device configured to couple the distal end of a tissue modification device; and a guidewire coupler at the distal end region of the elongate body. The proximal coupler may include a cavity into which at least a portion of the distal end of a tissue modification device may fit. For example, the proximal coupler may be configured to be released by flexing the proximal end of the device.

Also described are methods of modifying tissue in the spine comprising the steps of: guiding the distal tip of a guidewire from outside of a patient, around a target tissue within the patient, and out of the patient, so that the proximal and distal ends of the guidewire extend from the patient; coupling the distal end of a flexible neural localization device to the proximal end of the guidewire; positioning the flexible neural localization device around the target tissue using the guidewire; determining if a nerve is present between the flexible neural localization device and the target tissue; positioning a tissue modification device around the target tissue using the guidewire; and urging the tissue modification device against the target tissue and modifying the target tissue using the tissue modification device.

In general, the step of positioning the flexible neural localization device using the guidewire may include pulling the distal end of the flexible neural localization device. The tissue modification device may be positioned by coupling the tissue modification device to the flexible neural localization device and pulling.

The methods of using any of the NLR devices described herein may also include the step of dilating the region around the target tissue using the neural localization device.

In any of the variations described herein, the electrodes may project from the surface(s) of the neural localization/neuro localization devices. For example, the electrodes may extend from the relatively flat surfaces of the top and/or bottom of the neuro localization ribbon devices. In this configuration the electrodes may be referred to as proud to the surface (top and/or bottom surfaces) of the device, or simply as "proud electrodes." The proud electrodes may be formed of any appropriately conductive material. For example, the proud electrodes may be formed of a conductive metal extending from the body of the ribbon-shaped device. All or a subset of the electrodes may be proud. The proud electrodes extend from a surface of the device by more than 0.01 mm, by 0.1 mm, by 0.5 mm, by 1 mm, by 1.5 mm, by 2 mm, etc. The proud electrodes described herein may provide a greater sensitivity to the neuro localization device compared to configuration having flush or recessed electrodes.

The neural localization/neuro localization devices described herein may include a flexible, elongate, ribbon-shaped body having a substantially flat cross-section. In general, the ribbon-shaped body may be configured to bend up or down along the length of the body (e.g., above and below the plane of the ribbon). The ribbon-shaped body may be configured so that it does not substantially flex to the sides—e.g., in the plane of the ribbon shaped (along the thin side of the ribbon-shaped body).

In some variations the neural localization devices described herein have an H-shaped (or I-shaped) cross-sectional configuration. In this variation, the outer surfaces (the "top" and "bottom" surfaces) may form bipolar electrode pairs with electrodes on inner surfaces. This may limit current emitted by the "top" electrodes on the ribbon-shaped devices to prevent stimulation on the bottom of the device, and likewise for electrodes on the bottom outer surface, that may pair with electrodes on the bottom inner surface.

Any of the variations described herein may be used in either bipolar or monopolar configurations. In either monopolar or bipolar configurations the polarity of the electrode (e.g., anode/cathode or emitter/ground) may be reversed. In some circumstances a nerve may be more sensitive to cathodal rather than annodal stimulation, or vice-versa. Thus, it may be worthwhile to reverse the polarity to stimulate the same set of electrodes as either a cathode or an anode.

Any of the device variations described herein may also include electrodes that are concentrically arranged. For example, a ribbon-shaped device may have a top surface with one or more electrode pairs and a bottom surface with one or more electrodes pairs. The electrode pairs may be arranged so that an inner (e.g., −) electrode is surrounded by an outer (+) electrode, or with an inner (+) electrode surrounded by an outer (−) electrode. Concentrically arranged electrodes may provide a limited spread of current compared to bipolar electrode pairs that are not concentric (e.g., arranged adjacently). Surrounding the negative pole with the positive pole of the bipolar pair may therefore help control the current direction.

The devices described herein may include one or more markers to aid in visualization and orientation during the performance of the procedure. For example, the devices described herein may include one or more radioopaque markers to aid in visualization using imaging techniques such as fluoroscopy. In some variations the devices include a pair of markers that bracket the neuro stimulation region. For example, the device may include a pair of radioopaque rings/coils on either side of the neuro stimulation region of the device. The neuro stimulation region of the device in these examples may be region in which one or a plurality of electrodes is arranged. A marker may be a dense material such as platinum iridium, or it may be the absence of a dense material (e.g., a hole). For example, in some variations the markers are one or more holes through the elongate body of the device, which may show up as lighter regions on the device under fluoroscopy.

Markers may be used to help position the devices appropriately so that the stimulation region may be positioned as desired relative to the target tissue.

In general, the devices and methods described herein are particularly appropriate for use as part of a spinal decompression procedure for a neural foramen in the spine. The ribbon-shaped devices described herein may be positioned within a spinal foramen as previously described, e.g., by pulling in to the foramen using a guidewire coupled to the distal end of the ribbon-shaped device. When pulled into position using a guidewire coupled to the distal end of the device, the device may be manipulated proximally (e.g., using a handle or the distal end of the ribbon-shaped device) and distally using the coupled guidewire. In some variations the distal end of the device is configured to extend from the patient so that the guidewire may be de-coupled from the device (or so that it may be used without a separate guidewire). Once in position, the neural localization device may then be manipulated (e.g., positioned within the body) by pulling on the distal end (e.g., pulling the guidewire that exits the patient from a second site), and/or by pushing from the proximal end (e.g., pushing on a handle region of the neural localization device).

Stimulation as described herein may result in a greater response from a nearby nerve due to the activation of the electrodes on the first (e.g., top) side of the ribbon-shaped device, which may indicate that a nerve such as the spinal nerve root is on this side of the ribbon, or it may result in a greater response from a nerve when activating the electrodes on the second (e.g., back) side of the ribbon-shaped device, which may indicate that the nerve is closer to the other (back) side of the device. Occasionally, stimulation of the front and back sides of the device may not evoke a nerve response, or may evoke only an inconclusive response. However, it may be important to unambiguously determine which side of the ribbon-shaped device the nerve is located on, particularly when the position of the neural localization device may be used as a starting position for a tissue cutting/tissue modification device. In this case, confirmation of the nerve position relative to the starting position may confirm that the method will not result in cutting the nerve root and harming the patient. Thus, described herein are methods and systems for comparing the responses to stimulation from various separate regions or orientations of the neural localization device (e.g., front/back) to determine the relationship of a nerve (or nerves) relative to a pathway (the pathway of the neural localization device) through the body. The pathway typically extends around a target region. In some variations the methods may be considered as methods for determining if a nerve is between the target tissue (to be removed) and the pathway through the tissue and around the target tissue.

In operation, it may be beneficial to apply force to one or both ends of the device to push the device (and particularly one or more electrodes on the device) "down" (e.g., anteriorly towards the patient's front or ventral side/column). Urging the stimulation region of a ribbon-shaped neural localization device by pushing or pulling the ends may be used as part of any of the methods described herein, but may be particularly helpful when an ambiguous (or no) effect on the nerve is seen when stimulating to help evoke a response. For example, pushing both the distal and proximal end regions of the device when stimulating may help determine if a nerve is between the ribbon device and the target tissue, or if the device is on the opposite side of the ribbon-shaped device from the target tissue.

Also described herein are ribbon-shaped neural localization devices that expand when delivered in order to help determine nerve location. For example, in some variations the neural localization device may include an inflatable element (e.g., balloon) between the first and second elongate planar surfaces of the ribbon-shaped devices, at least in the stimulation region of the device. In some variations, one or both surfaces of the stimulation region correspond to the outer surface of a balloon. In operation, a device including an expandable neural stimulation region may be positioned within the body (e.g., within a spinal neural foramen) in an un-expanded configuration. Once positioned as desired, the device may be expanded (e.g., inflated) until mechanical stimulation of the nerve is achieved (e.g., measured by EMG, for example). The expansion/inflation may then be backed down or decreased until stimulation is eliminated. Thereafter, the device may be stimulated as described herein. For example, the electrode(s) on the top may be stimulated, then the electrodes on the bottom may be stimulated, and any resulting nerve stimulation (e.g., EMG response, direct neural stimulation recordings, etc.) compared to determine if the nerve (e.g., nerve root) is above or below the device.

As described above, the neuro localization/neuro localization devices described herein may be stimulated in any manner appropriate to determine which side of the ribbon-shaped device the nerve or nerves are located. In general the methods include comparing any stimulation evoked on a nerve by stimulating the "top" of the device with any stimulation evoked by stimulating the electrode(s) on the "bottom" of the device. The stimulation may include a ramp, step or other stimulation protocol sufficient to evoke a neural response when a nerve or nerve root is sufficiently close to the device. Examples of such stimulation techniques are described herein. In general, stimulation may mean stimulation to evoke a threshold response from the nerve (e.g., the minimum power required to evoke an EMG response).

In some variations, stimulation from the top and/or bottom of the devices, e.g., by energizing the electrode(s) on the first (top) and second (bottom) surfaces, may not result in a neural response, even when a ramp or range of stimulation intensities are used. To prevent damaging the tissue, the applied stimulation may be kept low (e.g., less than 100 mA, less than 50 mA, less than 30 mA, etc.). In general, it may be desirable to stimulate and confirm that the nerve is on one or the other side of the pathway taken by the device through the tissue by: either pushing or pulling the device from one or both ends (e.g. proximal or distal ends) to urge it towards or away from the target tissue; and/or by changing he polarity of the stimulation; and/or by changing the manner of stimulation. The manner of stimulation may be changed by changing from bipolar to monopolar stimulation. In some variations the manner of stimulation may be changed by changing from simultaneous multipolar (e.g., simultaneous stimulation of multiple electrode connected to a common source, including multiple anodes and multiple cathodes) to sequential multipolar stimulation (e.g., sequentially stimulating each bipolar pair on the same stimulation region). This may allow a greater current density from each bipole pair (or from each monopole, in monopolar configurations), in neural localization devices configured to allow sequential stimulation.

The process of determining which side of the ribbon-shaped neural localization device a nerve is on may include steps of serially altering any of these stimulation parameters. For example, in one variation the method of determining or checking which side of a ribbon-shaped, or substantially flat, neural localization (neuro localization) device a nerve or nerve root is on may start by inserting the device into position, then applying energy to stimulate the upper (e.g. top or first surface) electrode(s) in the neural stimulation region of the device, then applying energy to stimulate one or more electrode(s) in the lower (e.g., bottom or second surface) stimulation region. If a significant signal is not detected indicating stimulation of a nerve or nerve root (e.g., by EMG, muscle twitch, etc.), using this initial method, the stimulation parameters may be changed. For example, the neural localization device may be urged away from the target tissue (towards the anterior or ventral aspect of the subject) by pushing on the proximal and distal end regions of the neural localization device (or by holding one end fixed and pushing the opposite end), and the stimulation is applied to the top and then the bottom. If the results of this stimulation are again inconclusive, then another parameter may be changed. For example, the device may be pushed and/or pulled toward the target tissue. In some variations, stimulation may be switched from bipolar to monopolar. This may be achieved by either allowing one pole of a bipolar pair to 'float'(electrically) or by electrically connecting both poles and using a ground pad or pin in the patient. In some variations the device is adapted to allow switching between bipolar and monopolar application of energy. Again, if this does not produce a definite or distinguishing result, another parameter may be changed. For example, the poles of the device may be switched (e.g., by switching from anodal to cathodal stimulation). These different parameters may be changed either individually or in combination. For example, the device may be urged against the tissue by pushing or pulling both the distal and proximal end regions for both bipolar and/or monopolar stimulation.

In general, the systems for treating spinal stenosis may include a guidewire, a removable distal handle for a guidewire, a probe for inserting a guidewire around a target tissue, a tissue modification device for coupling to the proximal end of a guidewire and a neural localization device for coupling to the proximal end of a guidewire. The tissue modification device, neural localization device, and probe devices may be similarly adapted for use as a system, and in particular may be adapted to indicate the orientation of the devices and to prevent rotation of the devices during operation. For example, these devices may include a handle having a front and back that are marked.

In some variations, the neural localization devices described herein may be used to sense neural tissue via electrical impedance. Thus, the neural localization devices described herein may include a flexible body supporting one or more electrodes, where the electrodes are configured to receive as well as apply an electrical signal to and from the target tissue. The signal may be a non-stimulating electrical output and may characterize the tissue (target and non-target) using electrical bio-impedance. Electrical bio-impedance is the response of living tissues to externally applied electrical current. Bio-impedance measurements are carried out while "sweeping" a frequency of the applied electrical signal. During these measurements, the electrodes may be static or may propagate through the body. Alternatively, the device may include a series of electrodes which are activated sequentially along the length of the device. The measured bio-impedance components (resistance, capacitance, phase, etc.) are frequency-dependent thus characterizing the tissue or tissue(s) interacting with the device and electrodes. Analysis of the measured parameters enables determining what type of tissue (for example, whether a nerve) is nearby a device or portion of a device. The analysis may be performed in real time.

The impedance (i.e., complex impedance) of the tissue may be calculated at different frequencies and/or along a predetermined path of the device (e.g. moving a single electrode pair along a path or activating a serried of electrode pairs along a length of the device) and the body tissue type may be identified. The measured impedance may be continuously compared with an impedance data (e.g. known impedance values for blood, muscle, nerve, etc.).

In some variations, the electrodes may be configured to vary the size of the exposed electrode surface, the position of the electrode(s), including the distance of the electrode(s) from the edges of the NLR device, and/or the spacing between electrodes (including the spacing between electrodes in bipolar or other multi-polar configurations). The power (e.g., current or voltage) applied may also be regulated or limited to control the broadcast field.

Also described herein is a method of increasing foraminal height by removing primarily boney tissue on the inferior edge of a pedicle, cephalad to a targeted nerve root. In some embodiments, a method for increasing foraminal height includes the steps of advancing a tissue access instrument into a patient and toward a target tissue from a first location, around at least part of the target tissue, and out of the patient from a second location, so that both ends of the tissue access instrument are external to the patient, wherein the target tissue is an edge of a pedicle; positioning a tissue modification device adjacent to the edge of a pedicle using the tissue access instrument; and modifying the edge of a pedicle with the tissue modification device by moving the tissue modification device against the tissue.

In some embodiments, a method for increasing foraminal height in a patient's spine includes the steps of advancing a wire into the patient from a first location, through a neural foramen, around an edge of a pedicle of the spine, and out of the patient from a second location; connecting a tissue modification device to the wire; positioning the tissue modification device through the neural foramen and around the edge of the pedicle using the wire; and modifying tissue in the spine by moving the tissue modification device against the tissue.

Also described herein are bimanually controlled neural localization devices capable of determining if a nerve is nearby a region of the device. In some embodiments, the device includes a flexible elongate body, a stimulation region on the elongate body, and a guidewire coupler at the distal end region of the elongate body. The guidewire coupler is configured such that the elongate body is removably attachable to a proximal end region of a guidewire such that the stimulation region can be pulled into position by pulling on the guidewire while the proximal end region of the guidewire is held stationary by the guidewire coupler with respect to the distal end region of the elongate body.

In some embodiments, the bimanual neural localization devices include a flexible elongate body, a first stimulation region on the elongate body that is configured to emit a stimulation field in a first direction from the elongate body and a second stimulation region on the elongate body that is configured to emit a stimulation field in a second direction from the elongate body. The second direction is different than the first direction. The device may also include a flexible guide at the distal end of the elongate body that has a sharp distal end for penetrating tissue and is configured such that the stimulation region can be pulled into position by pulling on the guide. This variation may not need to couple to a separate guidewire, as the flexible guide region may act as an integral guidewire similar to the detachably coupling guidewires also described herein.

In some embodiments, the device includes a flexible elongate body including a proximal end configured to extend out of a first portion of a patient's body for manipulation of the proximal end, a distal flexible guide region configured to extend from a second portion of the patient's body for manipulation of the distal end, and a stimulation region between the proximal end and distal flexible guide region. The distal flexible guide region has a sharp distal end for penetrating tissue and is configured such that the stimulation region can be pulled into position by pulling on the distal flexible guide region. In some embodiments, the distal flexible guide region has a free length of at least 3 inches, while in some embodiments, the distal flexible guide region has a free length of at least 10 inches. The proximal end of the device may be at least 5 inches, at least 10 inches, at least 15 inches, or any length appropriate for allowing the device to be manipulated proximally when extending from the patient when the stimulation region is positioned near the target tissue.

In some embodiments, the flexible elongate body has an axial length, a width and a thickness, wherein the axial length is greater than the width, and the width is greater than the thickness. In some embodiments, the flexible elongate body is ribbon shaped having a first side and a second side, wherein the first and second sides are substantially parallel. The stimulation region may be on the first side of the elongate body and may be configured to emit a stimulation field along at least a portion of the length of the first side of the elongate body. In embodiments including a second stimulation region, it may be on the second side of the elongate body and may be configured to emit a stimulation field along at least a portion of the length of the second side of the elongate body.

In some embodiments, the stimulation region includes a stimulation electrode that is configured to emit a stimulation field. In some embodiments, the electrode is a proud electrode. In some embodiments, the stimulation region includes a pair of bipolar electrodes or a bipolar network, wherein the bipolar network comprises an anode and a cathode configured to form a bipolar stimulation field. The bipolar network may a plurality of anodes and a plurality of cathodes, wherein the plurality of anodes and the plurality of cathodes are configured to form an effectively continuous bipole field along a portion of the flexible elongate body. The plurality of anodes may be in electrical communication with a first anodal conductor, while the plurality of cathodes may be in electrical communication with a first cathodal conductor.

In some embodiments, the elongate body further includes an insulation element disposed along the length of the stimulation region configured to insulate a first portion of the stimulation region from a second portion of the stimulation region.

In some embodiments, the device further includes a proximal handle, coupled to the elongate body, having a control for selecting activation of either a stimulation field in a first direction (e.g. on the first side of the device) from the elongate body or a stimulation field in a second direction (e.g. from the second side of the device) from the elongate body.

In some embodiments, the device further includes radio-opaque markers distributed along the length of the elongate body. For example, the device may include a radio-opaque marker on the elongate body distal to the stimulation region and a radio-opaque marker proximal to the stimulation region, such that the proximal and distal radio-opaque markers delineate the stimulation region. In some embodiments, the radio-opaque marker comprises a ring coil, while alternatively, the radio-opaque marker comprises a hole defined by the elongate body.

Also described herein are systems capable of determining if a nerve is nearby a region of a device. In some embodiments, the system includes a bimanually controlled neural localization device and a guidewire. As described above, the device may include a flexible elongate body, a stimulation region on the elongate body, and a guidewire coupler at the distal end region of the elongate body. The guidewire may be configured to removably couple to the guidewire coupler of the neural localization device such that the stimulation region can be pulled into position by pulling on the guidewire while the proximal end region of the guidewire is held stationary by the guidewire coupler with respect to the distal end region of the elongate body.

In some embodiments, the system may also include a distal handle configured to couple to the distal end of the guidewire such that the stimulation region can be pulled into position by pulling on distal handle thereby pulling on the guidewire and/or a proximal handle configured to couple to the proximal end of the elongate body such that the stimulation region can be pulled into position by using at least one of the distal handle and the proximal handle.

In some embodiments, the guidewire coupler is configured to couple to a guidewire such that the stimulation region may be positioned using the guidewire without the guidewire disengaging from the guidewire coupler.

Also described herein are methods of determining if a nerve is nearby a region of a bimanually controlled device. In some embodiments, the method includes the steps of passing a distal end of a neural localization device in a first direction toward a target tissue, at least partially around a target tissue, and away from the target tissue, such that a stimulation region on the neural localization device is positioned adjacent to the target tissue; energizing the stimulation region to emit a stimulation field from the elongate body; and determining if a nerve has been stimulated by the emitted field.

In some embodiments, the method may include the steps of passing a distal tip of a guidewire into a patient, around a target tissue, and out of the patient so that proximal and distal ends of the guidewire extend from the patient; coupling the distal end of a neural localization device to the proximal end region of the guidewire such that the proximal end region of the guidewire is held stationary with respect to the distal end of a neural localization device; pulling the neural localization device into position within the patient using the guidewire; energizing a stimulation region of the device to emit a stimulation field; and determining if a nerve has been stimulated by the emitted field. The guidewire (or guide portions of some devices may be passed around the target tissue at an angle, so that the pathway is curved).

In some embodiments, the step of passing distal end of a neural localization device comprises passing a guidewire in a first direction toward a target tissue (e.g. tissue within a spinal foramen), at least partially around a target tissue, and away from the target tissue and pulling the stimulation region on the neural localization device adjacent to the target tissue using the guidewire. The step of passing the distal end of a neural localization device may also include applying tension to both the proximal end and the distal end of the neural localization device. In some embodiments, the method may further include the step of coupling a flexible tissue-modification device to the guidewire.

In some embodiments, the method may further include the steps of passing a flexible tissue-modification device in a first direction toward a target tissue and at least partially around a target tissue, such that a tissue modification region of the device is positioned adjacent to the target tissue, wherein the flexible tissue-modification device comprises a flexible elongate body having the tissue modification region including at least one tissue modifying element oriented in the same direction as stimulation region of the ribbon neural localization device; and urging the tissue modification region against the target tissue by pulling the tissue-modification device from at least one end of the device.

In some embodiments, the determining step further includes determining a first threshold stimulation amount from the first stimulation region to elicit an EMG response and a second threshold stimulation amount from the second stimulation region to elicit an EMG response. The method may then further include the step of comparing the first threshold stimulation amount to the second threshold stimulation amount. In some embodiments, the determining step further includes determining if a nerve is present between the flexible neural localization device and the target tissue.

In some embodiments, the pulling step further includes pulling the neural localization device into position within the patient using a distal handle coupled to the guidewire and/or pulling the neural localization device into position within the patient using at least one of the distal handle and a proximal handle coupled to the neural localization device. In some embodiments, the pulling step further includes pulling the neural localization device into position within the patient using the guidewire without disengaging the guidewire from the neural localization device.

Also described herein is a method of determining if a nerve is nearby a region of a device that includes the steps of passing a flexible distal end of a neural localization device having a stimulation region into a patient, around a target tissue, and out of the patient so that proximal and distal ends of the neural localization device extend from the patient and the stimulation region is adjacent to the target tissue; pulling on one or both of the proximal and distal ends of the neural localization device to move the stimulation region closer to the target tissue; energizing the stimulation region to emit a stimulation field in a first direction from the elongate body, wherein the first direction is toward the target tissue; pushing on one or both of the proximal and distal ends of the neural localization device to move the stimulation region away from the target tissue; energizing the stimulation region to emit a stimulation field in a second direction from the elongate body, wherein the second direction is away the target tissue; and determining the position of the nerve with respect to the elongate body.

In some embodiments, the pulling step may further include pulling on one or both of the proximal and distal ends of the neural localization device to move the stimulation region closer to the target tissue without disengaging the guidewire from the neural localization device, while the pushing step may further include pushing on one or both of the proximal and distal ends of the neural localization device to move the stimulation region away from the target tissue without disengaging the guidewire from the neural localization device. As mentioned, the coupling between the guidewire and the neural localization device may be configured so that the guidewire and neural localization device may be disengaged but may remain secure when axially pushing or pulling the neural localization device and guidewire relative to each other. For example, the guidewire and neural localization device may be configured so that the two are decoupled by rotating and/or bending the guidewire and neural localization device at their coupling region (e.g., relative to the long axis of the neural localization device).

Also described herein are methods of determining if a nerve is nearby a region of a device that includes the steps of positioning a stimulation region of a neural localization device along a curved path such that the stimulation region is adjacent to a nerve; moving the stimulation region off of the curved path and toward the nerve; energizing the stimulation region to emit a stimulation field in a first direction from the neural localization device, wherein the first direction is toward the nerve; moving the stimulation region off of the curved path and away from the nerve; energizing the stimulation region to emit a stimulation field in a second direction from the neural localization device, wherein the second direction is away the nerve; and determining the position of the nerve with respect to the neural localization device.

In some embodiments, the moving steps may further include pushing a distal portion of the neural localization device by pushing a tube device against the distal portion of the neural localization device. The pushing step may also include advancing the tube device along the distal end of the neural localization device toward a distal end of the stimulation region of the neural localization device. In some embodiments, the moving steps may further include moving the stimulation region steps further comprising moving the stimulation region of the elongate body using at least one of the proximal and distal ends of the neural localization device.

Also described herein are methods of determining if a nerve is nearby a region of a device that includes the steps of advancing a flexible elongate body of a neural localization device into a patient and around a target tissue; energizing a stimulation region of the elongate body to emit a stimulation field in a first direction from the elongate body; determining a first threshold amount of energy required to stimulate a measurable response from neural tissue with the stimulation field in the first direction; energizing a stimulation region of the elongate body to emit a stimulation field in a second direction from the elongate body, wherein the second direction is different from the first direction; determining a second threshold amount of energy required to stimulate a measurable response from neural tissue with the stimulation field in the second direction; and applying a ratio of the first threshold and the second threshold, and a magnitude of one of the first threshold and the second threshold to determine if the nerve is in the first direction from the elongate body or in the second direction from the elongate body.

In some embodiments, the energizing steps further include energizing a stimulation region of the elongate body until an EMG response is elicited. In some embodiments, the method further includes the step of removing tissue from the intervertebral foramen when the first threshold is less than 5 mA and the ratio is greater than or equal to 4, when the first threshold is greater than or equal to 5 mA and the ratio is greater than or equal to 2, when the first threshold is greater than or equal to 10 mA and the ratio is greater than or equal to 1.5, and/or when the first threshold is greater than or equal to 25 mA and the ratio is greater than or equal to 1.3.

In particular, described herein are methods of positioning a neural localization device to determine if a nerve is nearby, the method comprising: passing a neural localization device along a first pathway; energizing a first stimulation region of the neural localization device to emit a stimulation field in a first stimulation direction from the neural localization device while passing the neural localization device; determining a threshold stimulation location along the pathway, wherein the threshold stimulation location corresponds to the position along the pathway having the lowest stimulation level emitted in the first stimulation direction that evokes a response from a target neural tissue; positioning the neural localization device at the threshold stimulation location; determining a threshold stimulation level in a second stimulation direction from the neural localization device while the neural localization device is at the threshold stimulation location; and comparing the stimulation level emitted in the first stimulation direction at the threshold stimulation location to the threshold stimulation level in the second stimulation direction to determine if the target neural tissue is in the first stimulation direction or in the second stimulation direction.

In some variations, the method also includes coupling the neural localization device to a guidewire. The neural localization device may be passed along the first pathway by pulling a distal end of the neural localization device.

In some variations, passing the neural localization device comprises orienting the neural localization device so that the first stimulation direction points approximately dorsally or approximately ventrally relative to the patient and the second stimulation direction points in the opposite direction, approximately ventrally or approximately dorsally, relative to the patient. The neural localization device may be oriented (e.g., have a top surface opposite a bottom surface), and may be positioned within the patient's body so that one side is kept oriented generally dorsally relative to the patient with the opposite side generally ventrally. As used herein, the phrase "generally dorsally" may be used to mean that one face of the neural localization device (and particularly the region configured to emit stimulation on the device) looking dorsally. For example, when the neural localization device has a ribbon-shaped body, the upper surface of the ribbon shaped body may face generally dorsally and the bottom (opposite) surface may face generally ventrally as the device is moved through the body near (and around) the target tissue. The device may pass through the patient in a curved or arced pathway (from the patients back or side, around the target tissue and back up toward the patient's back). Even though the surface of the neural localization device may change orientation (e.g., facing more laterally than just dorsally or more laterally than just ventrally) the overall direction may be dorsal or ventral even when oriented at an acute angle with respect to the dorsal or ventral direction.

Any of the neural localization devices described herein may be used. For example, the step of passing the neural localization device may comprise passing a neural localization device having a flexible ribbon-shaped body having a first set of electrodes on one face of the ribbon-shaped body and a second set of electrode on an opposite face of the ribbon-shaped body.

In some variations, passing a neural localization device along the first pathway comprises passing a guidewire along the first pathway before passing the neural localization device.

The step of energizing the first stimulation region may comprise applying stimulation at a plurality of stimulation levels. For example, energizing the first stimulation region may comprise applying a ramp of current having a plurality of stimulation levels. Alternatively, in some variations, a random distribution of stimluation levels (as opposed to a smooth ramp or step ramp) may be applied.

The step of determining a threshold stimulation location along the pathway may comprise moving the neural localization device forward and backward along the pathway while emitting the stimulation field in the first stimulation direction. Determining a threshold stimulation location along the pathway may also comprise evoking an EMG response. Alternatively, in some variations, an evoked response may be a muscle twitch, increase (or decrease) in action potentials, limb movement, or the like. The step of determining a threshold stimulation location along the pathway may comprise determining the minimum stimulation emitted in the first stimulation direction that evokes a response from a target neural tissue.

The step of positioning the neural localization device at the threshold stimulation location may comprise anchoring the neural localization device in position.

In some variations, the step of determining the threshold stimulation level in the second stimulation direction from the neural localization device may comprise increasing the current applied from the second stimulation direction until a response is detected. As mentioned above, the step of determining the threshold stimulation level in the second stimulation direction may comprise evoking an EMG response.

The step of comparing the stimulation level emitted in the first stimulation direction to the threshold stimulation level in the second stimulation direction may comprise comparing the minimum stimulation level required to evoke a response that is emitted in the first stimulation direction at the threshold stimulation direction to the threshold stimulation level emitted in the second stimulation direction.

In general, any of these methods may include the step of indicating if the target neural tissue is located in the first stimulation direction or in the second stimulation direction relative to the neural localization device. For example, the method may include the step of indicating (by visual, audible, tactile, or otherwise) that the nerve is above or below the device (e.g., located dorsally or ventrally of the device). Thus, the method may indicate if a nerve is above or below the device pathway, and could potentially be damaged by a tissue modification device positioned along the pathway. In some variations if the method indicates that neural tissue is not present between the target tissue and the pathway though the tissue, then the tissue modification device may be positioned along the pathway.

Also described herein are methods of positioning a neural localization device along a pathway through the tissue near a target tissue and near adjacent neural tissue. This method may be used as just described to determine if neural tissue is between the target tissue and the path through the tissue. For example, described herein is a method of positioning a neural localization device, the method comprising: passing a distal tip of a guidewire into a patient, around a target tissue adjacent to a neural tissue, and out of the patient so that proximal and distal ends of the guidewire extend from the patient; coupling the distal end of a neural localization device to the proximal end region of the guidewire; pulling the neural localization device into the patient using the guidewire to pass the neural tissue; emitting a stimulation field in a first direction from the neural localization device while passing the neural localization device near the neural tissue; determining, at a plurality of locations, a minimum stimulation level that evokes a response from the neural tissue when emitting a stimulation field in the first direction while passing the neural localization device near the neural tissue; and positioning the neural localization device at a location where a lowest minimum stimulation level was determined.

The method may also include the steps of determining, at the location where the lowest minimum stimulation level was determined, a minimum stimulation level that evokes a response from the neural tissue when emitting a stimulation field in a second direction. The method may also include comprising comparing the lowest minimum stimulation level that evokes a response from the neural tissue when emitting a stimulation field in the first direction with the minimum stimulation level that evokes a response from the neural tissue when emitting a stimulation field in the second direction.

As mentioned above, the method may include the step of emitting a stimulation field in a first direction from the neural localization device comprising emitting a plurality of stimulation levels, such as a ramp, step, etc.

The step of coupling the device to a guidewire may comprise coupling a neural localization device having a flexible ribbon-shaped body with a first set of electrodes on one face of the ribbon-shaped body and a second set of electrode on an opposite face of the ribbon-shaped body to the proximal end region of the guidewire. The step of coupling may also comprise coupling the distal and of the neural localization device to the proximal end region of the guidewire such that the proximal end region of the guidewire is held stationary with respect to the distal end of a neural localization device.

Pulling the neural localization device into the patient may include orienting the neural localization device so that the first direction from the neural localization device is oriented approximately dorsally or approximately ventrally relative to the patient.

The step of emitting the stimulation field in a first direction from the neural localization device may include emitting the stimulation field from one side of the neural localization device. In some variations emitting a stimulation field comprises applying current at a plurality of different current levels.

In another variation of this method, described herein are methods of positioning a neural localization device to determine a location of a nerve relative to a device, the method comprising: passing a distal end of a neural localization device in a first direction; energizing a first stimulation region of the neural localization device to emit a stimulation field in a first stimulation direction from the neural localization device while passing the neural localization device in the first direction, wherein the stimulation field includes a plurality of stimulation levels; determining, at a plurality of locations, a minimum stimulation level that evokes a response from the target neural tissue while passing the neural localization device in the first direction; positioning the neural localization device in the location where the lowest minimum stimulation level was determined; energizing a second stimulation region of the neural localization device to emit a stimulation field in a second stimulation direction from the neural localization device while the neural localization device is in the location where the lowest minimum stimulation level was determined; determining a minimum stimulation level that evokes a response from the target neural tissue from the second stimulation region; and comparing the lowest minimum stimulation level from the first stimulation region to the minimum stimulation level from the second stimulation region to determine if the target neural tissue is in the first stimulation direction or in the second stimulation direction.

BRIEF DESCRIPTION OF THE DRAWINGS

FIGS. 1A-1F illustrate one variation of an NLR device as described herein. FIG. 1A shows a perspective view of this NLR device, and FIG. 1B show a cross-section through the device shown in FIG. 1A. FIG. 1C shows a partial cross-section through another variation of an NLR device. FIG. 1D shows a partial top view of the device shown in FIG. 1C. FIGS. 1E and 1F illustrate proud electrodes formed as part of an NLR device.

FIG. 2A shows a top view, FIG. 2B shows an expanded view of one region of the device of FIG. 2A, and FIG. 2C shows a slightly expanded view of yet another variation of the device shown in FIG. 2A.

FIGS. 4A and 4B show a monopolar variation of a device including a plurality of electrodes on each side (top and bottom) of the NLR device.

FIG. 5A shows a schematic cross-section through one variation of a device having proud (protruding) electrodes.

FIGS. 5B and 5C illustrate switching the polarity of electrodes in an NLR device.

FIGS. 6A-6E illustrate various configurations of bipolar NLR devices.

FIG. 6F illustrates a configuration of bipolar NLR devices having a shield.

FIG. 11A shows an NLR device having a round cross-section; FIG. 11B shows a flattened (e.g., crushed) extrusion similar to that in FIG. 11A. FIG. 11C illustrates an NLR device having an oval or ribbon-shaped cross-section.

FIGS. 22B-23F illustrate various methods of securing (e.g., locking or releasably locking) guidewire connectors as described herein.

FIGS. 31C and 32A-32C illustrate various details of the neural localization device of FIG. 31A.

FIGS. 34A and 34B illustrate different ways that the NLR devices described herein may be inserted within the spine as part of a spinal decompression procedure.

FIG. 35 is one embodiment of an NLR device.

FIGS. 36A-36C illustrate the application of force to push or pull an NLR device within a spinal foramen to control the position of the NLR within the foramen.

FIG. 43 is a distal guidewire coupler that may be used to couple to a guidewire and allow the guidewire to push and/or pull the device into position.

FIG. 44 shows another enlarged view of the distal end of an NLR device having three pairs of electrodes on each of the top and bottom surfaces.

FIG. 45 is an enlarged view of the stimulation region of FIG. 44.

FIG. 46 shows a cross-sectional view through the insulating tubing of the stimulation region for a device such as the one shown in FIG. 35.

FIG. 51 shows three graphs representing measured tissue impedance as a function of frequency, for three different tissues respectively. FIG. 52 illustrates an electric current as a function of the depth (i.e. length of device) including different tissue layers, for measured (A1) and modeled (A2) data; FIG. 53 illustrates the transition between different tissue layers having different impedance characteristics, illustrated by a change in the impedance measurement as a function of depth (i.e. length of device).

DETAILED DESCRIPTION

Figure 1D:
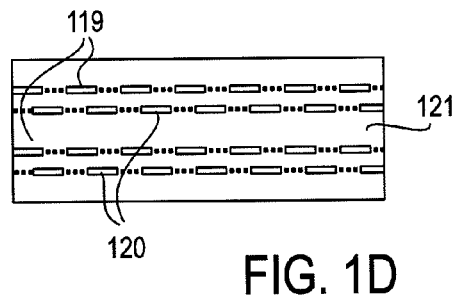

Described herein are devices, systems and methods for determining the location of a nerve or neural tissue relative to a pathway through a patient passing near, around or adjacent to a target tissue. In particular, described herein are flexible neural localization devices that may be ribbon-shaped, for use in tortuous and difficult-to-reach body regions, such as the neural foramen of the spine. In general, these devices may be referred to as neural localization ribbon devices, NLR devices, neural localization devices, or neuro localization devices. These devices are generally useful for determining if a nerve is nearby a surface of the device. In some variations, the devices may determine which side of the device a nerve is on (e.g., 'above' or 'below' the flat surface of the device, relative to the patient) or if a nerve is located between a pathway through the tissue taken by the device and the target tissue. The devices generally include a flexible elongate body having a stimulation region. The stimulation region may include an electrode or a series of electrodes. These electrodes may be arranged as bipoles, monopoles, tripoles, or the like, but are generally configured so that the stimulation field or broadcast field emitted by the electrodes is limited to regions immediately adjacent to the device, so that they detect (e.g., by stimulating) nerves only in a particular orientation relative to the neural localization device. For example, the electrodes may be arranged as bipoles (that can also be referred to as tight bipoles), and may include a cathode and an anode that are spaced relatively close together to form a limited broadcast field. The broadcast field may be referred to as the bipole field, or the field formed by the excitation of the bipole pair. In general, the bipole filed is a controlled or "tight" broadcast field that extends from the bipole pair(s). Similarly, the broadcast field from monopolar, and particularly tripolar, quadrapolar, etc. electrodes may also be limited. Limiting the broadcast field in this manner may avoid the (undesirable) detection of nerves adjacent to other regions or surfaces of the neural localization device. This is illustrated in U.S. Ser. No. 12/060,229, previously incorporated by reference.

The tight broadcast field emitted by the electrode(s) described herein may be limited so that it stimulates nerves only within a predetermined distance. This distance is typically quite narrow (e.g., within about 2 mm, within about 1 mm, within about 0.5 mm, within about 0.1 mm, within about 0.05 mm, etc. of the surface of the NLR device). Beyond this broadcast range, the current or voltage applied by the device falls below levels sufficient to stimulate the nerve. The broadcast field may be controlled by the combination of the power supplied to the stimulation electrode(s) as well as the configuration of the electrode(s) on the NLR device.

In particular, the NLR electrodes may be configured as mutlipolar electrodes, including one or more anodes and one or more cathodes. By placing the anodes and cathodes relatively close to each other, the current flowing between the anodes and cathodes may be limited. In some variations a plurality of anodes and a plurality of cathodes may be arranged in a pattern along or across a surface (e.g., the top and/or bottom surface of the NLR device) to form a bipole network that permits a larger area of the NLR device to stimulate only nerves passing within a predetermined range of the surface. This sort of bipolar network may allow a relatively "flat" profile of broadcast field, so that although a large area of the NLR device may emit the broadcast field, the field does not penetrate deeply, preventing stimulation of nerves outside of the (typically narrow) range desired. These configurations may also prevent stimulation of nerves located on the opposite side(s) of the NLR device.

In some embodiments, as described in greater detail below, the electrodes may be configured to apply and receive an electrical signal to and from the target tissue. In this embodiment, the signal may be a non-stimulating electrical output and may characterize the tissue (target tissue and non-target tissue) using electrical bio-impedance. Electrical bio-impedance is the response of living tissues to externally applied electrical current. Bio-impedance measurements are carried out while "sweeping" a frequency of the applied electrical signal. During these measurements, the electrodes may be static or may be moved through the body. Alternatively, the device may include a series of electrodes which are activated sequentially along the length of the device. The measured bio-impedance components (resistance, capacitance, phase, etc.) are typically frequency-dependent, thus the use of multiple frequencies may help in characterizing the tissue or tissue(s) interacting with the device and electrodes. Real-time analysis of the measured parameters enable the system to determine what type of tissue (for example, whether a nerve) is nearby a device or portion of a device.

The elongate body region of an NLR device may also be referred to as a probe or probe body. In general, the NLR device may include one or more regions on the outer surface of the device that are configured to determine if a nerve is nearby the region (or one or more of the regions) of the device. In some variations, each region includes an electrode or a set of electrodes (e.g., a multi-polar network) that is arranged to emit energy to stimulate a nearby nerve so that it can be detected. The regions may be arranged around or along the outer surface of the device. In general the NLR devices described herein are flat, for example, including a first side (top) and a second side (bottom); the sides joining the top and bottom may be narrow (the more flat the structure, the more narrow), or they may have sufficient thickness for inclusion of one or more electrodes. Thus, each region may include one or more electrodes (e.g., bipole pairs or networks), which may be used to detect a nearby nerve.

FIG. 1A illustrates a top view of one variation of an NLR device coupled to a guidewire 109. In FIG. 1A, the device has a proximal end 101 that is configured to include or be attached to a proximal handle 103. The distal end 105 includes a coupler 107 for coupling to a guidewire 109. The coupler may therefore be referred to as a guidewire coupler. Near the distal end, but extending proximally; the body of the NLR is a flexible, ribbon-shaped structure, 111. This ribbon-shaped body region is typically flat or flattened, so that the top and bottom have a width that is much greater than the thickness between these surfaces. In this example, the top and bottom surfaces each include a set of multipolar electrodes. In FIG. 1A, the top shows a bipole network including a line of cathodes and a line of anodes, shown in more detail in FIGS. 1C and 1D.

FIG. 1B shows a cross-section through the ribbon region 111 of a device such as the one shown in FIG. 1A. In this exemplary cross-section, each side of the NLR device (the top, bottom and both sides) include a pair of electrodes forming part of a bipole network. Four separate networks are formed. As shown, there is a top electrode pair 112, a bottom electrode pair 113, and side electrode pairs 114. In FIG. 1B, the electrodes are set inward from the edges between the top and sides and bottom, which may help limit the spread of the emitted filed from one side (e.g., the top) to activate a nerve facing another side (e.g., the sides or bottom). In other variations, the thickness of the NLR device (the sides between the top and bottom) may be more narrow. In some variations, the device may include only a top stimulation region or may only include a top and bottom stimulation region. In some variations, the electrodes on the surface(s) may be part of a multi-polar network (e.g., having a plurality of cathodes and/or a plurality of anodes). For example, FIG. 1C shows a partial cross-section through another variation of an NLR device. As shown, on the bottom side of the device for example, the device includes two sets of anodal conductors 115 and 116 and two sets of cathodal conductors 117 and 118. The anodal conductors and cathodal conductors run along the length of the device for both the top and bottom surface of the device. As shown, on the top side of the device for example, the anodes and cathodes are exposed at discrete locations along the device to form individual electrodes (e.g. individual anodes and cathodses). For example, anode 119 is formed by an anodal conductor on the top surface and cathode 120 is formed by a cathodal conductor on the top surface. As shown, the anodal conductors and cathodal conductors are housed in an insulating material 121. The insulating material 121 is removed or has holes in discrete locations over the anodal conductors and cathodal conductors and along both the top and bottom surfaces of the device to form the electrodes (e.g. anodes and cathodes). The electrodes may be flush to the surface, or they may alternatively be below the surface of the insulator or may be proud with respect to the surface of the insulator. For example, the electrode may be formed by removing material (e.g., skiving) to expose a portion of the anodal or cathodal conductor or wire. The exposed wire regions may be filled or coated with a conductive material. In other variations, electrodes may be formed by laser ablating material to expose the wire and filling with a conductive material or bonding a flex circuit to them to form the electrode. Multiple electrodes may be formed from each wire.

These electrodes may be configured as a single network (including a quadrapolar network) spanning the surface, or they may be configured as two bipolar networks, or the like. FIG. 1D illustrates a top view of the same arrangement as shown in FIG. 1C. As shown in FIG. 1D, anodes 119 are the exposed regions of the anodal conductors that run along the length of the device, while the cathodes 120 are the exposed regions of the cathodal conductors that also run along the length of the device. The non-exposed portions of the two anodal conductors and two cathodal conductors are depicted as dotted lines as they are positioned below the insulating material 121.

Figure 1F:
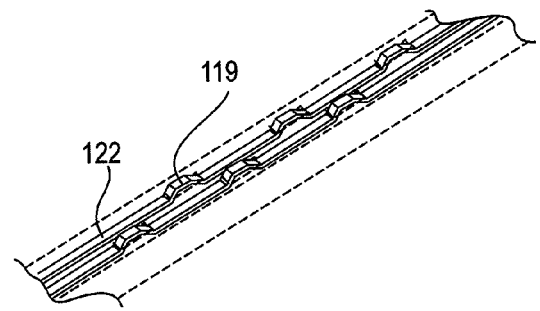

FIGS. 1E and 1F show detail of a series of proud electrodes exposed along the surface of the NLR device. In this example, as shown in FIG. 1F, each electrode 119 is formed by a bump or ridge in the conductor 122. The conductor, either anodal or cathodal, may include a series of bumps or ridges such that the conductor forms a number of electrodes in series. As shown in FIG. 1E, the bumps or ridges are exposed through a window or hole in the insulating material 121 to form discrete electrodes 119. The electrodes 119 formed by this method may preferably be proud with respect to the surface of the device or they may be flush with the insulating material 121 (e.g., non-proud).

In this example, the electrodes are formed by pairs of metal wires (e.g., an upper anode wire and an upper cathode wire for the top surface and a lower anode wire and a lower cathode wire for the bottom surface). Each wire is connected to or includes a plurality of electrodes; in this example, each wire includes to three electrodes that each individually extend "proud" from the surface of the ribbon-shaped device. In one particular embodiment, the electrodes are each 4 mm long, and extend 0.020" from the surface. The cathodal electrodes on each surface are staggered along the length of the NLR device with anodal electrodes, as illustrated. The "proud" electrode shown may afford a greater sensitivity than flush or recessed electrodes.

Figure 2A:
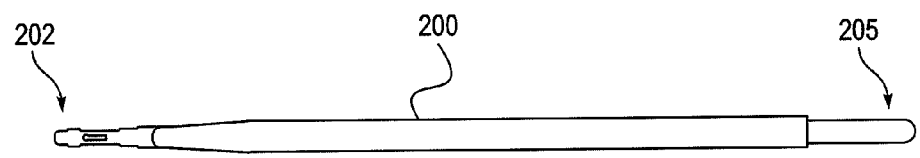
FIGS. 2A-2C illustrate another variations of an NLR device.
Figure 2B:
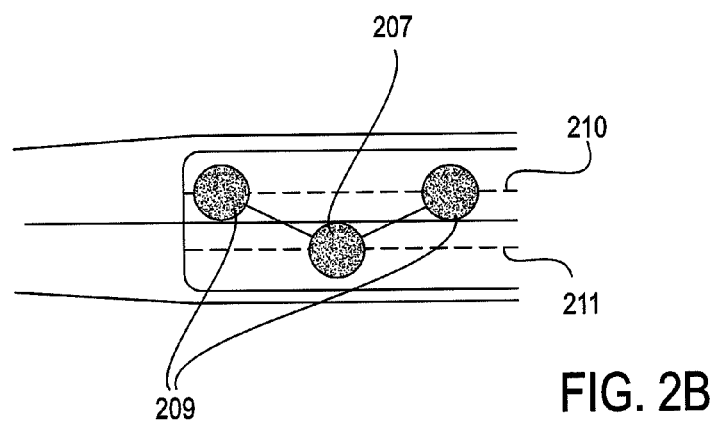
Figure 2C:
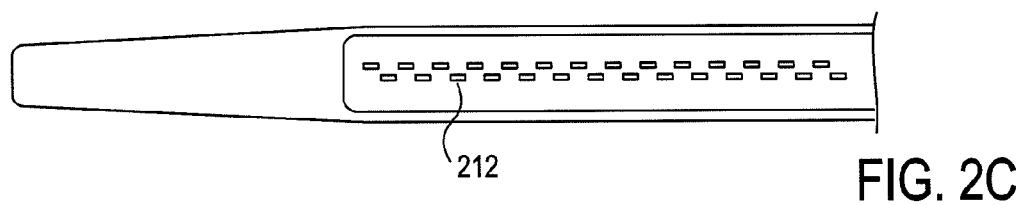
Figure 3A:
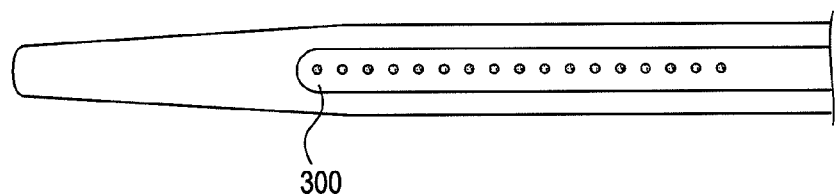
FIGS. 3A-3E illustrate different monopolar configurations of NLR devices.
Figure 3B:
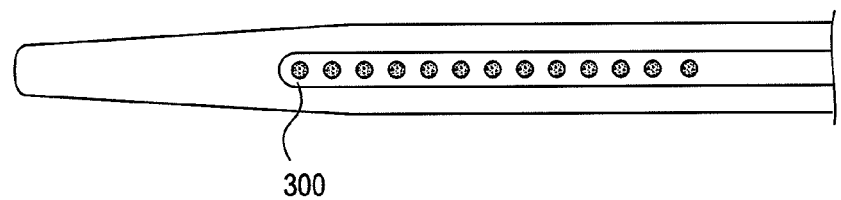
Figure 3C:
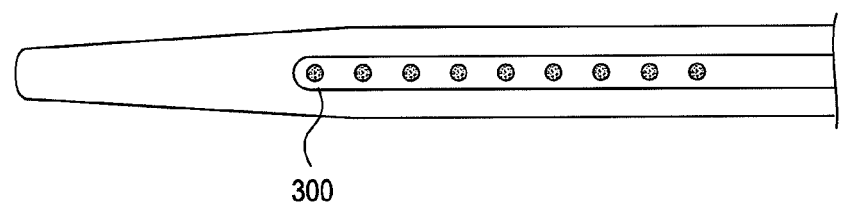
Figure 3D:
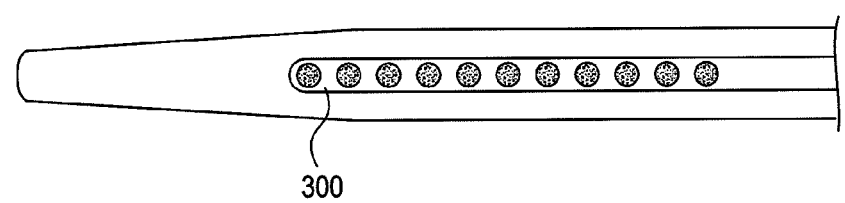
Figure 3E:
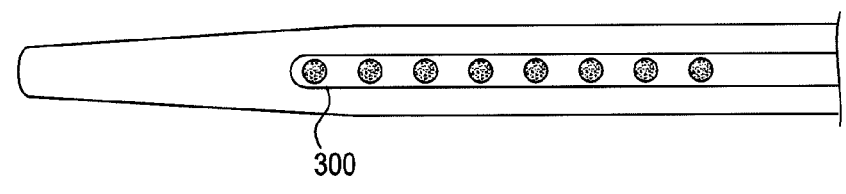

An alternative variation is shown in FIGS. 2A-2C. Similar to the devices shown in FIGS. 1A-1F, in FIG. 2A an NLR device includes an elongate body 200 having a distal end with a guidewire coupler 202 and a proximal end 205 that may be connected to a proximal handle.

In any of these variations, the flexible elongate body may be configured to be blunt (atraumatic). In general, the outer body (e.g. insulating material) of the device may be formed of any appropriate material, including polymeric materials such as PEBAX, PEEK or the like. Non-conducting and biocompatible materials may be particularly preferred. FIG. 2B illustrates a partial view of the electrodes forming the bipole network on the top surface of the device shown in FIG. 1A. In this example, the exposed electrodes alternate between anodal electrodes 209 (connected to a single anodal line 210) and cathodal electrodes 207 (connected to a single cathodal line 211). Exemplary sizes and arrangements for variations of these devices are illustrated in FIGS. 6A-6E. FIG. 2C illustrates another variation of an NLR device in which the exposed electrodes 212 are not round, but are oval.

In addition to the networks of multipolar electrodes described above, the NLR devices as taught herein may be configured as a network of (or of individual) monopolar electrodes 300, as illustrated in FIGS. 3A-3E. In this example, the NLR device may be used with a ground pad or stimulus return electrode coupled to the patient. The current evoked by the device may be 'spread' further with such monopolar devices.

FIGS. 4A and 4B show another variation of an NLR device having a plurality of monopolar electrodes extending along the length of each side (top and bottom) of an NLR device. In this variation the stimulation region on the top and bottom of the ribbon-shaped device may be formed from a flexible circuit, and thus, in this variation, the electrodes may not be "proud" (extending substantially from the surface of the device). As shown in FIGS. 4A and 4B, the device has a proximal end 401 that is configured to include or be attached to a proximal handle 403. The distal end 405 includes a coupler 407 for coupling to a guidewire (not shown). The coupler may therefore be referred to as a guidewire coupler. Near the distal end, but extending proximally, the body of the NLR is a flexible, ribbon-shaped structure, 411. This ribbon-shaped body region is typically flat or flattened, so that the top and bottom have a width that is much greater than the thickness between these surfaces. In this example, the top and bottom surfaces each include a set of monopolar electrodes 413.

FIG. 5A shows a schematic cross-section through one variation of the stimulation region of an NLR device. In this example, the NLR device includes an electrode 501 on the upper surface that is a "proud" electrode (extending from the upper surface of the ribbon). This electrode is configured as an cathode (negative) electrode. A proud anode (positive) electrode 503 is shown on the bottom of the device. In this embodiment, current may be applied in a bipolar fashion between the upper and lower electrodes, as illustrated in FIG. 5B. In this example, the stimulation is anodal stimulation. FIG. 5C illustrates the alternative configuration of cathodal stimulation. These figures also illustrate reversing the anode and cathode by changing the applied current to different electrodes. For example, merely switching the supplied power connection, it may be possible to switch the anode and cathode; alternatively the device (e.g., handle region) may include a switch for switching anode and cathode. In some variations it may be preferable to have the anodes and cathodes be arranged in a bipolar (or multipolar) set on the same side of the device to minimize the current spreading around the edges of the device.

FIGS. 5B and 5C also illustrate one method of determining which side a nerve is on by switching between anodal and cathodal stimulation. If it is known that a particular nerve or nerve root is more sensitive to anodal stimulation, the response of a nerve to both anodal and cathodal stimulation (by switching between the two as illustrated in FIGS. 5B and 5C) can be determined. For example, the threshold for evoking an EMG (or a robust EMG) may be determined for each configuration. If the nerve is more sensitive to anodal stimulation, then the nerve is likely to be below the device if the threshold for triggering an EMG in anodal stimulation is greater than the threshold for triggering an EMG in cathodal stimulation, and vice-versa.

Figure 6A:
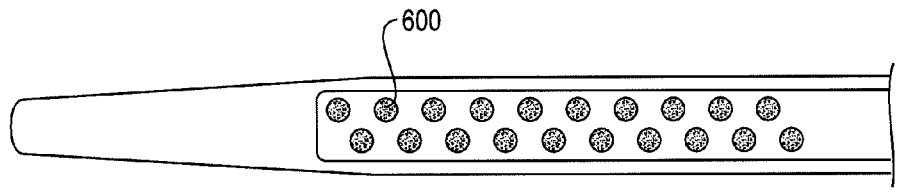
Figure 6B:
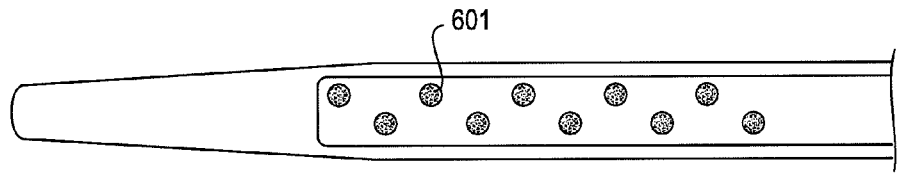
Figure 6C:
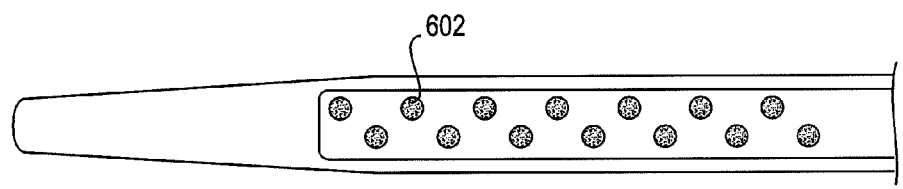
Figure 6D:
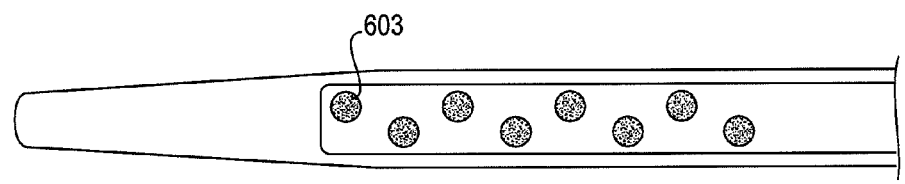
Figure 7A:
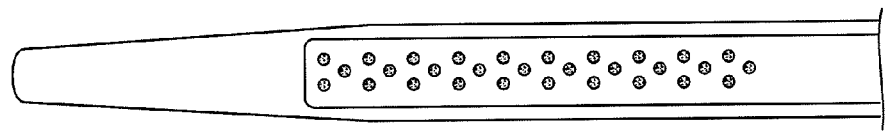
FIGS. 7A-7B illustrate various configurations of tripolar NLR devices.
Figure 7B:
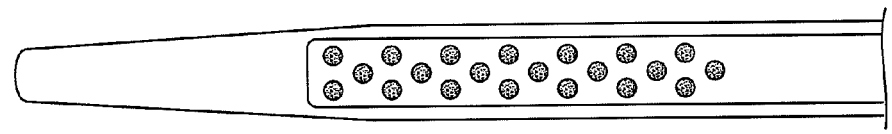
Figure 8A:
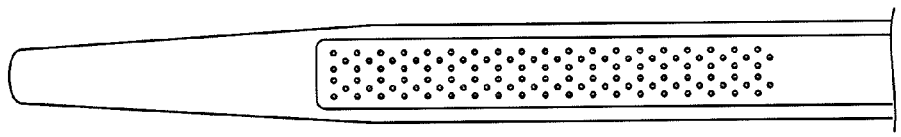
FIGS. 8A-8C illustrate various configurations of multipolar NLR device.
Figure 8B:
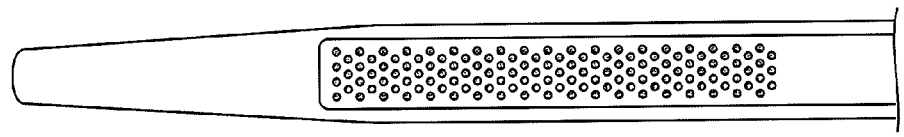
Figure 8C:
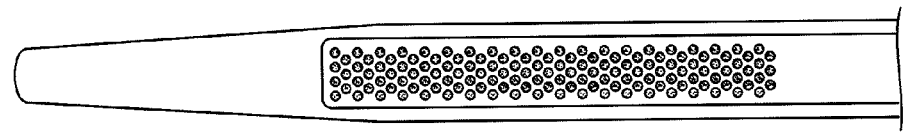

FIGS. 6A-6E illustrate other variations, similar to the arrangement shown in FIG. 2B, of a network of bipolar pairs (a bipole network). For example, FIG. 6A illustrates a bipole network on the top surface of the NLR device (within an activation range that extends longitudinally along the NLR device) in which the exposed electrodes 600 are round, and are 1 mm in diameter, and spaced 1 mm apart. In any of the variations described herein, the exposed electrodes may be any appropriate shape, including round, square, oval, etc. FIGS. 6B-6D illustrate other geometries of bipolar electrodes, including electrodes 601 that are 1 mm diameter and spaced 2 mm apart (FIG. 6B), electrodes 602 that are 1.5 mm diameter and spaced 1 mm apart (FIG. 6C), and electrodes 603 that are 1.5 mm in diameter and spaced 2 mm apart (FIG. 6D). FIG. 6E illustrates bipolar electrodes that are exposed along the length of (or exposed along a portion of the length of) the NLR device. In this embodiment, the device includes a single elongate anode 604 and a single elongate cathode 605 that are disposed along the length of the stimulation region of the NLR device. Other variations of electrodes and electrode arrangements are contemplated, including smaller or larger electrodes and smaller or larger separations. In addition, the electrodes shown are arranged in lines corresponding to the underlying anodal or cathodal lines (wires, etc.—not shown). This arrangement may vary, and may span curves, arcs, sinusoids, or the like, extending either longitudinally along the NLR, diagonally across the NLR, or perpendicular to the longitudinal access.

As mentioned above, a bipole pair forming part of a multipolar network may include an anode and a cathode and may have a very limited broadcast field (e.g., a 'tight bipole pair'). In some variations the size of the anode and cathode forming the bipole pair are relatively small, particularly (e.g., less than 5 mm$^2$, less than 3 mm$^2$, less than 2 mm$^2$, less than 1 mm$^2$), and the anode and cathode are positioned sufficiently nearby so that the majority of current passes between the anodes and cathodes. For example, the anode and cathode of a bipole pair may be separated by less than 5 mm, less than 2 mm, less than 1 mm, etc.

As mentioned above, an NLR device may include multiple electrode networks. For example, different regions on the surface of the device may include different electrode networks (e.g., each region may have its own network). The bipole networks in different regions may be non-overlapping, and may form effectively non-overlapping continuous fields (e.g., continuous bipole fields). "Effectively non-overlapping bipole fields" means that the broadcast fields of two or more networks do not substantially overlap. For example, the component of a broadcast field (e.g., intensity) due to a second bipole network is less than 15% (or 10%, or 8% or 5% or 1%) of the component due to a first bipole network at any position near the first bipole network, particularly at the excitation ranges described herein.

In any of the embodiments described above, particularly FIG. 6E for example, the device may further include an insulating element or shield 607, as shown in FIG. 6F. The insulating element may be coupled to a single surface (e.g. the top surface) or to both surfaces. In some embodiments the insulating element may slide over and/or wrap around the elongate body of the NLR device. The insulating element may function to prevent an electrode, or portion of electrode, from delivering stimulation to the surrounding area (e.g. to a nerve or other non-target tissue). In some variations, if the shield is limiting the amount of exposed electrode(s) the current density emitted from the exposed electrodes (anode 604 and cathode 605, for example) will increase. In use, the insulating element may first be pulled back such that a large area of electrode(s) are exposed. A user may then slide the insulating element over the electrodes (as shown by the arrow in FIG. 6F) such that a smaller area of electrodes 604 and 605 is exposed. Alternatively, a smaller area may first be exposed and then the insulating element may be pulled back (distally or proximally) to expose a larger portion of electrode(s). In some embodiments, the insulating element may include a window (not shown) through which current may be delivered. In this embodiment, the window may be moved along the length of the elongate body of the device such that different portions of the electrode(s) are exposed sequentially.

FIGS. 7A to 8C also illustrate arrangements of electrodes forming a network on the surface of the NLR device. As indicated in each of these figures, the size and spacing of these electrodes, forming tripolar networks in FIGS. 7A and 7B, and quadrapolar networks in FIGS. 8A and 8C may vary. In some variations, the size and spacing of the electrodes may vary on the same NLR device.

As mentioned above, when a region of the outer surface of a device includes more than one electrode, the electrodes (e.g. bipoles) may be arranged as a bipole network. A bipole network includes at least two bipoles that are formed by at least three electrodes (e.g., two anodes and a cathode or two cathodes and an anode). The bipole network is typically arranged so that all of the bipoles in the network are activated synchronously to create an effectively continuous bipole field along the outer surface. In the examples shown in FIGS. 6A-6D above, the anodes and cathodes forming the bipolar network are arranged so that the current between the two electrodes forms a zigzag pattern. Bipole pairs are located adjacent to each other and share either an anode or a cathode. In some variations, adjacent bipole pairs do not share anode or cathodes. In general, the multipolar networks described herein may form an effectively continuous field along an active region of the outer surface of an NLR device. Adjacent bipole pairs may be positioned close to each other.

As described above, all of the cathodes forming a network may be electrically connected to each other and all of the anodes forming the network may be electrically connected. For example, the anodes of a network may all be formed from a single anodal connector, and the cathodes of a network may be formed from a single cathodal connector. Alternatively, all or a subset of the cathodes of the network may be formed separately so that they can be separately activated or jointly activated. For example, each of the cathodes may be wired to a connector that connects to a power source or controller configured to energize the network in a particular region.

Figure 9:
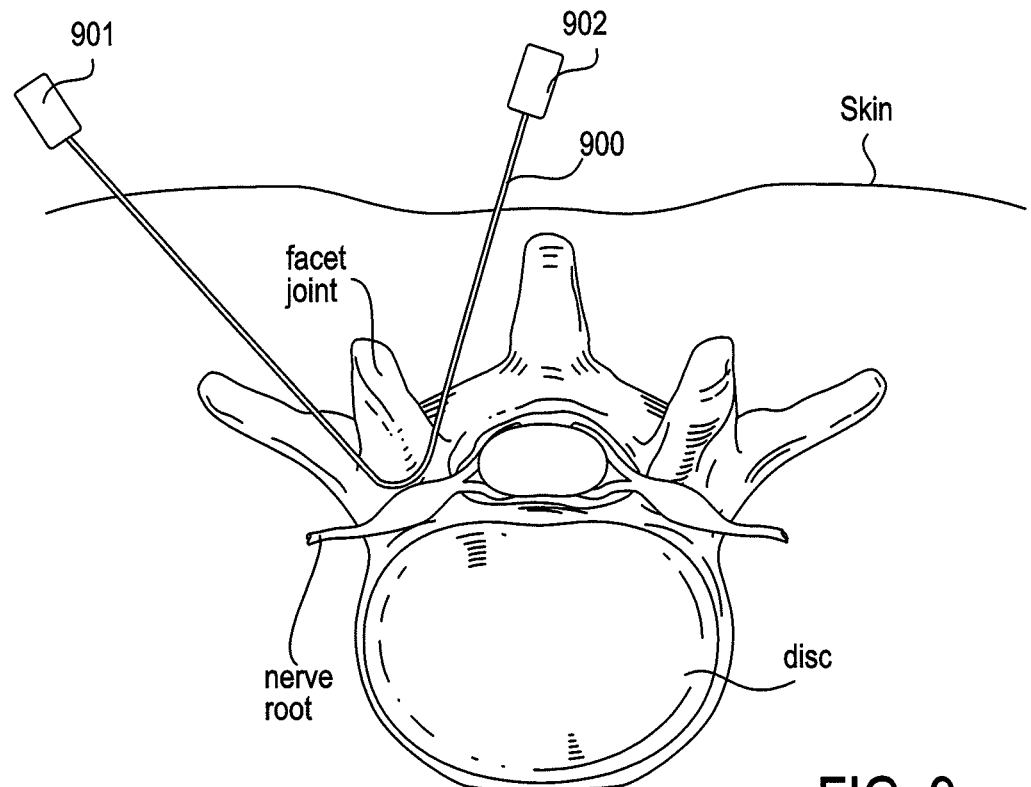
FIG. 9 illustrates an alternative variation of a neural localization device including a single monopolar wire.

FIG. 9 illustrates an embodiment of the neural localization device that includes a simply a single monopolar wire 900. The wire 900 may include a distal end that may be connected to a distal handle 901 and a proximal end that may be connected to a proximal handle 902. The handles remain exterior to the skin of a patient such that the handles may be controlled in a bimanual fashion, as described in detail below. For example, the handles may be pulled up to pull the wire away from the nerve root and then may be pushed down to push the wire closed to the nerve root. By creating a maximum distance and a minimum distance from the nerve root, two distinct threshold current amounts may be established and used to determine the location of the nerve root with respect to the monopolar wire. Methods of using the neural localization devices is described in more detail below.

The monopolar wire may include a sharp (tissue penetrating) distal end and may be long (e.g., elongated) and flexible such that the wire may penetrate tissue and be positioned along a path around target anatomy. For example, the target anatomy may include a facet joint and a ligament (not shown) while non-target tissue may include a nerve root. Current may be delivered to the wire such that a portion of the wire stimulates a nerve root. In some embodiments, the wire may then be used to couple to, position, and activate a tissue modification device. In these embodiments, the proximal end of the wire may include a feature (not shown) that allows it to be coupled to a guidewire coupling member securely. For example, the wire may include a ball or other shaped end (which may be conical, tubular, ring, etc.) at the distal end for coupling to a guidewire coupling member. In some embodiments, the wire may further include an insulating element or shield as described above in reference to FIG. 6F.

Figure 10:
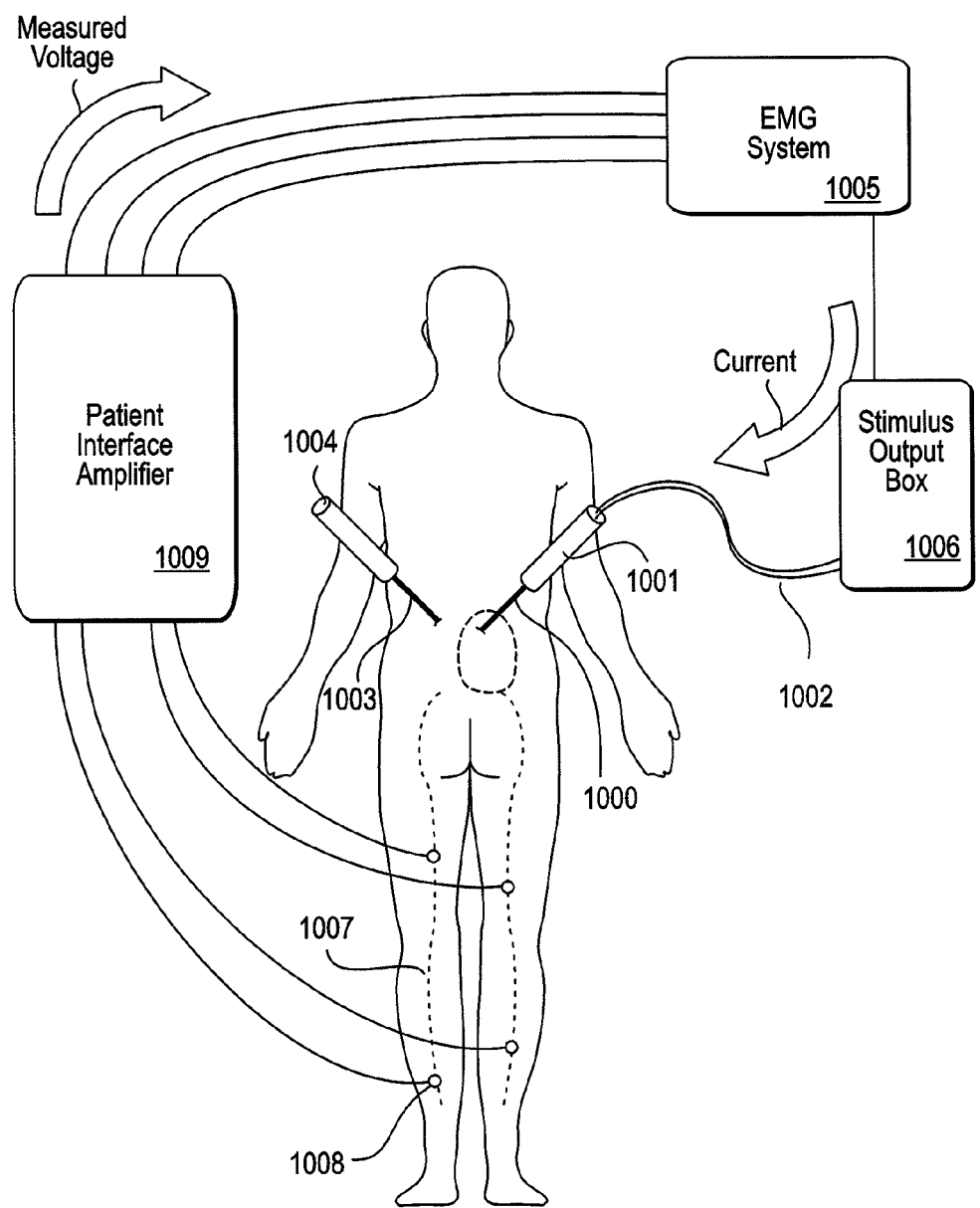
FIG. 10 illustrates an NLR device coupled to a power source such as an EMG system.

The devices described herein may be connected to a power source proximally, or distally. For example, the cathodal and annodal lines which may be used to form the electrodes may extend proximally toward the proximal handle of the device. In this variation, a connector at the proximal region of the device may be used to connect the device to a power source. In one embodiment, as shown in FIG. 10, the device 1000 has a proximal handle 1001 and a stimulus region (inside the patient and not shown) that is coupled to a guidewire 1003 which is coupled to a distal handle 1004. The stimulus region is placed within a patient such that it wraps around target anatomy (such as a facet joint, for example) and is either above (preferable, in most embodiments described throughout) or below a nerve root. A nerve root is the initial segment of a nerve (nerve 1007 for example) leaving the central nervous system. The cathodal and anodal conductors of the device (not shown) are connected to connectors 1002 extending from the proximal handle region of the device. As shown in FIG. 10, the connectors 1002 connect the device 1000 to an EMG system 1005 and a stimulus output box 1006. As shown, current (or voltage) will flow from the EMG system through the stimulus output box to the device 1000. EMG electrodes 1008 may be placed in a leg muscle of the patient as shown. Multiple EMG electrodes may be placed in a plurality of muscles or myotomes as described below with reference to Table 1 below. When the current passes from the device into a nerve root, the current activates the nerve such that a current passes through nerve 1007. The activated nerve thereby activates the corresponding muscle cells. An EMG electrode 1008 coupled to the leg muscle detects the electrical potential generated by the muscle cells when these cells are electrically or neurologically activated by the nerve (nerve 1007, for example). The electrical potential that is detected is known as an EMG response. This response may be amplified by a Patient Interface Amplifier 1009. The response may be detected or measured as a voltage. This voltage may be delivered to the EMG 1005 system for analysis.

As shown below in Tables 1 and 2, EMG electrodes may be placed in any combination of muscles, such as leg muscles for example, to best pick up an EMG response elicited by a neural stimulation of a particular nerve root. Selection of a muscle for placement of EMG electrode(s) may be determined by the nerve root(s) that innervate that muscle. For example, as shown below in Table 1, the Adductor longus is innervated by primarily a L3 nerve root (as indicated by a capitol "X") and also by L2 and L3 nerve roots (as indicated by a lower case "x"). The table below lists several muscles typically monitored during a lumbar spinal surgery. The information provided by the table below may be used to determine ideal placement of EMG electrodes prior to use of an NLR device, or may alternatively be used once an EMG response in elicited by the NLR device to determine the most likely nerve root that has been stimulated based on which muscle returns an EMG response. For example, if the EMG response is elicited in the Extensor Hallucis longus, the NLR device has most likely stimulated a L5 nerve root (as indicated by a capitol "X") and also may have stimulated an L4 and S1 nerve roots (as indicated by a lower case "x").

TABLE 1

Nerve Root to Myotome Map

| Muscle | Level of maximum response (Nerve Root) | | | | | |
|---|---|---|---|---|---|---|
| | L2 | L3 | L4 | L5 | S1 | S2 |
| Iliopsoas | X | x | | | | |
| Adductor longus | x | X | x | | | |
| Vastus medialis | x | X | | | | |
| Vastus lateralis | x | X | x | | | |
| Tibialis anterior | | | X | x | | |
| Peroneus longus | | | x | X | x | |
| Extensor Hallucis longus | | | x | X | x | |
| Flexor Hallucis longus | | | | x | X | x |
| medial Gastrocnemius | | | | x | X | x |
| lateral Gastrocnemius | | | | x | X | x |
| Gluteus maximus | | | | x | X | x |
| Biceps femoris | | | | x | x | x |
| Anal Sphincter | | | | | | x |

As listed below in Table 2, depending on the location of the surgery, particularly a disc level(s) in spinal surgery, different muscle groups may be targeted for placement of the EMG electrodes. For example, as listed in the table below, when a spinal surgery is performed at level L3/L4, the nerve root that is most likely at risk to be damaged during the procedure is a L3 nerve root for a "disc level pass" and a L4 nerve root for an "along the nerve root pass". As illustrated in FIG. 34A and described in further detail below, the path through the spine may be an "above the pedicle pass" or "disc level pass" (as indicated by arrow 3401) so that the guidewire may pull in the NLR device tangential to the direction of the exiting spinal L3 nerve root 3400. The path may also be parallel to the exiting L4 nerve root 3403 (e.g., "below the pedicle pass" or "along the nerve root pass" as indicated by arrow 3402). In order to most effectively monitor the L3 and/or L4 nerve roots, it is desirable to place the EMG electrodes in muscles innervated by those nerves. For example, in Setup 2 as listed in Table 2 below, the EMG electrodes may be placed in the Vastus Medialis and Tibialus Anterior muscles. As indicated, the Vastus Medialis is innervated by the L2 and L3 nerve roots and the Tibialus Anterior is innervated by the L4 and L5 nerve roots. For a more comprehensive setup, as indicated by Setup 4, the EMG electrodes may be placed in the Vastus lateralis, the Tibialis Anterior, the Adductor longus. As indicated, this comprehensive setup option provides overlap between the muscles and nerve roots of interest that innervate them.

TABLE 2

EMG Electrode Placements (DP = Disc Pass, AN = Along Nerve)

| Surgical Level | At Risk Nerve | Setup 1 Muscles | Setup 2 Muscles | Setup 3 Muscles | Setup 4 Muscles |
|---|---|---|---|---|---|
| L2/L3 | DP = L2 AN = L3 | *Adductor longus (2, 3, 4), Vastus lateralis (2, 3, 4) | Vastus Medialis (2, 3) | Vastus medialis (2, 3), Vastus lateralis (2, 3, 4), Iliopsoas (2, 3) | Vastus medialis (2, 3), Vastus lateralis (2, 3, 4), Adductor longus (2, 3, 4) |
| L3/L4 | DP = L3 AN = L4 | *Adductor longus (2, 3, 4), Vastus lateralis (2, 3, 4) | Vastus Medialis (2, 3), Tibialus Anterior (4, 5) | Vastus medialis (2, 3), Vastus lateralis (2, 3, 4), Tibialis Anterior (4, 5) | Vastus lateralis (2, 3, 4), Tibialis Anterior (4, 5), Adductor longus (2, 3, 4) |

TABLE 2-continued

EMG Electrode Placements (DP = Disc Pass, AN = Along Nerve)

| Surgical Level | At Risk Nerve | Setup 1 Muscles | Setup 2 Muscles | Setup 3 Muscles | Setup 4 Muscles |
|---|---|---|---|---|---|
| L4/L5 | DP = L4 AN = L5 | Vastus lateralis (2, 3, 4), Extensor Hallucis Longus (4, 5, 1) | Tibialus Anterior (4, 5), Biceps femoris (5, S1, S2) | Tibialis Anterior (4, 5), Gastrocnemius (5, S1, S2) | Vastus lateralis (2, 3, 4), Tibialis anterior (4, 5), Gastrocnemius (5, S1, S2) |
| L5/S1 | DP = L5 AN = S1 | Extensor Hallucis Longus (4, 5, S1), Medial Gastrocnemius (5, S1, S2) | Tibialus Anterior (4, 5), Medial Gastrocs (5, S1, S2), Biceps femoris. (5, S1, S2) | Gastrocnemius (5, S1, S2), Extensor hallucis longus (4, 5, S1), Flex. hallucis longus (5, S1, S2), Anal sphincter (S2, S3) | Gastrocnemius (5, S1, S2), Tibialis Anterior (4, 5), Extensor Hallucis longus (4, 5, S1) |
| L3/L4/L5 | | *Adductor longus (2, 3, 4), Vastus lateralis (2, 3, 4), Extensor Hallucis Longus (4, 5, 1) | Vastus Medialis (2, 3), Tibialis Anterior (4, 5) Medial Gastrocs (5, S1, S2), Biceps femoris. (5, S1, S2) | | Vastus lateralis (2, 3, 4), Tibialis Anterior (4, 5), Adductor longus (2, 3, 4), Gastrocnemius (5, S1, S2) |
| L4/L5/S1 | | Vastus lateralis (2, 3, 4), Extensor Hallucis Longus (4, 5, 1), Medial Gastrocnemius (5, S1, S2) | Tibialis Anterior (4, 5) Medial Gastrocs (5, S1, S2), Biceps femoris (5, S1, S2) | | Vastus lateralis (2, 3, 4), Tibialis Anterior (4, 5), Extensor Hallucis longus (4, 5, S1), Gastrocnemius (5, S1, S2) |
| L3/L4/L5/S1 | | *Adductor longus (2, 3, 4), Vastus lateralis (2, 3, 4), Extensor Hallucis Longus (4, 5, S1), Medial Gastrocnemius (5, S1, S2) | Vastus Medialis (2, 3), Tibialis Anterior (4, 5) Medial Gastrocs (5, S1, S2), Biceps femoris. (5, S1, S2) | | Vastus lateralis (2, 3, 4), Tibialus Anterior (4, 5), Extensor Hallucis longus (4, 5, S1), Gastrocnemius (5, S1, S2) |

The power source may be configured for stimulating one or more regions of the NLR device either simultaneously or sequentially, or individually. For example, in variations in which the NLR device includes a top region and a bottom region, each with its own electrode network (e.g., bipole network), the stimulator (or a controller communicating with the stimulator, such as EMG system 1005) may apply energy to only the top region network or the bottom region network in a controllable, or indicated fashion, so that the patient can be monitored to determine if a nerve is nearby the top region or bottom region. For example, the patient may be monitored for muscle twitch or EMG response immediately following one or more stimulation protocols. The stimulation may be preset (e.g., a predetermined power level or series of power levels, a ramp of power levels, etc.) or it may be varied depending on feedback. For example, the power level may be increased to a threshold (of muscle or simulation response). The power level may be limited or capped to prevent damage to tissue or the like. Thus, an NLR device for determining if a nerve is nearby may also include a controller for controlling the application of energy to the electrodes. For example, the device may include a switch that can select the activation of either the top stimulation region or the bottom stimulation region. In particular, the application of energy to the electrodes may be coordinated as described in the methods sections below, so that the activation of a nerve can be correlated to a particular region of the surface of the device.

The nerve localization devices and systems described herein may include one or more indicators or outputs. The detectors may provide a user-identifiable signal to indicate the location of the nerve or the status of the system. For example, the nerve localization devices may include one or more light emitting diodes (LEDs), buzzers (or other sound output), a video display, or the like. An LED may be illuminated based on signals generated by, received by, or generated in response to the energized electrode(s) as discussed above. In some variations the system or devices create a vibration or sound that a user manipulating the device 20 may feel or hear. The intensity of the output may vary as a function of detected signal. Alternatively, all indicators or outputs may be located on an external EMG system as described above with respect to FIG. 10.

Figure 11A:
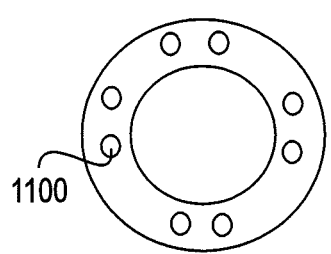
FIGS. 11A-11C show cross-sections through different variations of NLR device.
Figure 11B:
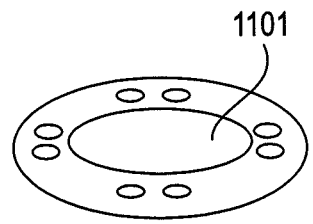
Figure 11C:
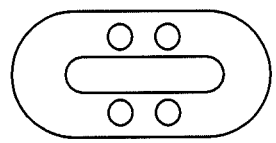

The NLR devices described herein may be fabricated in any appropriate manner. For example, the devices may be formed by extrusion. FIGS. 11A-11C illustrate methods of fabricating variations of NLR devices. For example, FIGS. 11A and 11B show a device that is fabricated as an extrusion of material (e.g., PBAX) as an elongated cylinder having a round cross-section, as shown in FIG. 11A. The walls of the cylinder include openings 1100 into which the conductive channel such as the annodal and cathodal channels connecting to the electrodes may pass. In some variations, these conductive channels may include a wire or a conductive filling. The structure may be extruded around the wire (or conductive material), or it may be added after the extrusion. Some of these channels, or additional channels (not shown), may include cables or tensioning elements for steering, or for attaching to a guidewire or other components. As mentioned above, the electrodes may be formed by laser cutting to form vias to the conductive channels, and filling with a conductive matrix to form the surface electrode. In some embodiment, the surface electrode may be preferably flush with the surface of the NLR device, to prevent 'snagging' or damaging adjacent tissues. Alternatively, the electrodes may be proud to provide enhanced approximation to a nerve root.

The circular cross-section shown in FIG. 11A may be flattened (e.g., crushed, compressed, etc.) into an oval, rectangular, or substantially flat shape. FIG. 11B illustrates an example of a substantially flat shape. This shape may be completely flattened, or it may include a central lumen 1101.

The central lumen may be used to hold one or more cables or stiffening members, or for passages of a tool, guidewire, or the like.

In some variations, the NLR body may be formed in the ribbon or oval cross-section. For example, the NLR body may be extruded as an oval shape, as shown in FIG. 11C (also in the example shown in FIG. 46). Fabricating the NLR body as an extruded oval or other flattened cross-section may enable better control and reliability of the dimensions and integrity of the lumen formed in the device. The flattened, ribbon-shaped devices described herein may more readily access narrow, tortuous or difficult to reach body regions, as mentioned above, including neural foramen. In addition, the separation between different electrodes in the devices such as those shown for FIGS. 11B and 11C, in which the electrodes connected to the wires or conductive filling, may be controlled so that the electrodes are relatively close to each other (e.g., forming bipole pairs) while separated from the edges of the device and/or the other electrodes. The shape of the NLR device (e.g., the ribbon shape) may be similar to shape of the tissue modification device that it is to be used with during a procedure, which may help predict placement of the tissue modification device. As described below, the device may also be shaped as an expander or dilator, or may be used with an expander or dilator. For example, the body of the NLR device (or a portion of the NLR body) may be expandable or inflatable.

Figure 12A:
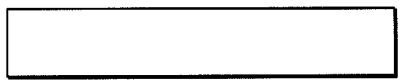
FIGS. 12A-12G show top (12A-12D) and end perspective views (FIGS. 12E-12G) of various embodiments of the NLR devices described herein.
Figure 12B:
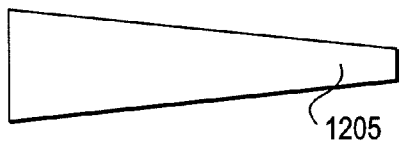
Figure 12C:
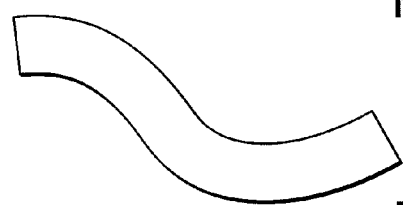
Figure 12D:
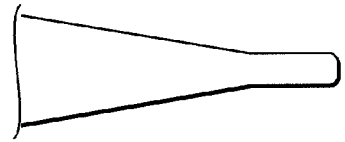
Figure 12E:
Figure 12F:
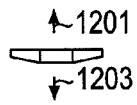
Figure 12G:

FIGS. 12A to 12G illustrate other exemplary NLR body shapes. For example, FIG. 12A (shown in cross section in FIG. 12E) shows an NLR body shape that is approximately rectangular, although ribbon-shaped, as previously illustrated in FIGS. 1A and 2A. FIG. 12B shows another variation of a ribbon-shaped body region in which the device is tapered longitudinally, though still substantially "flat," as shown in FIG. 12F. As mentioned, the NLR body may be configured as a dilator or expander. Thus, in one variation similar to that shown in FIGS. 12B and 12F, the ribbon shaped body is flexible in at least one axis (e.g., up 1201 and down 1203, as illustrated by the arrows in FIG. 12F, but relatively incompressible, particularly in the direction perpendicular to the axis of flexibility. Thus, the device shown in FIG. 12B may be inserted into a body region by the narrower distal tip region 1205, and may dilate the opening by pulling the device distally into the space so that the wider proximal region moves into the opening.

The NLR device or device body may have a curved or arcuate body region, as illustrated in FIG. 12C. In some variations the NLR body may be shape-changing. For example the NLR body be transformable from a linear shape (such as that shown in FIG. 12A) along the length to a curved or S-shaped configuration, as shown in FIG. 12C and in profile in FIG. 12G. For example, the body may include a wire or tensioning element to transition the device from one configuration to another. In addition to wires and tensioning elements, other transitioning elements include balloons that may inflate and/or deflate to change the shape of the NLR body. Any of the NLR body shapes described herein may be combined or modified. For example, FIG. 12D is another example of a tapered NLR body region including a distal end that is rectangular.

Figure 13A:
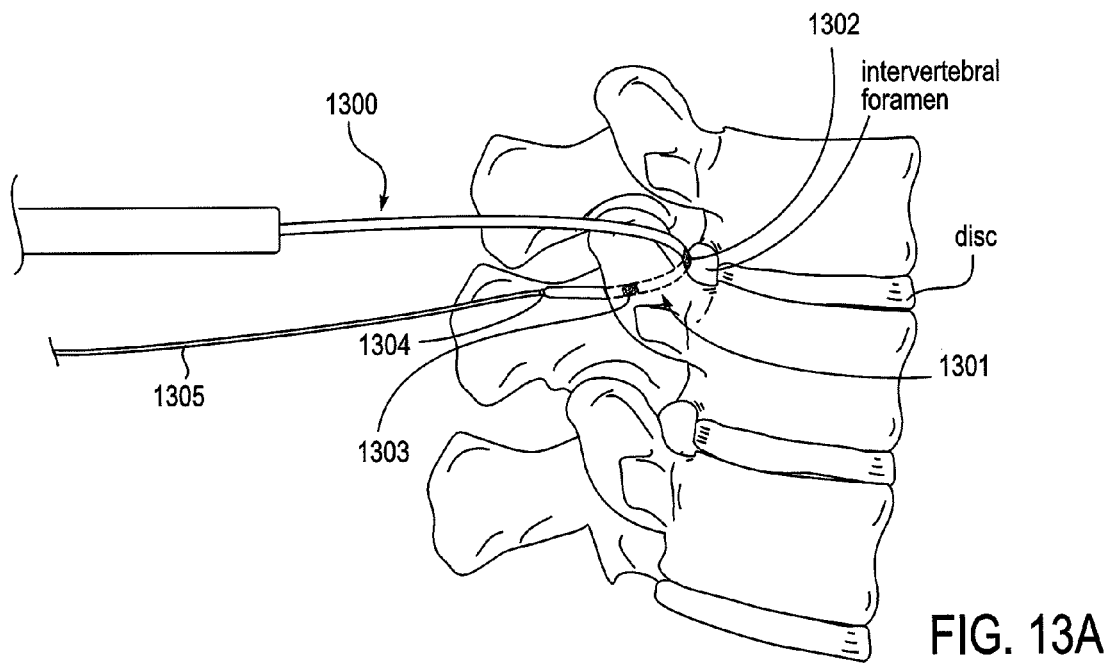
FIGS. 13A-13B illustrate an NLR device having markers, such as radio-opaque markers.
Figure 13B:
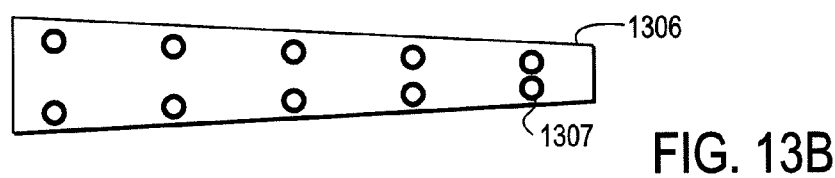

In some embodiments, as shown in FIGS. 13A and 13B, the NLR elongate body may include radioopaque markers that may be used help localize and accurately position the NLR device, particularly the stimulation region of the device. For example, the NLR device may include one or more radioopaque regions that can be used to orient or mark the device. In general, the NLR devices described herein may be inserted and positioned relative to the body so that the top and bottom stimulation regions (which are typically opposite each other) are positioned correctly relative to the anticipated orientation of the a nerve or nerve root. As shown in FIG. 13A, the region of the NLR device 1300 in which the electrodes extend may be referred to the active region or the stimulation region 1301. The stimulation region 1301 in this example is shown as marked by radioopaque markers 1302 and 1303 on the proximal and distal end of the stimulation region, respectively. As shown, the markers may allow for visualization of the NLR device while inserted into a body region (e.g., using fluoroscopy or the like). For example, radioopaque markers will show up under fluoroscopy darker than the rest of the device. As shown in FIG. 13A, it may be preferable to position the device 1300 such that when viewed in a lateral view under fluoroscopy the proximal marker 1302 is located at the bottom of the curvature of the device body and the distal marker is located half way between the proximal marker and the distal tip 1304 of the device. As shown, distal tip 1304 includes a guidewire coupler and is coupled to a guidewire 1305.

Markers may also help with determining the size of a body region into which the NLR device is inserted. For example, as shown in FIG. 13B, the NLR device 1306 may include one or more marker 1307 at a fixed position along the length of the NLR body region. The fixed position may have a known width and height. In some variations, the marker is indicative of the position along the length of the device. For example, when a device includes a plurality of markers, the markers may be differently sized or shaped, or multiple markers may be arranged in a way that indicates position and/or orientation within the tissue. Thus, when radioopaque markers are used, the NLR devices may be used in conjunction with a fluoroscope, as indicated in FIG. 13A. FIG. 13B illustrates one variation of a tapering NLR body (seen from the top) having identifying markers along the length, as shown.

Figure 14A:
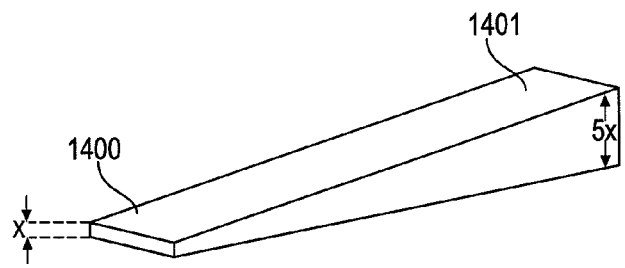
FIGS. 14A-14B illustrate different sizing and/or dilating features of NLR devices.
Figure 14B:
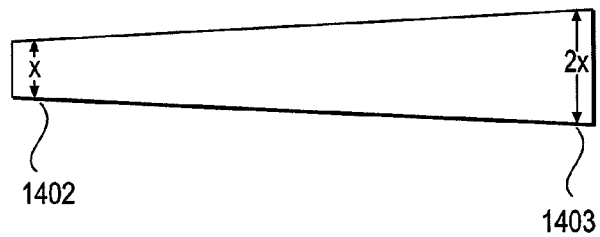

As mentioned above, the NLR devices may be dilating devices, or may be used in combination with dilating devices. FIGS. 14A and 14B show two variations of NLR body regions that are configured as dilators. FIG. 14A illustrates an NLR body region that dilates by increasing the thickness (by 5× in this example) from the distal (thin) end 1400 to the proximal (thick) end 1401. The electrodes on the surface(s) of the NLR body are not shown in the example of FIGS. 14A and 14B, but may be arranged in any configuration, as described above. FIG. 14B illustrates a width dilating NLR body, which expands to twice the width from the distal end 1402 to the proximal end 1403. In some variations, the expanding region of the NLR body may be inflatable. For example, the expandable region may be a balloon along a portion (or the entire) ribbon body.

Figure 15:
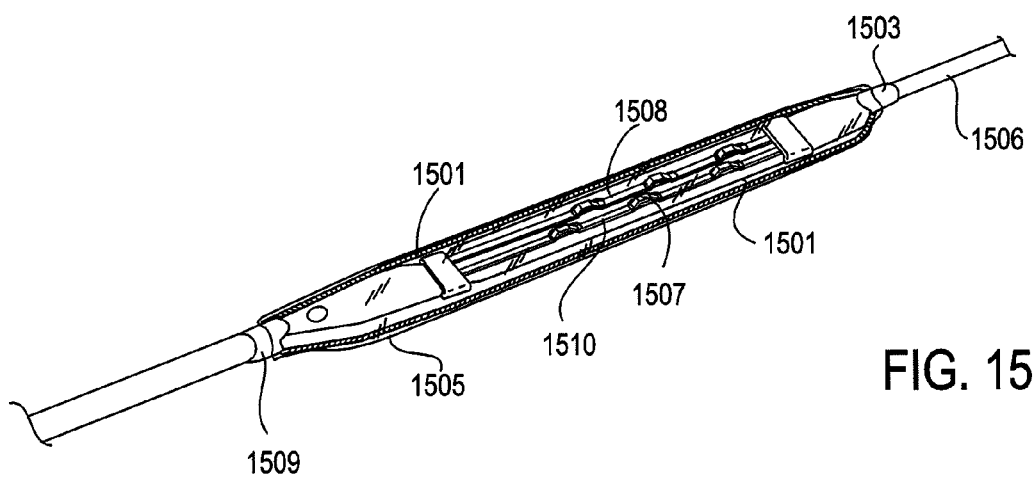
FIG. 15 illustrates another variation of an NLR device.

FIG. 15 illustrates another variation of an NLR device in which is fabricated as a ribbon-shaped device including two parallel cables or wires 1501 forming the sides of the device, and a plastic overmolded piece 1505 extending between them. The resulting structure is thin and flexible. The ends of the cables (or wires) 1501 can be connected to form connections to other portions of the device, including the connector or coupler (e.g., guidewire connector 1503) or a shaft region (e.g., proximal shaft 1509). See FIGS. 26A-29C for further details about the parallel cables or wires 2600 disposed along a length of the device. In some variations, guidewire connector 1503 is connected to a guidewire 1506. In FIG. 15 a plurality of electrodes 1507 are arranged along the length of the plastic overmolded region. In this example, a cathodal wire 1508 and annodal wire 1510 include a plurality of ridges or bumps that extend beyond the plastic overmold, as described above, to form a series of proud electrodes 1507. Thus, all of the cathodes may be connected to a single cathodal line and all of the anodes may be connected to a single annodal line. The annodal wire or line and the cathodal wire or line may be embedded in the plastic overmold. The cathodes and anodes formed in the top surface may be isolated from any cathodes and anodes formed in the bottom surface. For example, the cathodal line and anodal line forming the cathodes and anodes may be separate for the top and bottom. In some variations the surface includes more than one anodal and/or cathodal lines. In some variations the NLR device includes electrodes only on one surface (e.g., the top surface).

Methods of Operation

The neural localization ribbon devices described herein are typically used to determine if a nerve is near at least one side or region of the device. For example, an NLR device can be used to determine if a nerve is on one side of the NLR device before cutting or otherwise modifying the tissue; this could be used to prevent cutting or otherwise damaging the nearby tissue, particularly neural tissue. Thus, any of the NLR devices described herein may be used before modifying the tissue to determine if a particular pathway through the tissue is safe for use with a tissue modification device.

In operation, the NLR devices described herein are particularly useful for use with bimanual systems in which both the NLR device and the tissue modification device are passed through a narrow and/or tortuous body region from a first site outside of the patient, around a tissue to be modified (e.g., target tissue) and either has a portion extending out of the patient or couples to another device (e.g., guidewire) extending out of the patient, often (though not necessarily) out of a second site outside of the patient. As described more fully in many of the patent applications incorporated by reference above, such bimanual systems may provide an advantage to the surgeon or medical professional performing the procedure, because both ends of the devices may be manipulated (e.g., pulled), providing a mechanical advantage and/or a control advantage.

Thus, in some variations, the NLR devices describe herein are inserted into the patient and near a target tissue using a guidewire that has first been threaded through the patient and around the target tissue. A guidewire may be inserted into a patient using an introducer, including a curved introducer or probe. Thus, the guidewire may be inserted into the body at a first angle of approach, then may be guided around a target tissue (e.g., through a neural foramen) using a curved introducer/guide or a steerable guide (or, in some variations using a steerable guidewire), so that the distal end of the guidewire, which may be tissue penetrating, exits the patient while a portion remains curved around the target tissue. The proximal end of the guidewire may be adapted so that it can be connected to the NLR device and/or a tissue modification device. For example, the proximal end region of the guidewire may be coupled to the distal end of the NLR device and the NLR device can be positioned near the target region by pulling on the distal end of the guidewire. This variation, in which the distal end of the guidewire is pulled from the patient to position the NLR device and/or tissue modification device may be advantageous because the guidewire may not take up space in a narrow target region, allowing the NLR device and/or tissue modification device to enter this otherwise limited space. Alternatively, in some variations, the NLR devices described herein may be used in an "over the wire" configuration, in which the devices are threaded over the guidewire and typically pushed into position.

In an alternative embodiment, the NLR device may include a flexible distal end region, such as an integrated guidewire at the distal end of the device, which may be inserted into a patient (for example, using an introducer, including a curved introducer or probe). The distal end of the device may be inserted into the body at a first angle of approach, then may be guided around a target tissue (e.g., through a neural foramen) using a curved introducer/guide or a steerable guide (or, in some variations using a steerable guidewire), so that the distal end, which may be tissue penetrating, straightens out and exits the patient while a portion remains curved around the target tissue. As the distal end of the device is pulled around this path, the remainder of the NLR device will be pulled along behind it, such that the stimulation region of the NLR device is pulled into position around the target tissue. If a curved introducer/guide or a steerable guide is used to position the distal end of the NLR device around a target tissue, the guide may be removed before the remainder of the NLR device is pulled into position. The curved introducer may be configured such that it can be pulled/torn off and away from the flexible distal end of the NLR device instead of pulled back over the proximal end of the NLR device itself.

Figure 16A:
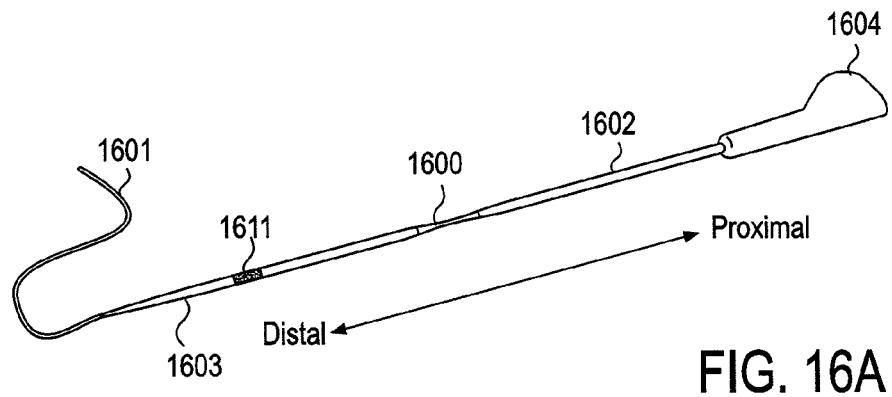
FIGS. 16A-16B illustrate an alternative embodiment of an NLR device.
Figure 16B:
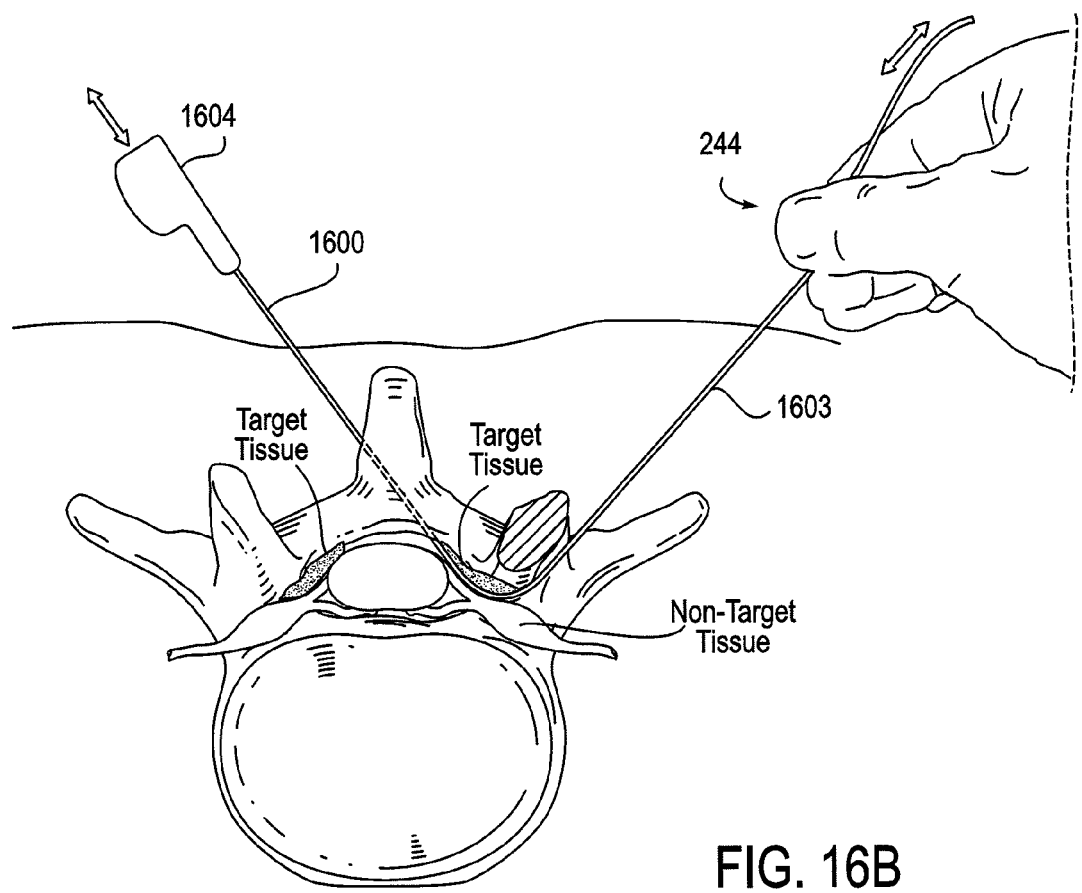

In some variations, the neural localization device may have an integral guide region at the distal end so that the device does not need any additional guidewire/coupler. With reference now to FIGS. 16A and 16B, more detailed figures of one embodiment of an NLR device 1600 with a flexible distal end 1601 are shown. Referring to FIG. 16A, NLR device 1600 may include elongate body 1603 having proximal portion 1602 and flexible distal end 1601, a stimulation region 1611 disposed along elongate body 1603, and proximal handle 1604. In various embodiments, elongate body 1603 may have any number of dimensions, shapes, profiles and amounts of flexibility. For example, distal portion 1601 is shown having a curved shape to demonstrate that at least a portion of elongate body 1603 may be flexible. The distal portion is preferably flexible in at least one direction, such that it may wrap around a target tissue, while being more stiff in at least one direction such that the distal end may penetrate tissue without buckling. In some embodiments, the distal end may have a sharp distal tip configured to penetrate and/or pierce tissue. In various embodiments, elongate body 1603 may have one or more of a round, ovoid, ellipsoid, flat, cambered flat, rectangular, square, triangular, symmetric or asymmetric cross-sectional shape. As shown in FIG. 16A, elongate body 1603 has a relatively flat configuration, which may facilitate placement of body 1603 between target and non-target tissues. Distal portion 1601 of body 1603 may be tapered, to facilitate its passage into or through narrow spaces as well as through small incisions on a patient's skin. Body 1603 may also include a slightly widened portion around the stimulation region 1611. Distal end 1601 may be long enough to extend through a first incision on a patient, between target and non-target tissue, and out a second incision on a patient. In some embodiments, the distal end may have a length greater than or equal to 3 inches such that it may extend from around the proximal end of the stimulation region to outside the patient where it may be grasped by a user and/or a distal handle. In some alternative embodiments, the distal end may have a length greater than or equal to 10 inches while in some other alternative embodiments, the distal end may have a length greater than or equal to 16 inches. Alternatively, distal end 1601 may be long enough to extend through a first incision, between the target and non-target tissue, and to an anchoring location within the patient. In another alternative embodiment, distal end 1601 may be long enough to extend through a first incision, between the target and non-target tissue, to a location nearby but distal to the target tissue within the patient, with some portion of NLR device 1600 anchored to the patient in some fashion.

In some embodiments, it may be advantageous to include one or more rigid sections in elongate body 1603, such as to impart pushability to a portion of the body or to facilitate application of force to the stimulation region 1611 without causing unwanted bending or kinking of elongate body. In such embodiments, rigidity may be conferred by using additional materials in the body or by making the rigid portions thicker or wider or of a different shape. For example, a stiffening member may be disposed along the length, or a portion of the length, of the elongate body and/or stimulation region.

Referring now to FIG. 16B, one embodiment of a method for using an NLR device in a spine is demonstrated in simplified, diagrammatic, cross-sectional views of a portion of a patient's back and spine. FIG. 16B shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

In FIG. 16B, the NLR device 1600 has been positioned in the patient's back to determine if a nerve is nearby a region of the device and/or the location of the nerve with respect to the NLR device. Various methods, devices and systems for introducing NLR device into the patient and advancing it to the position are described in further detail in many of the patent applications previously incorporated by reference. Generally, the NLR device may be positioned via a percutaneous or open surgical procedure, according to various embodiments. In one embodiment, device 1600 may be inserted into the patient through a first incision, advanced into the spine and between target tissue and non-target tissue (such as spinal cord, nerve roots, nerves and/or neurovascular tissue), and further advanced so a distal portion of elongate body 1603 exits a second (or distal) incision to reside outside the patient. In positioning device 1600, a first or "top" surface may be positioned to face the target tissue, while a second or "bottom" surface may be positioned to face non-target tissue.

Once device 1600 is positioned in a desired location, anchoring force may be applied at or near the distal portion of elongate body 1603. In one embodiment, applying anchoring force involves a user 244 grasping body 1603 at or near its distal portion 1601. In alternative embodiments, anchoring force may be applied by deploying one or more anchor members disposed at or near the distal portion of body 1603. Once the anchoring force is applied, proximally-directed tensioning force may be applied to device 1600, such as by pulling up proximally on handle 1604. This tensioning force may help urge the NLR device against the target tissue (one-directional, vertical arrows near target tissue), thus enhancing contact with the target tissue and facilitating nerve location determination. Alternatively, a user may push down on the distal end of the device while holding the proximal handle in place or may push down on both the distal end of the device and the proximal handle. This downward force will push the NLR device, and the stimulation region in particular down toward the non-target tissue, thus enhancing contact with the non-target tissue and facilitating nerve location determination. This method of moving the stimulation region of the NLR device with respect to the target and non-target tissue is described in further detail below.

With respect to both the guidewire embodiment and the integrated flexible distal end embodiment described above (or any other suitable configuration), once near the target region (e.g., the region around which the guidewire is curved), the NLR device may be used to determine if a nerve is nearby. In particular, the NLR device may be used to determine if a nerve is nearby one side of the NLR device, such as the 'top' of the device, corresponding to the side of the target tissue which will be modified by the tissue modification device. Thus, in some variations, the NLR device is oriented so that it includes a distinct first (e.g., top) and second (e.g., bottom) surfaces. The orientation of the ribbon-shaped NLR device may be maintained as the device is passed into the target tissue (e.g., by pulling the guidewire). In some variations, the device includes one or more markers (e.g., radioopaque regions) indicating the orientation of the NLR device within the tissue. In some variations, the orientation of the NLR device is maintained proximally, thus the orientation of the portion of the NLR device in the tissue may be determined (or maintained) as it is positioned distally within the tissue. For example, the proximal end of the device may be marked. Once the NLR device is positioned near the target tissue, energy may be applied to the electrode(s) to determine if a nerve is nearby.

The method of determining if a nerve is nearby an NLR device, or a region of an NLR device, generally includes the steps of exciting a electrodes (or network of electrodes) to pass current between electrodes (e.g., bipole pairs) and creating a stimulation field (such as a limited broadcast field) that can selectively stimulate a nearby neuron. As mentioned above, the broadcast field may be limited by the geometry of the electrodes and the networks, and by the applied energy. The subject can then be monitored (directly or indirectly) to determine if a nerve has been stimulated in response to the emitted broadcast field; the magnitude of the response can also be compared for different bipole networks (or bipole pairs) in different regions of the device to determine which region is nearest the nerve.

For example, in some variations the NLR device has a top and a bottom surface that each includes a network of anodes and cathodes. Once the NLR device is positioned near the target tissue (e.g., around the target tissue), for example, by pulling in to place using a guidewire coupled to the distal end of the NLR device, the NLR device may stimulate either the top or the bottom to determine if a nerve is nearby either surface. The stimulation may be applied in a pattern. For example, the level of stimulation may be applied first to one side, then to the other, or it may alternate between the two sides (e.g., exiting at the same level on each side before increasing the power and then re-stimulating on each side again).

In some variations, the method may include repeatedly energizing only a subset of the bipole networks (or bipole pairs) until a nerve is detected, and then other bipole networks on the device may be energized to determine with more accuracy the relationship (e.g., orientation) of the nerve with respect to the device.

Figure 17:
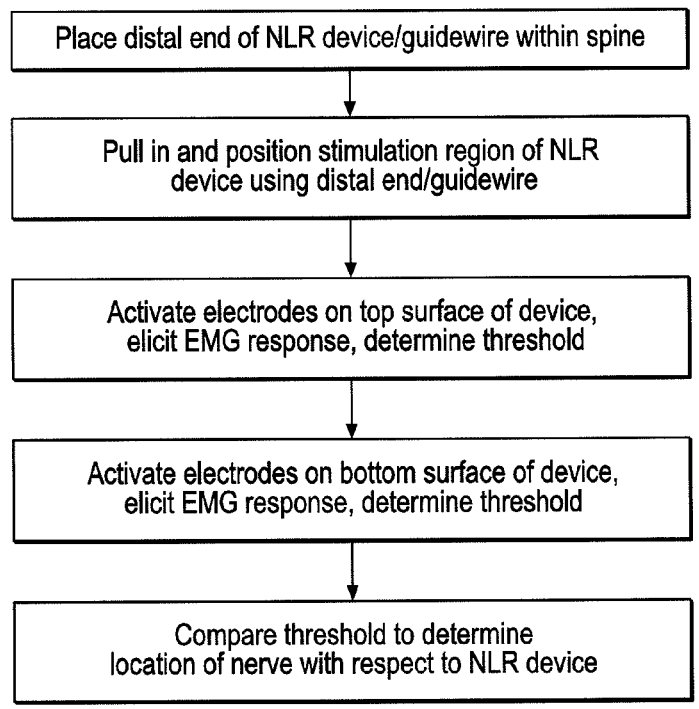
FIGS. 17 and 18 schematically methods of operation of variations of the NLR device.

In some variations, multiple regions on the same side of the device are stimulated to determine if a nerve is nearby. For example, a second region of the device having its own network may be stimulated proximally or distally along the NLR device. Additional energizing and monitoring steps may be included for other regions of the device, if present. The responses to the different regions can be compared, to determine if a nerve is nearby. Optionally, it may be determined which region of the device is closer to the nerve. FIG. 17 illustrates a method of determining which region of the device is closer to the nerve. For example, if a nerve is closer to the bottom region, a threshold stimulation current required from the bottom surface of the NLR device to elicit an EMG response, for example, may be lower than a threshold stimulation current required from the top surface of the NLR device to elicit an EMG response.

If the nerve is detected, the tissue may be acted on (e.g., cut, ablated, removed, etc.), particularly when the nerve is on the side of the device facing away from the tissue to be acted on by the tissue modification device. In some variations the device may moved, and the excitation steps may be repeated until the pathway around the target tissue avoiding the nerve is determined. Thus, the steps may be repeated until the device is positioned as desired, and a procedure may then be performed. In some variations, the NLR device may be withdrawn. For example, the NLR device may be removed by pulling proximally, leaving the guidewire in position so that the guidewire can be used to pull in the tissue modification device or other devices (e.g., tissue shields, etc.) along the same pathway. Alternatively, the NLR device may be pulled distally, particularly when the proximal end of the NLR device has been coupled to a tissue modification device. The NLR device can then be removed distally (uncoupled from the tissue modification device), or it can remain attached, and the NLR device can be used to pull, position and/or actuate the tissue modification device. For example, the tissue modification device can be pulled to urge the tissue modification device against the tissue. In some variations, the tissue modification device may be coupled to (or integral with) the NLR device.

As mentioned, the step of monitoring or detecting a response may be performed manually (e.g., visually), or using a sensor or sensor. For example, using an accelerometer may be coupled to muscle. The accelerometer may be a multiple axis accelerometer that detects the movement of the muscle in any direction, and movement coordinated with stimulation may be detected. In some variations, a strain gauge may be used on muscle innervated by a nerve passing through or originating in the region of tissue being examined. The strain gauge may be a multiple axis strain gauge that detects the movement of the muscle in any direction. In some variations, an EMG probe may be used to measure evoked potentials of the muscle. The magnitude of any response may also be determined.

Figure 18:
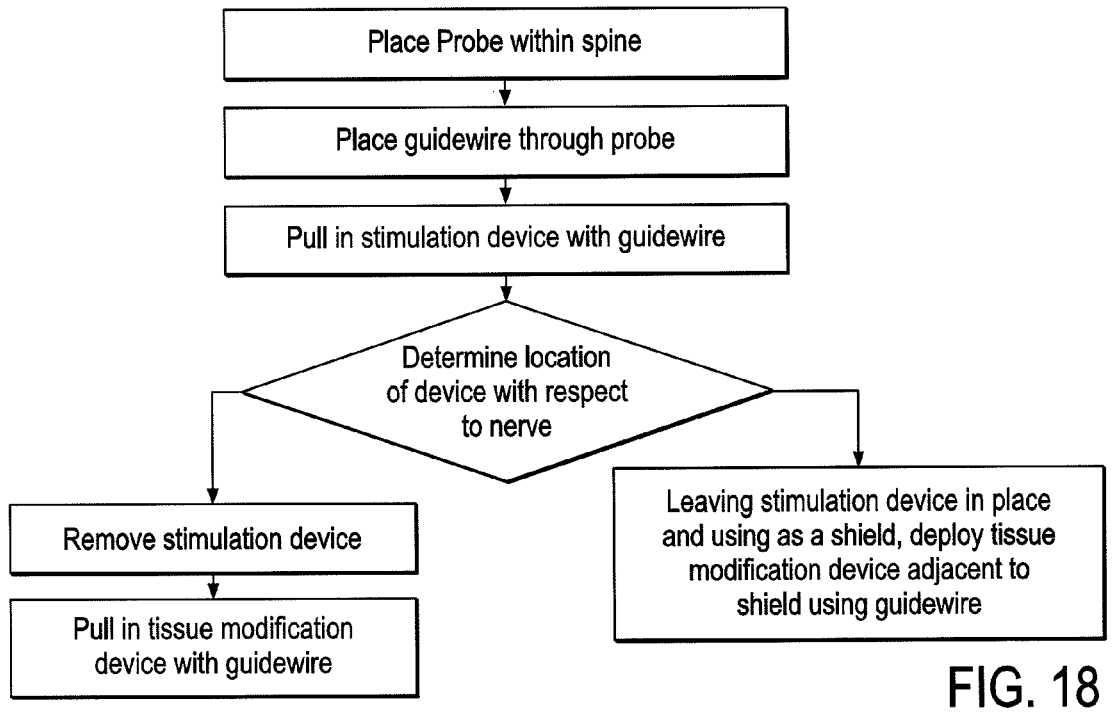

FIG. 18 illustrates some variations of the methods of using the NLR devices described herein. In FIG. 18, the method may include the steps of positioning a guide or probe to insert the guidewire near (e.g., around) the target tissue. The guidewire may then be used to pull in the NLR device ("stim ribbon"). After stimulation to determine if a nerve is nearby (e.g., between the NLR device and the target tissue, the device may be removed and/or exchanged for a tissue modification tool (e.g., decompression tool), or it may be left in place and used as a shield while the tissue modification tool is deployed over it, as illustrated by the variation shown in FIG. 19.

Figure 19:
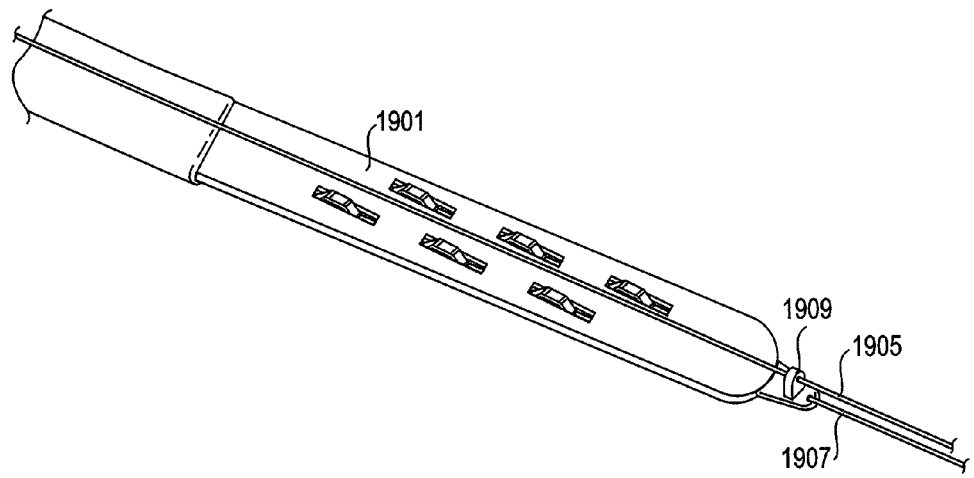
FIG. 19 is another variation of an NLR device.

In FIG. 19, the NLR device 1901 is coupled at the distal end to a first guidewire 1907. The NLR device includes a channel or guide 1909 for a second guide wire (or "exchange wire") 1905. The second guidewire 1905 may be pulled in with the NLR ribbon as the NLR device is pulled into position, and then extended from the distal end of the NLR device once the position of the nerve has been confirmed. The proximal end of the second guidewire 1305 may be coupled to a tissue modification device (not shown) and then used to pull the tissue modification device in place over the NLR device, while keeping the NLR device in position. Thus, the NLR device may act as a shield or barrier to prevent damage to a nearby nerve, which is detected on the opposite side of the NLR device (e.g., the bottom) away from the second guidewire, and therefore the tissue modification device.

Integrated Embodiments

Figure 20A:
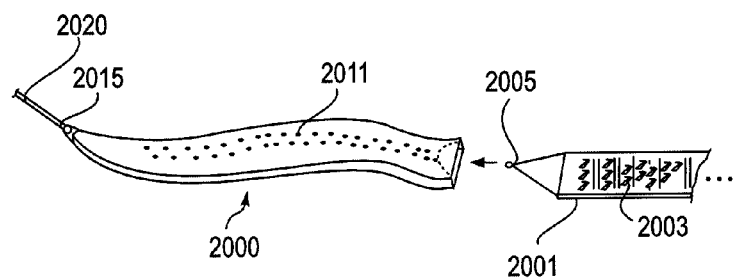
FIGS. 20A and 20B shows variations of NLR devices configured for coupling with another device.
Figure 20B:
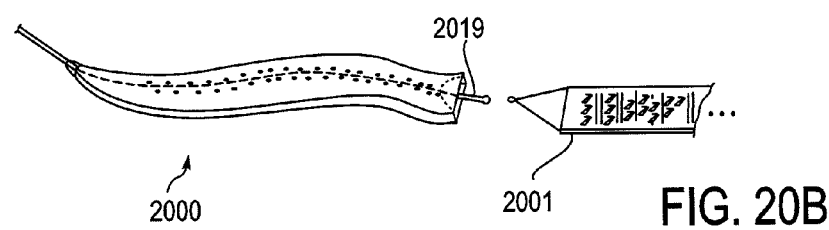

As mentioned above, the NLR device described herein may couple to one or more tissue modification devices. FIGS. 20A and 20B illustrate two examples of NLR devices 2000 that are configured to couple to tissue modification devices 2001. In FIG. 20A, the tissue modification device 2001 is an elongate flexible tissue removal device that includes tissue modification elements 2003 (e.g., "teeth") on one side, and has a coupling element at the distal end 2005. The coupling element may be a guidewire coupler, or it may be configured to couple directly to an NLR device 2000. The NLR device 2000 (shown adjacent to the distal end of the tissue modification device in FIG. 20A) includes an opening or cavity into which the tissue modification device may at least partially enter and engage. In other variations, the proximal end of the NLR device is configured to couple to the distal end of the tissue modification device without entering the NLR device.

The NLR device in this example may therefore be configured as a sock or sleeve that fits over the tissue modification device. In this example, the NLR device includes at least a first (top or upper) surface that includes one or more electrodes, such as a network of electrodes 2011 as described above. The NLR device and/or tissue modification device may be configured so that that two are oriented relative to each other when they are engaged. For example, the NLR device may be coupled with the tissue modification device so that the tissue modifying elements 2003 face the same direction as the first (top) surface. In some variations, all or a substantial portion of the tissue modification device may fit within the NLR device. In the example shown in FIG. 20A, the NLR device attaches to a guidewire 2020 at the distal end of the NLR device 2015. In some variations, the NLR device engages the tissue modification device which is attached at the distal end to the guidewire, and the guidewire 2019 passes through the NLR device, as illustrated in the example shown in FIG. 20B. In this example the NLR device is configured as a sleeve which at least partially covers the tissue modification device. The sleeve may be a 'break away' sleeve, so that it can be removed (e.g., unpeeled) from the tissue modification device after it has been used to position, or to confirm the position, of the tissue modification device.

Figure 21A:
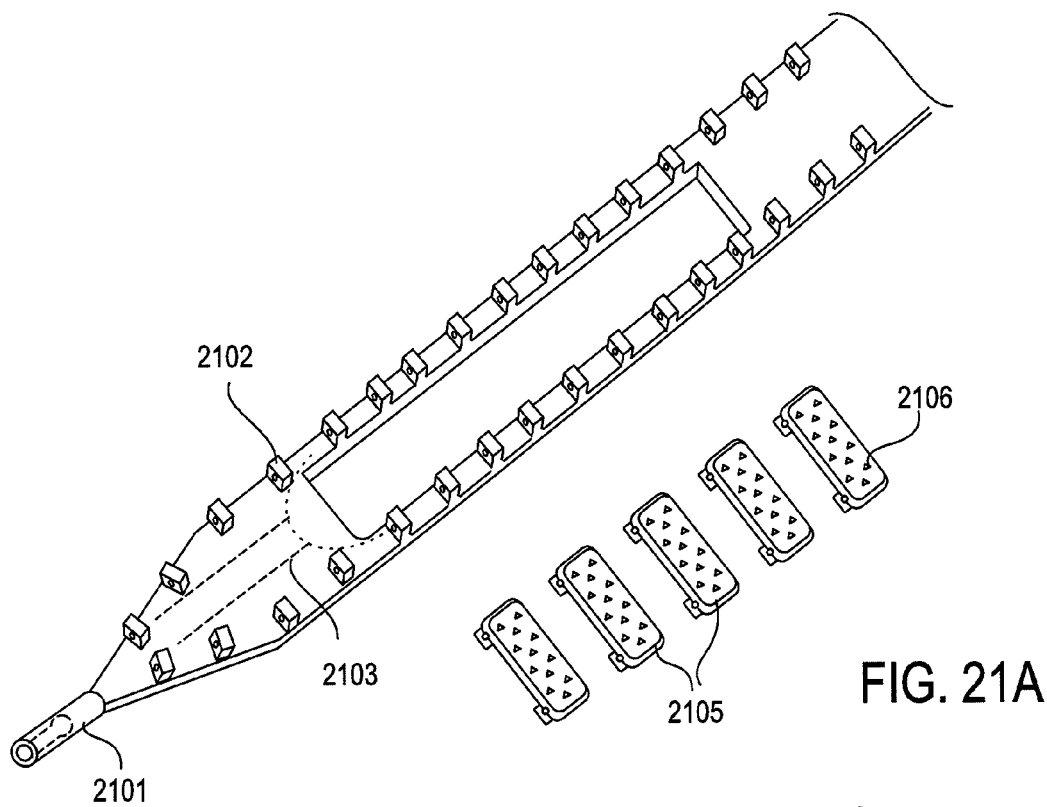
FIGS. 21A and 21B are semi-exploded views of devices including an NLR region at the distal end.
Figure 21B:
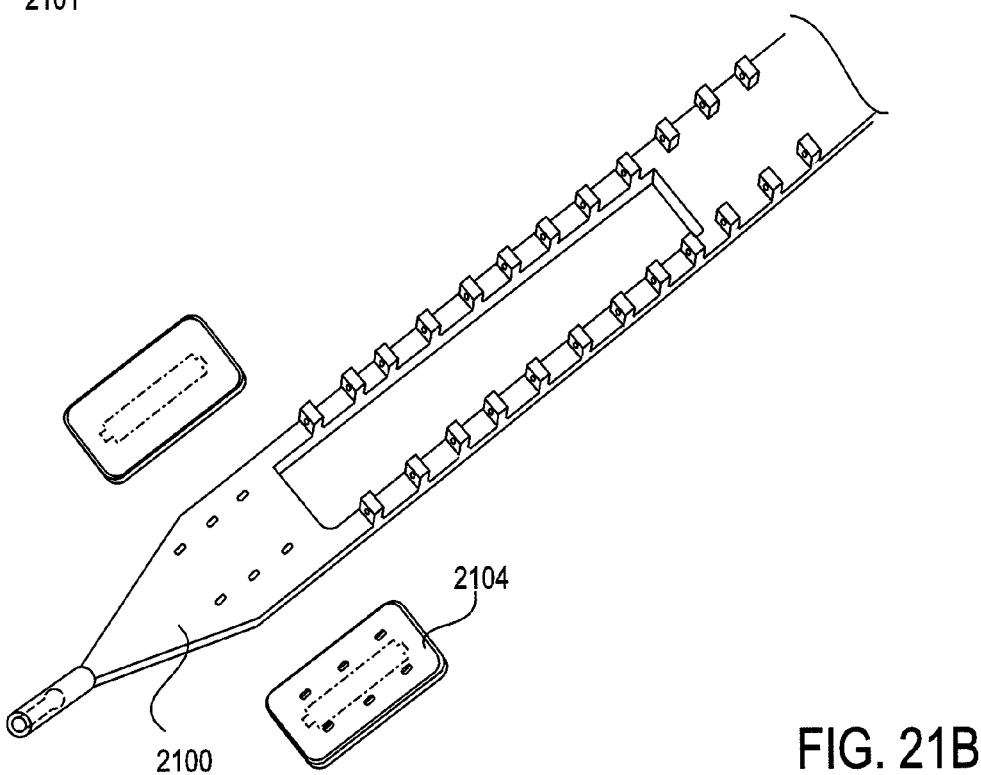

FIGS. 21A and 21B illustrate variations in which the NLR device is incorporated into a tissue modification device. For example, in FIG. 21A, the distal end of the device includes an NRL region 2103. Distal to the NLR region is a connector 2101 configured to releasably connect to a guidewire. The body of the device includes ferrules 2102 recessed from the cutting surface. The ferrules may act as guides along which one or more cables (not shown) may extend. The cables may hold one or more rungs 2105 that are configured to have tissue modification elements 2106, such as blades or teeth for cutting tissue. In FIG. 21A, the NLR region may include a plurality of electrodes, as described above. These electrodes (e.g., bipoles) may be formed from a conductive line or lines embedded in the body of the device, or from a flex circuit attached to the distal end, or from a lumen filled holding an electrically conductive element (e.g., wires) to which vias filled with a conductive material (e.g., epoxy) connect.

FIG. 21B illustrates a variation in which the NLR region is formed of one or more flex circuits. In FIG. 21B, the flex circuits 2104 snap together through a thinner region of extrusion. The flex circuits (e.g., printed on a flexible material) may then be connected to one or more connectors on or in the body of the device 2100. In general, devices such as these, which include an NLR region and a tissue modification region, may be also referred to as "NLR" devices.

Figure 21C:
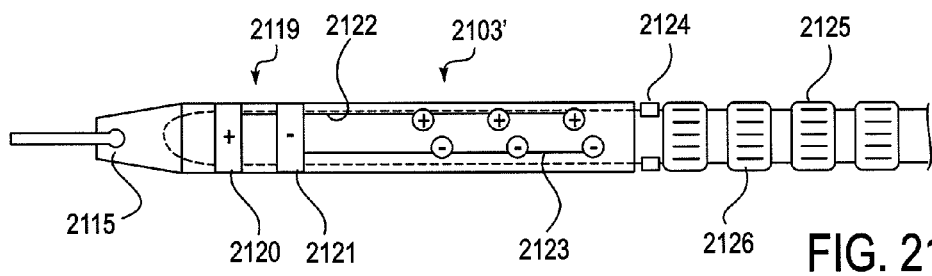
FIG. 21C shows a variation of an NLR device configured to be powered from the distal end.

In any of these variations, the power may be connected to the electrodes through the conductors (e.g., wires, conductive material) extending proximally to a controller and/or power supply located proximally. In some variations the conductor supplying power to the electrodes may be part of the cable. Alternatively, the power supply may be separate from the cables. FIG. 21C illustrates an example of an NLR device in which power is supplied from the distal end, rather than the proximal end.

In FIG. 21C, the flexible, elongate and ribbon-shaped NLR device includes a coupler 2115 (e.g., guidewire coupler) at the distal end, and proximal to that, two power 'pads' or connectors 2119 to which the power supply for powering the device may be clipped to provide power to the NLR region of the device. For example the connectors may include an anodal connector 2120 connected to an anodal wire 2122 and a cathodal connector 2121 connected to a cathodal wire 2123. In this example, the distal end of the NLR device is pulled distally until the power connectors 2119 are accessible from the distal end. For example, the distal end of the NLR device may be pulled distally until the power connectors 2119 extend through the patient's skin. Thus, the region between the power connectors 2119 and the electrodes of the NLR region 1203' may be sufficiently long (e.g., inches) so that the NLR region can be positioned near the target tissue (e.g., the tissue of the neural foramen) while providing access to the power connectors.

The power supply may be connected to the power connectors 2119 by one or more clips (e.g., clip on electrodes). The connectors 2119 may be configured as plugs, or any other connector, and may be configured to mate with connectors from the power supply or power controller (not shown).

FIG. 21C is also another example of a device having an NRL region 2103' and a tissue modification region 2125 (having blades 2126); these two regions are separated by optional blocks or crimps 2124 that prevent axial loads or tension when the devices are actuated (e.g., by urging against the tissue). As described above, in some variations an NLR device is coupled to a tissue modification device to form a combined NLR device, similar to the example shown in FIG. 21C. The connection between the two devices may be releasable connections, such as the guidewire connectors. Furthermore, these connectors may be configured to withstand the axial loads applied when the tissue modification devices are urged against the tissue.

Systems

Any of the devices described herein may be used as part of a system, which may be referred to as a nerve localization system or NLR system. Systems may include components (e.g., hardware, software, or the like) to execute the methods described herein.

Many of the devices described herein may be used with a guidewire for either or both positioning of the device and operation of the device. Thus, many of the devices include guidewire management features to help position, orient, grasp, and regulate the guidewire. Guidewire management may help with the correct operation of the device, and may decrease the risk of misuse of the device and prevent harm to the operator (e.g., surgeon or other medical professional).

The guidewire, as described throughout, is typically long (e.g., elongated) and flexible, and may have a sharp (tissue penetrating) distal end and a proximal end that allows it to be coupled to a guidewire coupling member securely. Similarly, the proximal end of the guidewire may be configured to pass through a probe or introduction device so that the probe may be removed from over the proximal end of the guidewire during operation.

Figure 22A:
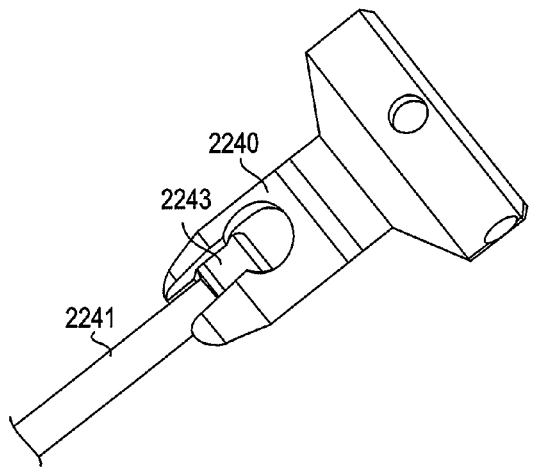
FIG. 22A illustrates a detail view of a guidewire coupler and a proximal end of a guidewire.
Figures 22B, 22C, 22D:
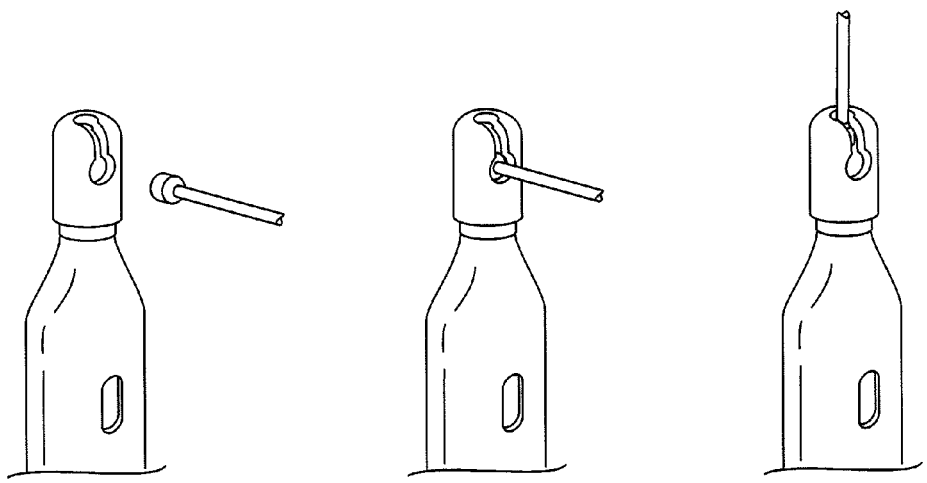
Figure 23A:
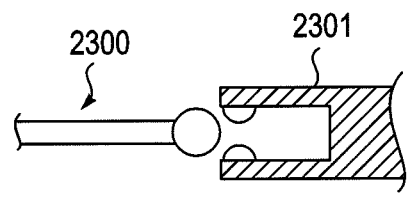
Figure 23B:
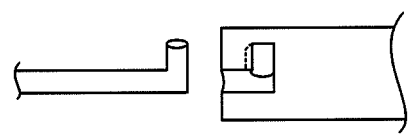
Figure 23C:
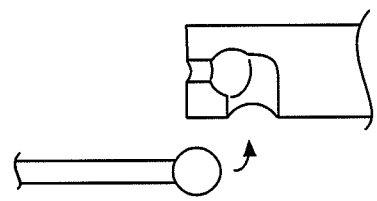
Figure 23D:
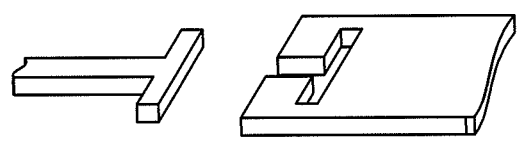
Figure 23E:
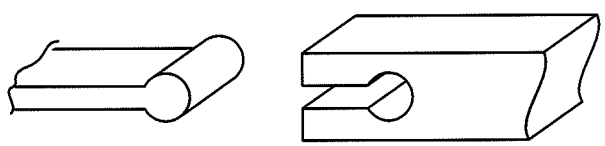
Figure 23F:
Figure 24A:
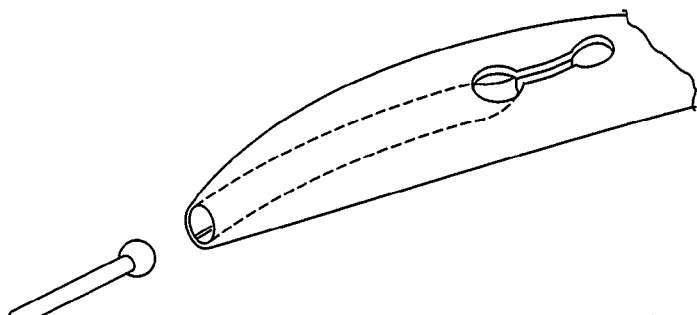
FIG. 24A shows one variation of a guidewire lock.
Figure 24B:
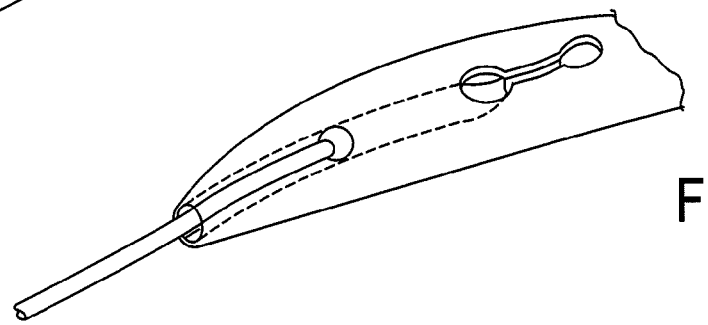
FIGS. 24B-24E illustrate one method of using the guidewire lock shown in FIG. 24A.
Figure 24C:
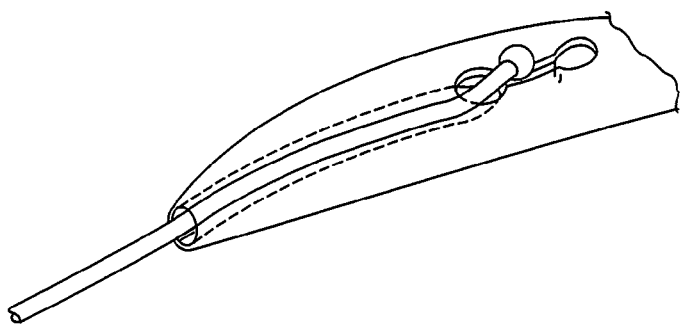
Figure 24D:
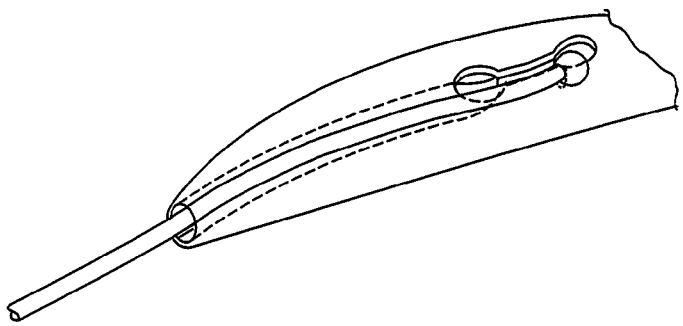
Figure 24E:
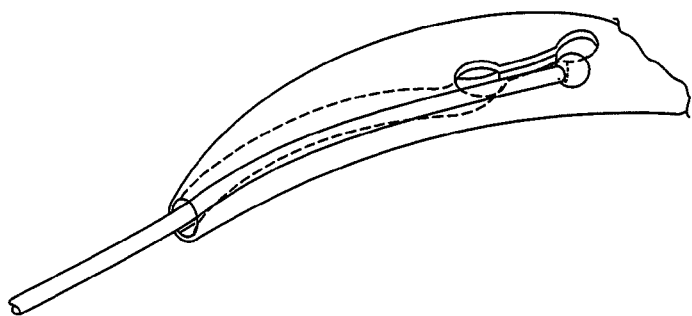

FIG. 22A shows a side perspective view of the guidewire connector 2240, within which a guidewire 2241 has been connected. The proximal end of the guidewire 2241 includes a cap or end piece 2243 having a slightly larger diameter than the rest of the guidewire. This end piece 2243 may reliably engage the connector 1640 by fitting into an opening in the side of the connector and sliding into an engaged position within the connector. FIGS. 22B-22D illustrate one method of connecting a proximal end of a guidewire to a distal end of a device, such as a NLR device and/or a tissue modification device. To engage, the proximal guidewire is held substantially perpendicularly to the device having a guidewire coupler at the distal end. In some alternative variations, the guidewire may be positioned at an acute angle to the coupler, such as 45 degrees, or alternatively, the guidewire may be positioned at an obtuse angle to the coupler such as 100 degrees. The guidewire may be positioned at any suitable angle to the guidewire coupler. Once the guidewire is positioned with respect to the coupler, the guidewire is advanced toward the coupler such that the proximal shaped end of the guidewire is placed within the shaped recess of the coupler, as shown in FIG. 22C. Once the proximal end of the guidewire is placed within the coupler, the guidewire is rotated with respect to the coupler such that the guidewire is now in-line with the coupler and the device (i.e. positioned at 180 degrees with respect to the device).

As shown, the guidewire coupler is configured such that a guidewire and the guidewire coupler may connect in an end-to end configuration. Furthermore, the device having the guidewire coupler can be pulled into position by pulling on the guidewire while the proximal end region of the guidewire is held stationary by the guidewire coupler with respect to the distal end region of the elongate body. For example, the guidewire does not move longitudinally within the guidewire coupler. The guidewire coupler is further configured such that the device and guidewire, when coupled, can be pulled and pushed distally or proximally without uncoupling the guidewire from the guidewire coupler. Furthermore, the guidewire and/or the proximal end of the device can be pushed down or pulled up also without uncoupling the guidewire from the guidewire coupler. The guidewire coupler may be configured to withstand a large amount of force (e.g., enough force to modify tissue such as bone and cartilage). The coupling mechanism and guidewire may be configured to withstand forces within the range of 10 lbs to 60 lbs. For example, the coupling mechanism and guidewire may be configured to transmit up to 40 b of force, up to 50 lb of force, up to 60 lb of force, up to 100 lb of force, etc.

FIGS. 23A-29C illustrates alternative connectors (e.g., guidewire connectors) that may be used with any of the devices described herein. For example, FIGS. 23A-23F illustrate alternative embodiments of these guidewire connectors, including a push lock variation (FIG. 23A), in which the guidewire 2300 is pushed into the distal end of the connector 2301 and is locked or held in place; a top rotating lock variation (FIG. 23B) similar to the variation shown in FIG. 22; and a side rotating lock (FIG. 23C). FIGS. 23D-23F illustrate key lock top variations (where the "top" may refer to the first surface of the NRL device), key lock side variations, and twist lock variations, which may be threaded.

FIGS. 24A-24E illustrate another variation of a connector for a guidewire. FIGS. 24B-24E illustrate how the connector is engaged and locks to a guidewire and illustrate one variation of a "retroflex" unlocking and disengagement of a guidewire from a connector. In this example, bending or flexing the portion of the device including the connector causes it to unlock. This is also illustrated in FIGS. 25A-25F for another type of connector.

Figure 25A:
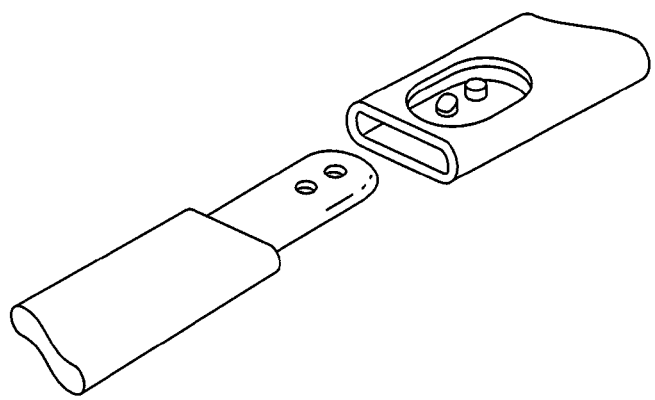
FIG. 25A is another variation of a guidewire lock which may be used with any of the devices and systems described herein.
Figure 25B:
FIGS. 25B-25D illustrate one method of using the guidewire lock shown in FIG. 25A.
Figure 25C:
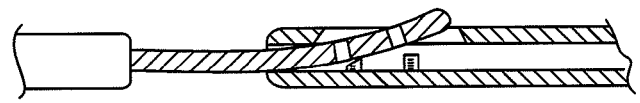
Figure 25D:
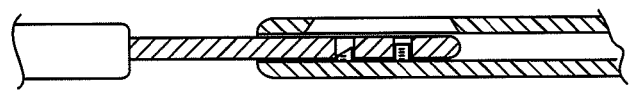
Figure 25E:
FIGS. 25E-25F illustrate a method of unlocking the guidewire lock shown in FIG. 25A.
Figure 25F:
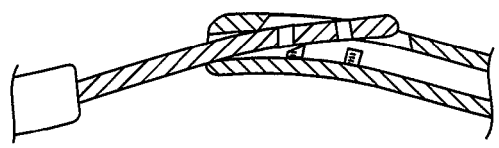
Figure 26A:
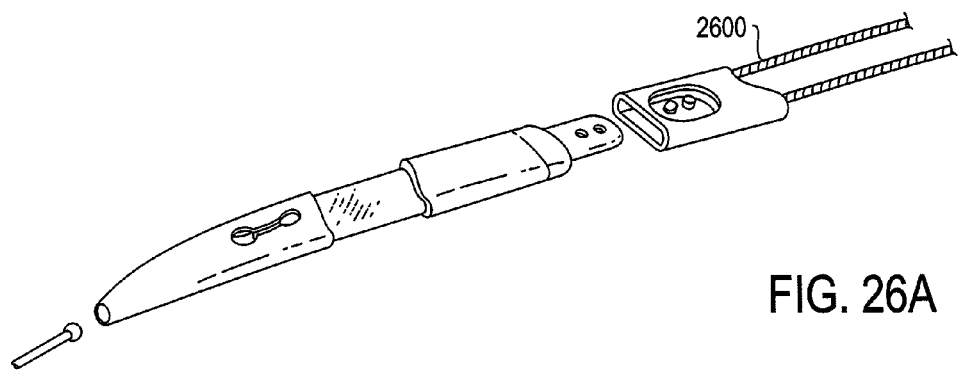
FIG. 26A is another variation of a guidewire lock or coupler, configured as a leader.
Figure 26B:
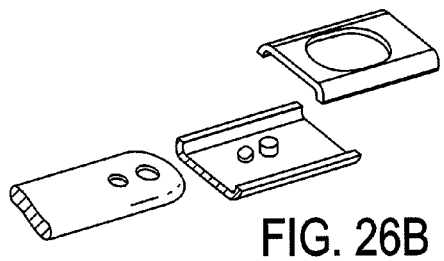
FIGS. 26B and 26C show exploded views of different regions of the guidewire coupler shown in FIG. 26A.
Figure 26C:
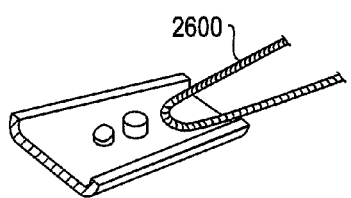
Figure 27A:
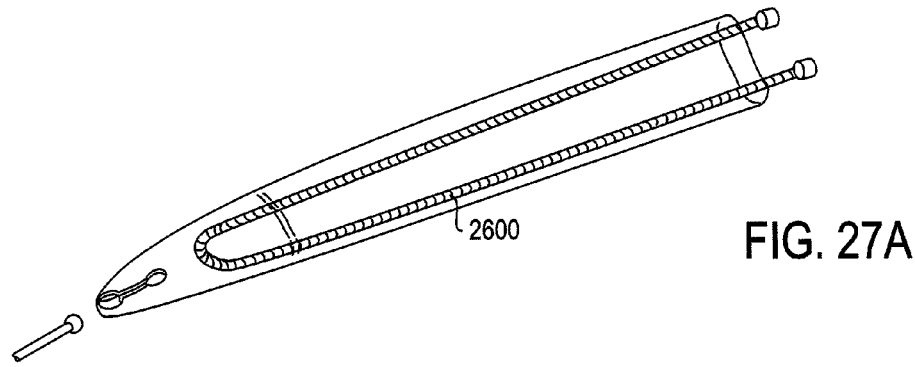
FIGS. 27A and 27B illustrate one variation of a device (e.g., an NLR device) including a connector and guidewire coupler.
Figure 27B:
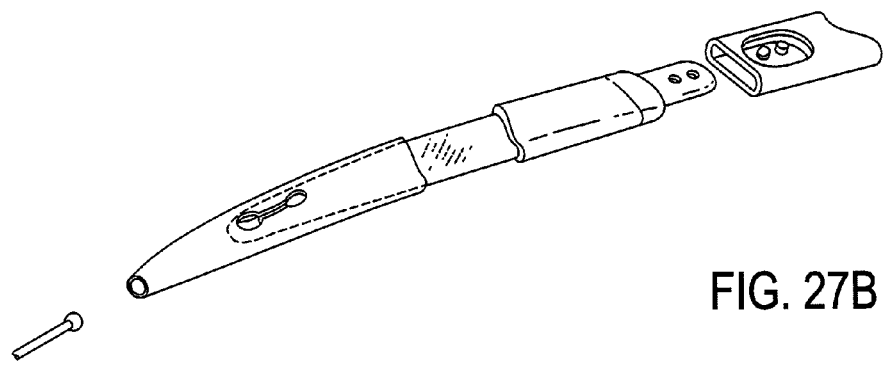
Figure 28A:
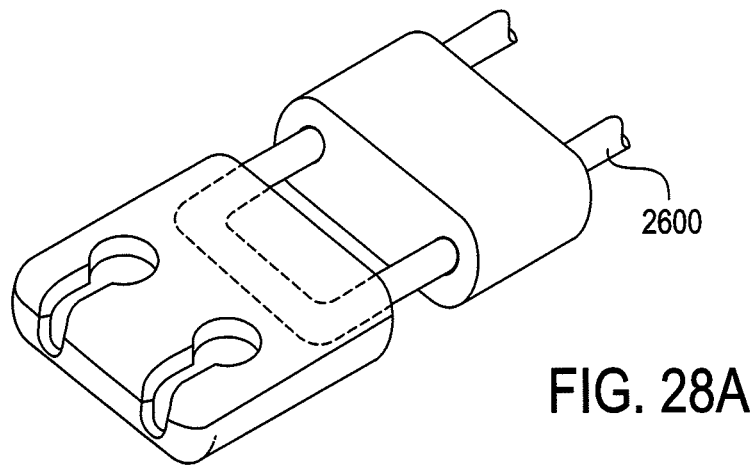
FIGS. 28A-28C show another variation of a coupler.
Figure 28B:
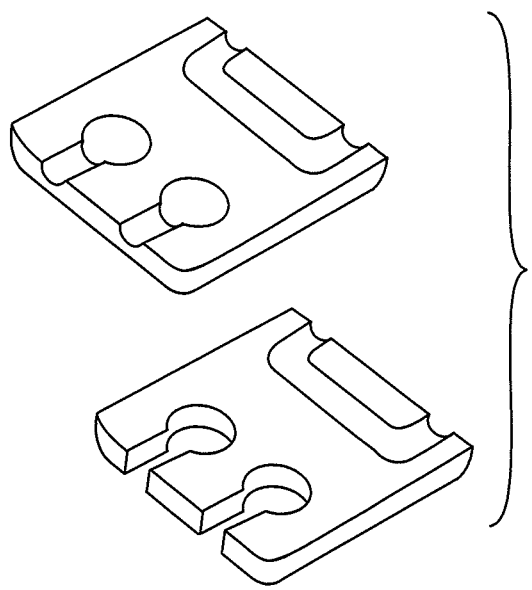
Figure 28C:
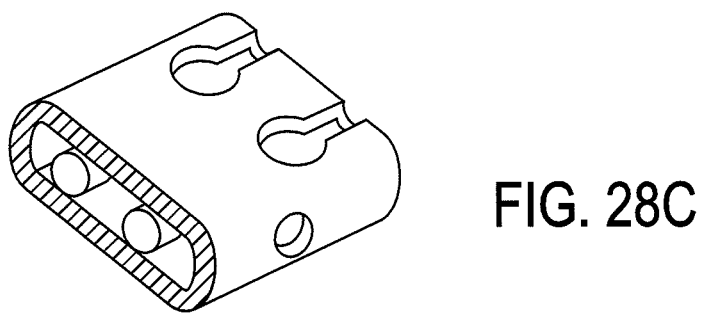
Figure 29A:
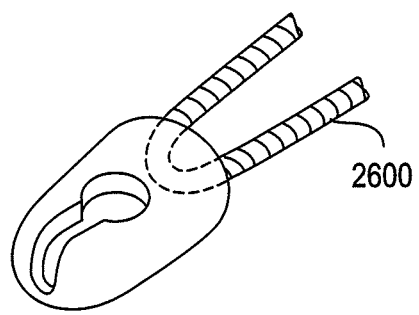
FIGS. 29A-29C show another variation of a guidewire coupler.
Figure 29B:
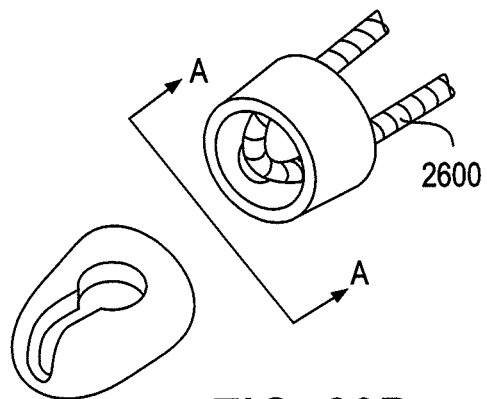
Figure 29C:
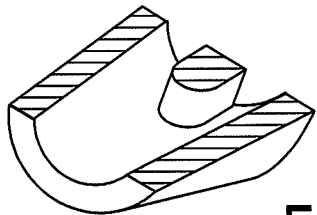

In addition to the guidewire connectors shown above, in some variations of the NLR devices described herein, a connector may be configured as a substrate connector. FIG. 25A illustrates on variation of a substrate connector. For example, a substrate connector may be used to connect an NLR device to a tissue modification device. FIGS. 26A-26C illustrate another variation of a connector, including a retroflex leader that may be used to connect the devices described herein (including tissue modification devices) to other portions of the device or system. FIGS. 27-29C show enhanced view of these different regions of the connector, and devices including these connectors.

Figure 30:
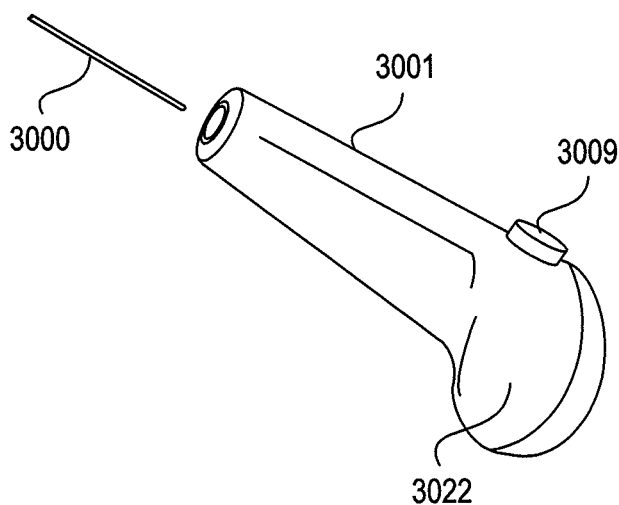
FIG. 30 is one variation of a distal handle configured to couple to a distal end of a guidewire.

The distal end of the guidewire 3000 (which may be sharp in some embodiments) may be fed into a distal handle 3001. FIG. 30 illustrates a distal handle 3001 that may be attached to the distal end of a guidewire 3000, and may be included as part of the systems described herein. For example, FIG. 30 shows one variation of a distal handle 3001, including a central passageway through which the guidewire may be passed, and including a lock for locking the guidewire within the passageway. The handle may also include a guidewire capture chamber 3022 for securing the (typically sharp) distal end of the guidewire which may otherwise pose a danger to the user. In this variation the guidewire handle may slide over the distal end of the guidewire, and then the guidewire may be looped through the guidewire capture chamber and be locked in position so that the handle may then be used to apply force to pull the guidewire distally (and thereby manipulate any of the devices described above, that may be coupled distally to the proximal end of the guidewire.

This variation also includes a control 3009 (shown as a button) that may control the locking/unlocking of the guidewire in the handle. For example, the button may be pushed to unlock the guidewire, allowing it to be advanced into the handle, or withdrawn from the handle. In some variations, the control may be pressed or activated continuously to unlock (e.g., maintaining the hold on the button), while in other variations the control may be engaged to remain either locked or unlocked.

Variations and Methods of Use

In general, any of the variations of the neuro localization devices described herein may be used as described above to determine (or check) if a nerve is on one side or the other of the ribbon-shaped device. Described below are examples of methods of operation, as well as variations and embodiments of neuro localization devices. Any of the methods and features described herein may be used in combination with any of the other methods and features described, except where the context makes clear that the features or combinations cannot be combined.

In particular, described herein are devices (e.g. NLR devices and tissue modification devices) and systems including these devices that are configured for use together as a system. For example, the devices described herein may all be coordinated so that they may function together, and may include markings, orienting structures and other features that are common between the different devices within the system. In some variations the devices all include front/back, top/bottom, or other orientation structures on the handles of the devices. The handles may be structured in common.

The devices described herein may include handles that allow the devices to be hand operated using one hand or two hands (or both). In some variations the proximal handle portion of the NLR device may be configured for improved operation, including an indication of what portion (e.g., what side) of the neural localization device is being activated, the orientation of the distal end of the neural localization device, and/or a control for controlling stimulation provided by the neural localization device.

Figure 31A:
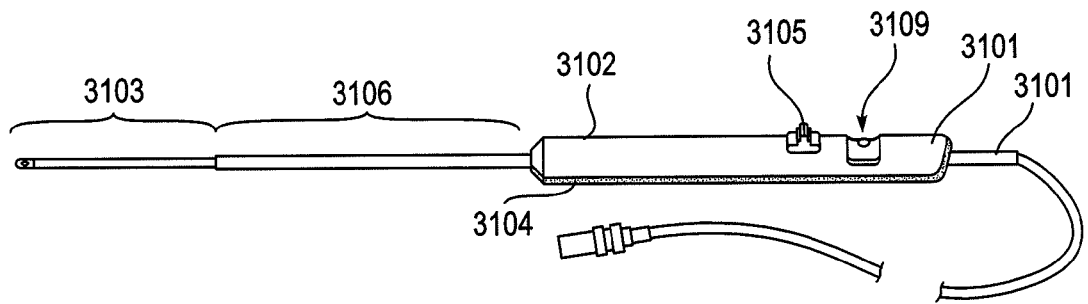
FIG. 31A shows one variation of a neural localization device.
Figure 31B:
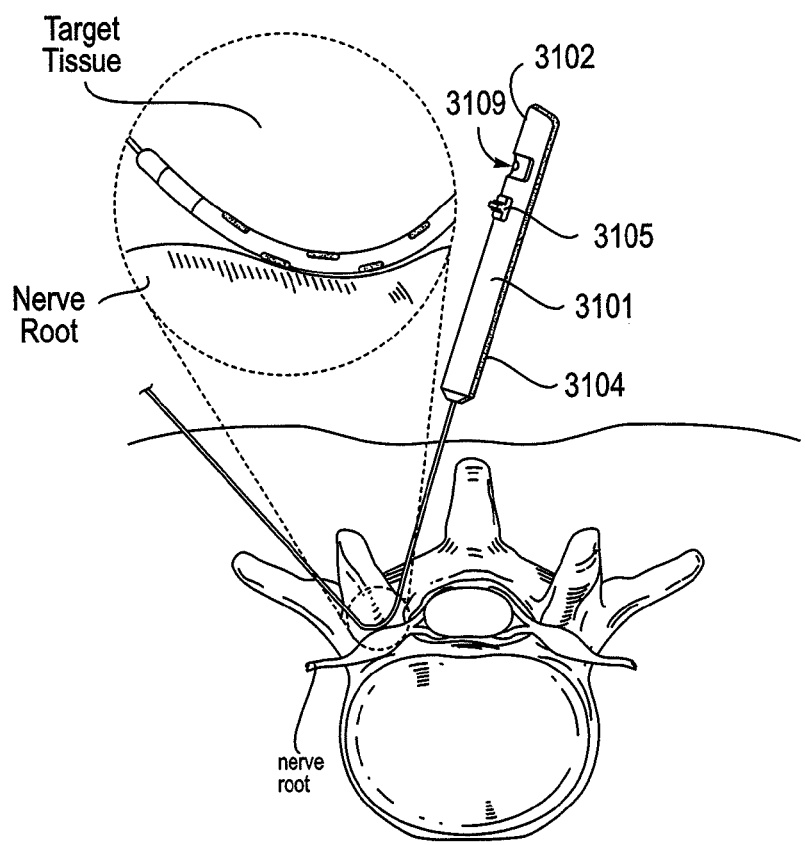
FIG. 31B illustrates the neural localization device of FIG. 31A coupled to a guidewire and positioned within a neural foramina, above a spinal nerve root.

For example, FIGS. 31A-31C illustrate a handle 3101 of a neural localization device. In this example, the handle includes a window 3109 on one or more sides of the device that indicates visually where and when stimulation is being applied. For example, as shown in FIGS. 32A-32C, a window may indicate "top" (FIG. 32A), "bottom" (FIG. 32B), and/or "off" (FIG. 32B). As shown in FIG. 32A, the white square 3110 indicates that the white surface, also the top surface, is selected for activation. As shown in FIG. 32C, the black square 3111 indicates that the black surface, also the bottom surface, is selected for activation. As shown in FIG. 32B, the circle 3112 indicates that no surface is selected for activation and/or that the device is off. The window may alternatively show other suitable indicators such as a graphic, including a color, an alphanumeric message, a symbol, or the like. The handle also includes a control 3105 (shown here as a slider) for toggling stimulation between the back and front; the control may also be used to turn the stimulation "on" or "off" and in some variations can also be used to determine the level of stimulation.

FIG. 31A is one variation of a neural localization device. As described above, the device includes a flexible distal end that includes a guidewire coupling member at the distal end. The flexible ribbon-shaped distal end region 3103 has an upper first region with a plurality of electrodes arranged along the length, and a lower second region with a plurality of electrodes arranged along the length. The device also includes a rigid more proximal region 3106, and a proximal handle with at least one control 3105 for selecting the upper or lower surfaces (or both) of the flexible ribbon region for activation or simulation.

This neural localization device may be used to identify which side of the device motor nerves are on as part of the spinal surgery. Any of the neural localization devices described herein may be used as part of a spinal decompression procedure. For example, the device (which may be used in either or both monopolar and bipolar modes) may be connected to an EMG intra-operative neuromonitoring stimulus output box that provides power to the electrodes on the device. In this example, the EMG system may be set to output the following stimulus settings:

TABLE 3

Neural Localization Ribbon Stimulus Conditions

| | Frequency | Pulse Width | Output Current |
| --- | --- | --- | --- |
| Useable Ranges | 3.13-5.00 Hz | 150-300 μs | 0.5-30 mA |
| Recommended Stimulus Settings | 4.13 Hz | 300 μs | 0.5-30 mA |

These operation parameters are exemplary only, and other or additional stimulation parameters may be used.

The neural stimulation device may be used to stimulate either the dorsal or ventral device surfaces (e.g., "top" or "bottom" of the ribbon structure). A control (e.g., the slider switch 3105 on the handle) may be used to determine the stimulation surface (top/bottom) and/or the mode (monopolar/bipolar, etc). In the example shown in FIGS. 32A-32B, an indicator on the handle indicates the mode of operation. For example, as described above, with the white field visible through the device window, stimulation occurs at the electrodes corresponding to the white (e.g., dorsal) surface of the device. When the all black field is visible, stimulation is active on the corresponding black (e.g., ventral) surface of the device. When the circle is visible, the device does not transmit current (off state).

Once the device is positioned (e.g., pulled into position as mentioned above), as illustrated in FIG. 31B, stimulation may be applied by stimulating the white or dorsal/posterior surface 3102 of the ribbon-shaped device. This may be accomplished by sliding the switch 3105 until the white field is visible, as illustrated in FIG. 32A. The current may then be slowly increased (e.g., from 0 mA up to 30 mA) until an EMG response is attained. As mentioned above, other appropriate responses may be monitored (e.g., muscle twitch, direct electrical recording of nerve activity, etc.). Once the threshold EMG stimulation is achieved, the user may manually (or the system may automatically) note the required threshold stimulation current, and then the current may be reduced back down (to 0 mA).

The control may then be set to stimulate the opposite side of the flexible ribbon-shaped device (e.g. the black or bottom/anterior surface 3104), e.g., by sliding the switch until the black field is visible in the window in the example illustrated in FIG. 32C. Again, the stimulation may be slowly increases (e.g., increasing the current from 0 mA to 30 mA) until a threshold response (e.g., an EMG response) is elicited. Current applied may then again be reduced back to 0 mA.

The required threshold stimulation current may be a minimum current required to elicit any EMG response at all (most likely the lowest measureable EMG response), or may be the minimum current required to elicit a predetermined EMG response. This method may be desirable as it may require generally lower current levels being delivered to the nerve root. Alternatively, the amount of current delivered to the NLR device may be held constant and the resulting EMG response may be measured and compared. For example, the NLR device may automatically deliver a current of 30 mA to the top surface and then deliver a current of 30 mA to the bottom surface. The resulting EMG response may then be measured for both the top surface and then the bottom surface, respectively.

If the stimulation suggests that the nerve is above the Ribbon (i.e. nerve has been inadvertently "hooked" and could be damaged when modifying the tissue by pulling a tissue modification device dorsally), this may be an indication that the neural stimulation device and guidewire should be removed, and repositioned by re-inserting and repositioning the probe (described above) and then repeating the stimulation sequence just described until stimulation suggests that the nerve is below the ribbon-shaped device.

The stimulation may suggest the location of the nerve root with respect to the NLR in any number of ways. For example, in a first variation, the threshold stimulation current for the top surface and the threshold stimulation current for the bottom surface may be compared. For example, if the top threshold stimulation current is larger than the bottom stimulation current, the nerve root is most likely below the NLR device, adjacent to the bottom surface. This may be true because when the nerve root is closer to a surface, it will take a lower amount of current from that surface to activate the nerve and elicit an EMG response from that nerve. As described above, is the current delivered is held constant, the resulting EMG responses for the top and bottom surfaces may be compared. A larger EMG response will most likely indicate that the nerve is located adjacent to that side of the device.

In a second variation, a ratio of the first threshold current to the second threshold current may be calculated and used to determine the likelihood that the nerve is on one side or the other of the pathway around the target tissue taken by the neural localization device. For example, if the threshold stimulation current for the top surface is 19 mA, and the threshold stimulation current for the bottom surface is 6 mA, a ratio of 19/6=3.17 may be calculated. In some embodiments, a minimum ratio may be required to indicate that the nerve root is below the NLR device and the tissue modification procedure may be safely carried out. For example the minimum ratio may be equal to 2. In this example, the ratio calculated above (3.17) is greater than 2, and the stimulation would therefore suggest that the nerve root is below the NLR device and that the tissue modification procedure may be safely carried out.

Figure 33A:
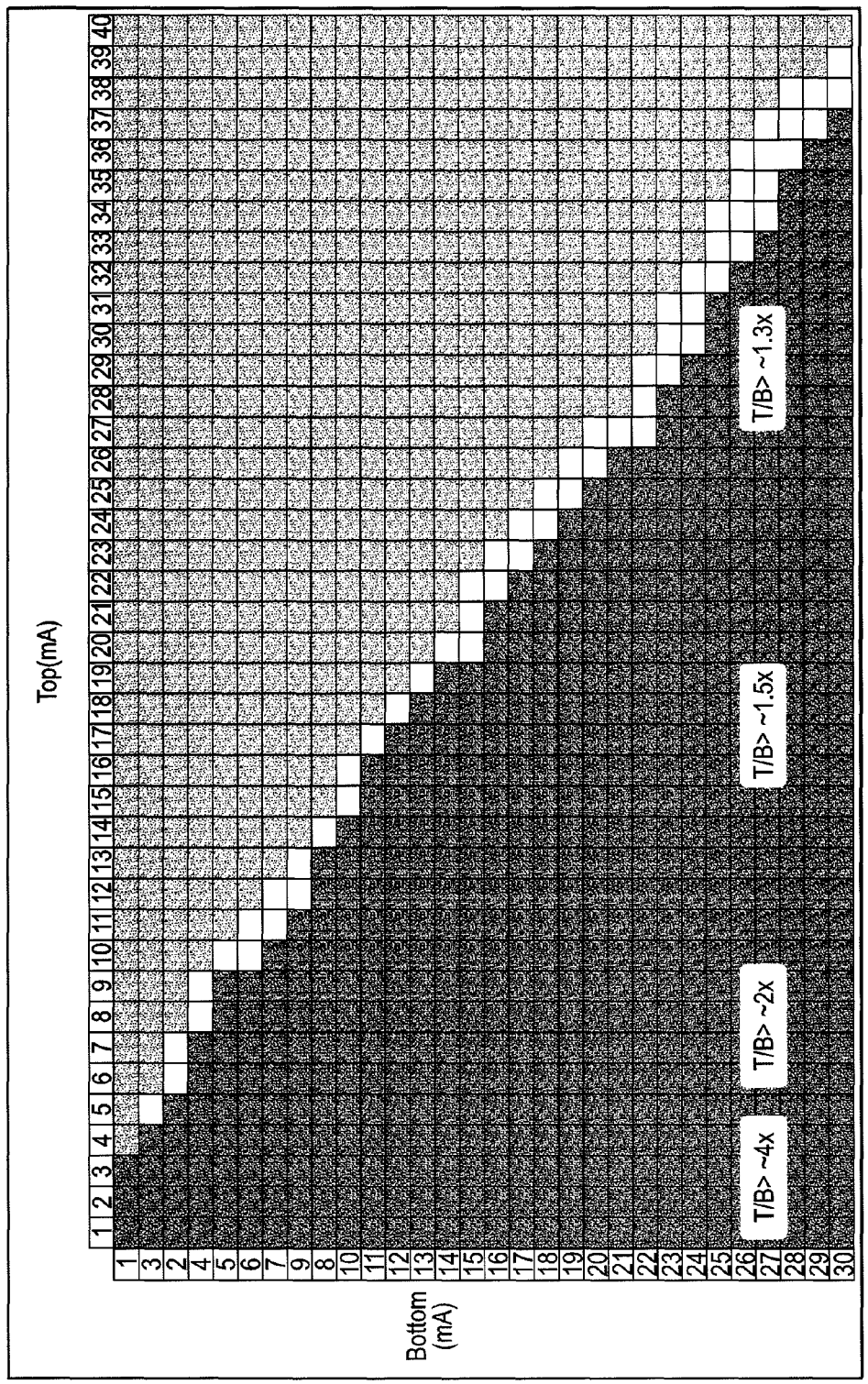
FIGS. 33A and 33B graphically depict various relationships between threshold stimulation current values relative to a neural localization devices position along a pathway through a patient's body.
Figure 33B:
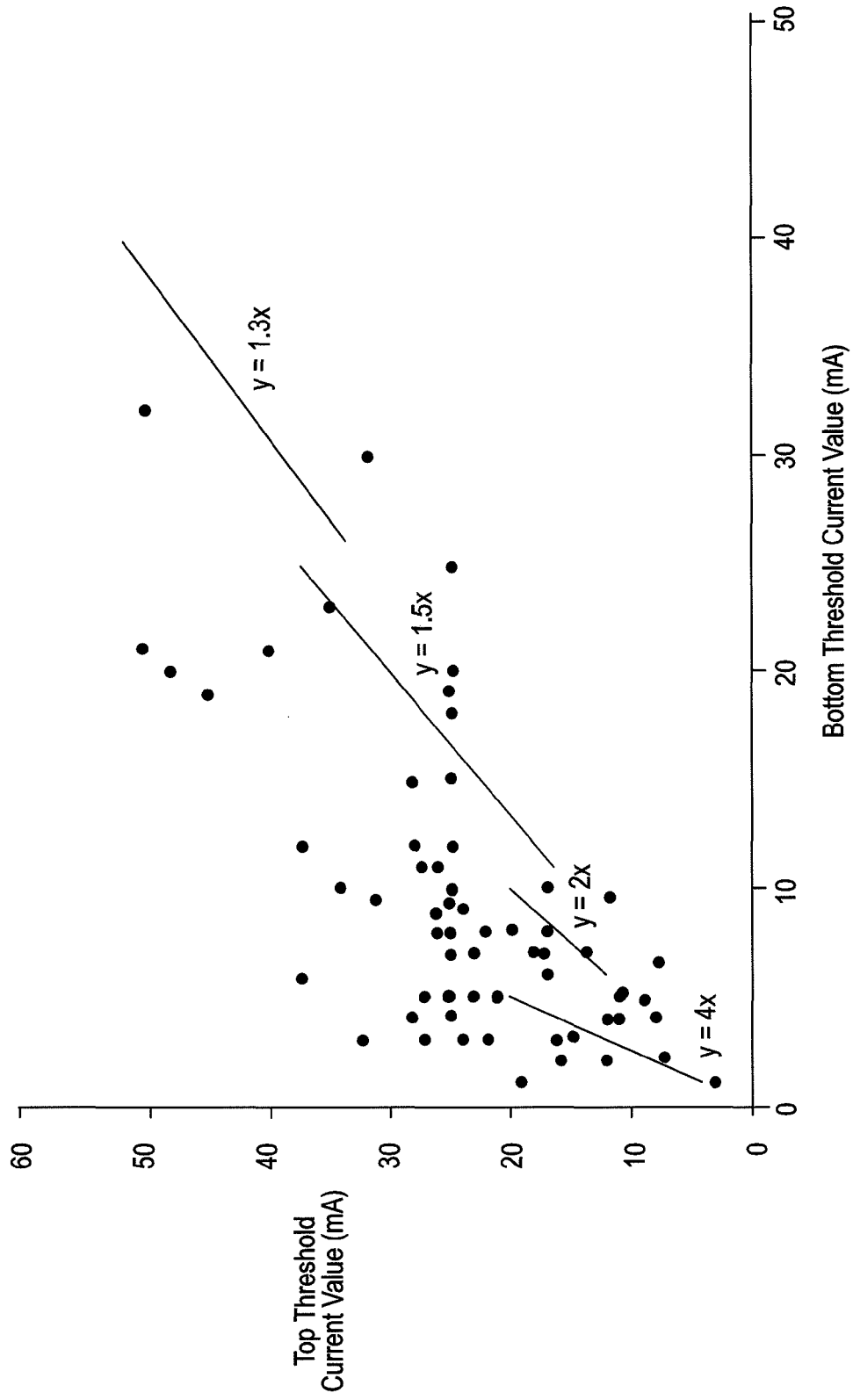

Alternatively, the minimum ratio required may be referenced to a range of values for the magnitude of one or the other of the threshold current values. For example, the minimum required ratio may be smaller for larger values of the top threshold current value. For example, as shown in FIG. 33A, if the stimulation of the NLR device indicated a threshold current value for the top surface of 9 mA, the threshold current value for the bottom surface should be greater or equal to 4 mA and preferably greater or equal to 5 mA. As shown, the minimum ratio may be about equal to 2 when the threshold current value for the top surface is between 6 mA and 10 mA (inclusive). Alternatively, if the stimulation of the NLR device indicated a threshold current value for the top surface of 28 mA, the threshold current value for the bottom surface should be greater or equal to 22 mA and preferably greater or equal to 24 mA. As shown, the minimum ratio may be about equal to 1.3 when the threshold current value for the top surface is between 26 mA and 40 mA (inclusive). As shown in FIG. 33B, the plot includes exemplary actual data accumulated with an NLR device. Each data point indicates a top threshold current value and a bottom threshold current value where the stimulation suggested that the nerve root was below the NLR device and the tissue modification procedure was safely carried out. As shown by the data, the trendlines indicate preferred minimum ratios (y=top threshold value to x=bottom threshold value) above which the stimulation may suggest that the nerve root is safely below the NLR device.

FIGS. 33A and 33B illustrate specific examples. Alternatively, the minimum ratio may vary with the threshold current value for the top surface or the threshold current value for the bottom surface in any other appropriate relationship, including curve fitting to data such as that shown in FIGS. 33A and 33B.

Once nerve localization is achieved, the stimulus signal may be turned off, and the neural localization device pulled dorsally (pulling the guidewire back through the tissue from the distal end) so that the NLR device can be disengaged and removed, leaving the guidewire in place.

As mentioned, a neural localization device may be used as part of a spinal decompression procedure to remove impinging material (e.g., bone, disc, etc.) from a spinal neural foramen, without cutting through the bone completely. As illustrated in FIG. 34A, any one of a number of different pathways through the neural foramen may be chosen. For example, the path through the spine may be an "above the pedicle pass" (as indicated by arrow 3401) so that the guidewire may pull in the NLR device tangential to the direction of the exiting spinal nerve root 3400. The path may also be parallel to the exiting nerve root 3403 (e.g., "below the pedicle pass" as indicated by arrow 3402). The guidewire may be positioned using one or more probes or needles, including curved or curvable probes, as previously described. Once the guidewire is positioned through the spinal foramen (e.g., around the pedicle), the position of the nerve or nerve root relative to the path taken by the guidewire may be confirmed using any of the neural localization device described herein. This confirmation of position is particularly important in spinal decompression procedures in which a flexible tissue modification device is pulled into position by the guidewire because of the risk of "hooking" the spinal nerve root with the guidewire; this means that the path taken by the guidewire through the compressed spinal foramen passes under or around the nerve root so that the nerve root is located dorsal or posterior to the nerve root. In this case, the application of bimanual force on the proximal and distal ends of a tissue modification device (e.g., a cutting device) may cause the tissue modification device to cut through the tissue and harm the patient.

Confirmation of the relative position of a nerve, particularly the spinal nerve root, as described herein, is particularly difficult given the many different pathways through the same neural foramen that the devices may take. This is illustrated by the different arrows (labeled 1-3) in FIG. 34B. For example, the safest path along which to deliver the NLR device may be along path 1 because it may be the easiest path along which to deploy an introduction probe and/or it may be the most difficult path along which to inadvertently hook the nerve root—it can be seen in FIG. 34B that the nerve root 3400 is far from path 1. However, it may be difficult to stimulate the nerve root and elicit an EMG response for that same reason. In this example, it may be advantageous to deliver the NLR device along path 1 and then once the NLR device is in position, the device may be turned or torqued such that the stimulation region is moved toward the nerve root 3400. This may be done by a stiffened region along the elongate body that can deliver a force from the proximal and/or distal handle or alternatively, the elongate body may be shape changing as described above to moved toward the nerve root to be stimulated.

The neural localization devices described herein may be configured to emit only a relatively 'weak' current (or field) so that the nerve may be localized as either above or below the neural localization device. The lower energy applied here may also prevent unnecessary and undesirable stimulation and/or damage to the tissue. Thus, if the device is not positioned sufficiently close to the nerve (e.g., spinal nerve root), stimulation of the top and/or bottom of the device may not resolve the relative location of the nerve.

As described above, and as shown in FIG. 35, the NLR elongate body may include radioopaque markers 3502 and 3503 that may be used help localize and accurately position the NLR device, particularly the stimulation region 3501 of the device. For example, the NLR device may include one or more radio-opaque regions that can be used to orient or mark the device. As shown in FIG. 35, the region of the NLR device in which the electrodes 3500 extend may be referred to the active region or the stimulation region 3501. The stimulation region 3501 in this example is shown as marked by radioopaque markers 1302 and 1303 on the proximal and distal end of the stimulation region, respectively. As shown, the markers may allow for visualization of the NLR device while inserted into a body region (e.g., using fluoroscopy or the like). For example, radioopaque markers will show up under fluoroscopy darker than the rest of the device.

FIGS. 36A-36B illustrate one variation of a method to help resolve the location of the nerve in such inconclusive situations. These figures illustrate the ability to apply distal and/or proximal tension to the NLR device to probe within the foramen for the spinal nerve.

FIG. 36B shows the NLR device inserted and in the "neutral" position, without applying tension to pull or push either the proximal and distal ends of the device. In this example, The curved region of the neural localization device includes a plurality of stimulation electrodes (e.g., bipolar pairs) arranged along the top and bottom surfaces. The distal end of the NLR device is coupled to a guidewire 3505 (by a releasable guidewire coupler 3504 that is adapted to allow both pushing and pulling). As shown in FIG. 36B, it may be preferable to position the device 3500 such that when viewed in a lateral view under fluoroscopy the proximal marker 3502 is located at the bottom of the curvature of the device body and the distal marker 3503 is located half way between the proximal marker and the distal tip 3504 of the device. Distal marker 3503 is located along dotted line 3506. Furthermore, it may be preferable to position the device 3500 such that the proximal marker 35002 is aligned with the medial aspect of the adjacent pedicle(s).

For example, in FIG. 36A the distal end of the device is pulled (by pulling distally on the guidewire from a position outside of the patient's body) while the proximal handle of the NLR device is held or also pulled. This draws the region of the device including the stimulation dorsally or posteriorly (up in this figure). As shown, distal marker 3505 is raised higher within the spine. 3505 is positioned along dotted line 3506, which is higher than the dotted line in FIG. 36B.

In FIG. 36C the distal end of the device is pushed down by applying force to push the guidewire (and/or distal handle) while either holding the proximal end (or proximal handle) still or anchored, or by pushing down on the proximal handle. Thus, the NLR device may be urged ventrally or anteriorly (down in FIGS. 36A-36C). Energy may be applied to the NLR device while the device is held in any of these positions shown in FIGS. 36A and 36C to determine which side of the NLR device the nerve root is located, in order to confirm that the nerve root is below (anterior/ventral) to the pathway taken by the NLR device and potentially a tissue modification device positioned by the same guidewire.

For example, if the nerve root is located below the NLR device, when the NLR device is pulled up (posteriorly), the device is pulled away from the nerve root, thereby increasing the distance between the top (posterior) side of the device and the nerve root. By increasing the distance between the nerve root and the top (posterior) side of the device, this should increase the threshold stimulation current applied to the top (posterior) surface of the device that will elicit and EMG response, as described in more detail below. Alternatively, when the NLR device is pushed down (anteriorly), the device is pushed toward the nerve root, thereby decreasing the distance between the bottom (anterior) side of the device and the nerve root. By decreasing the distance between the nerve root and the bottom (anterior) side of the device, this should decrease the threshold stimulation current applied to the bottom (anterior) surface of the device that will elicit and EMG response. By increasing the threshold stimulation current applied to the top (posterior) surface and decreasing the threshold stimulation current applied to the bottom (anterior) surface, a greater differential is created between the two threshold values thereby more clearly indicating the location of the nerve with respect to the device.

Figure 37C:
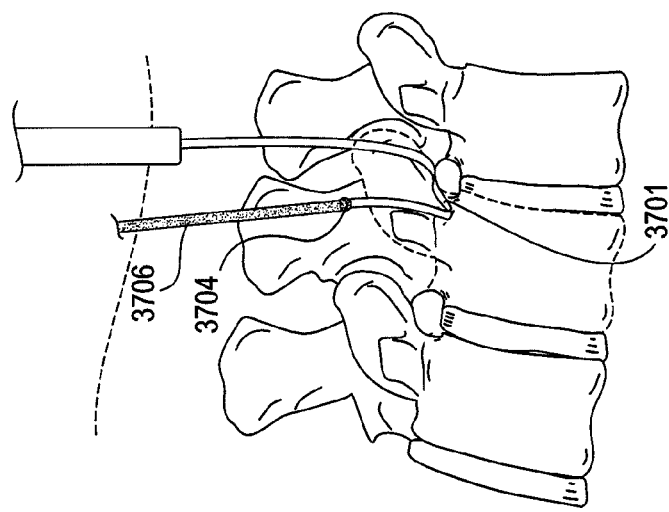
FIGS. 37A-37C illustrate another variation of a method for controlling the configuration and/or position of an NLR device within a spinal foramen, similar to that shown in FIGS. 36A-36C.
Figure 37B:
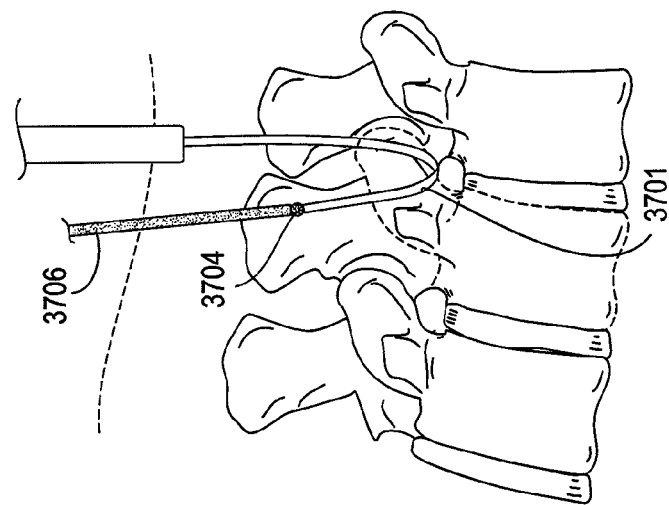
Figure 37A:
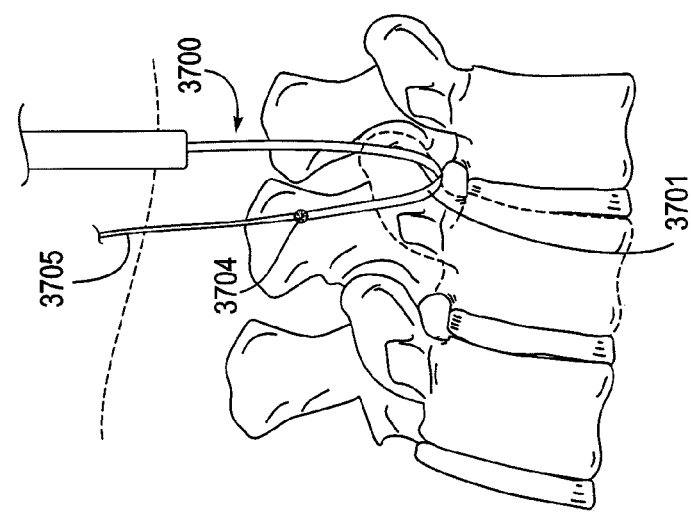

FIGS. 37A-37C illustrate another variation of this technique, in which the NLR is positioned and an external device 3706 (introducer catheter) is used to push down on the distal end of the device as described above with respect to FIG. 36C. These figures also illustrate a method for controlling the configuration of the NLR device, specifically the configuration of the stimulation region of the NLR device. For example, as shown in FIG. 37C, the stimulation region of the NLR device has been pushed down and flattened against the nerve root.

Figure 38:
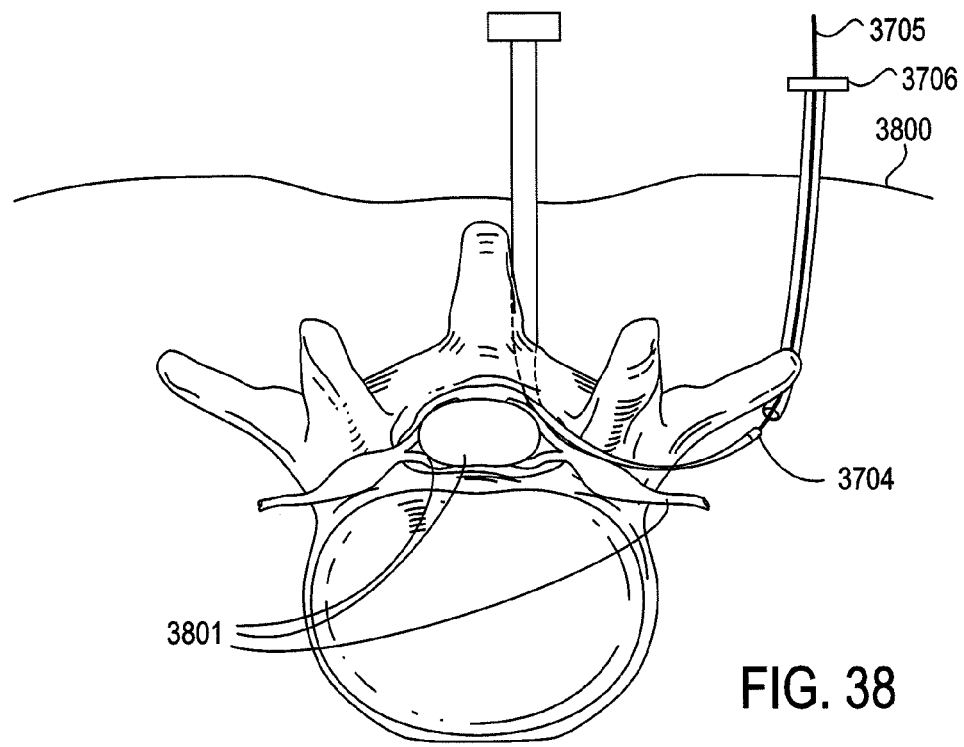
FIG. 38 illustrates the NLR device used in the method illustrated in FIG. 37A-37C.

As shown in FIG. 38, an introducer catheter, such as a stiff tubular member 3706, is advanced over the guidewire 3705 where it exits the patients skin 3800. The tubular member is advanced along the guidewire and into the patient such that the distal end of the catheter is brought into contact with the distal end of the neural localization device. In particular, the distal end of the catheter is brought into contact with the distal end of the elongate body and/or the guidewire coupler 3704, as shown in FIG. 38. The tubular member may be further advanced such that the elongate body of the Ribbon device is moved away from the target tissue and in some instances moved toward a neural structure 3801, as shown in FIG. 38.

Figure 39A:
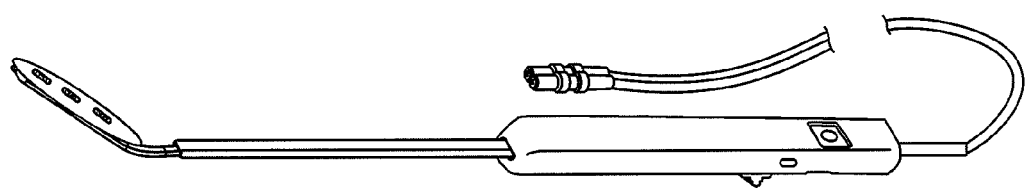
FIGS. 39A and 39B show one variation of an NLR device having an expandable stimulation region.
Figure 39B:
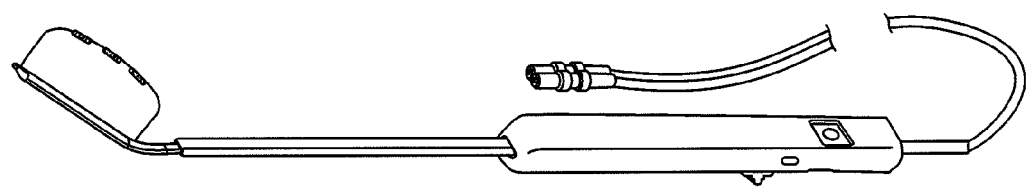

FIGS. 39A and 39B illustrate one variation of an expandable NLR device in which the upper and/or lower surfaces of the device may be expanded outward to help contact a nerve or nerve root during use, as mentioned above. In this example, the upper surface of the device is formed from part of the inflatable member along which the electrodes are positioned. Inflation of the device causes the upper electrodes to move outward from the device. Prior to inflation the device may be positioned and stimulated as described in the variations above.

FIGS. 40-49 illustrate different variations of ribbon-shaped neural localization devices and alternate features from such devices.

Figure 40:
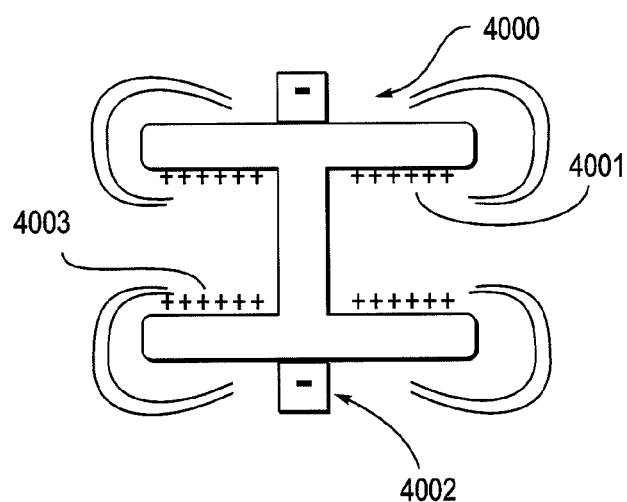
FIG. 40 is one variation of an NLR device having an H-shaped cross-section.

FIG. 40 illustrates one variation of an NLR device having an H-shaped cross-section. In this example, the electrode(s) 4000 on the top outer surface of the device (−) are paired with the (+) electrodes 4001 on the top inner surfaces of the device, while the electrodes 4002 on the bottom outer surface (−) are paired with the electrodes 4003 on the bottom inner surface (+). Applying current to the top bipolar pair(s) will result in a "pseudo monopolar" broadcast, as illustrated, since the broadcast field between the upper outside and inner outside surfaces may resemble that of a monopolar electrode. The broadcast field between the bottom outer and inner electrode pair(s) is also pseudo monopolar.

Figure 41:
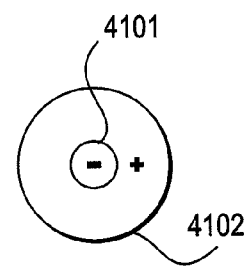
FIG. 41 shows one variation of a patterned pair of electrodes.

FIG. 41 illustrates one variation of a pair of electrodes (bipole pair) for use in any of the variations described herein. This variation includes an inner electrode 4101 that is concentrically surrounded by an outer electrode 4102. As shown in this example, the inner electrode 4101 is negatively (−) charged, while the outer electrode 4102 has a positive charge (+). Alternatively, the polarities may be switched. The outer electrode may completely surround the electrode, or it may only partially surround it. The inner and outer electrode thereby form a bipolar field in which the emission pattern for the bipole may be very tightly regulated, limiting the spread of the field, and preventing stimulation of nerves located at any substantial distance from the pair.

Figure 42:
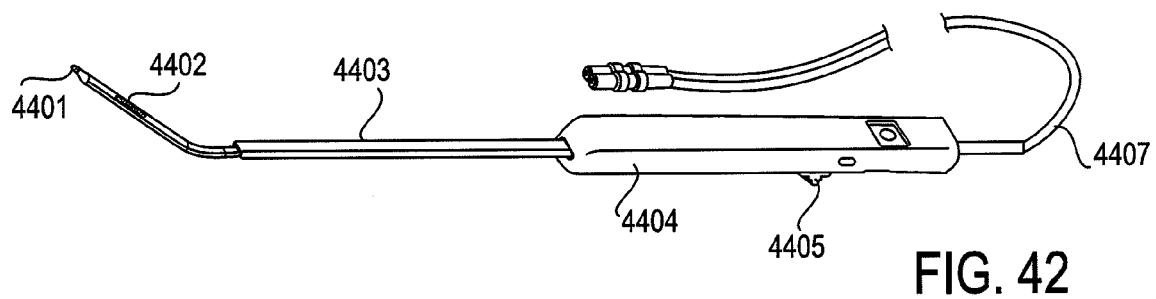
FIG. 42 is one variation of a device such as that shown in FIG. 35 having a pre-biased distal end that is curved.

FIGS. 42-49 show detailed illustrations of various aspects of a single NLR device similar to the device shown in FIG. 35, for example. In this example, the NLR device includes an upper cathode and an upper anode array that each include three proud electrodes, and a lower cathode and lower anode array that also includes three proud electrodes. FIGS. 42 and 44 show a perspective view of this exemplary device, including the flexible ribbon-shaped distal end region (which has a distal guidewire coupling member 4401 and a stimulation region 4402 on each of an upper surface and a lower surface). The device may also include a more stiff region 4403 located proximal o the distal stimulation region. A handle 4404 includes a switch 4405 that can toggle between selection for activation of the electrodes 4406 on the upper surface (shown in detail in FIG. 45) and the electrodes on the lower surface. A cable 4407 connects to a current source (positive and negative leads). FIG. 43 shows a detailed view of the distal end region of this variation, including the guidewire coupler 4401 at the distal end.

In some variations the flexible distal end of the NLR device may be pre-shaped or biased to have set shape, even while the device is flexible. For example, the distal end region of the device may be curved, as illustrated in FIG. 42. This variation, which also includes the distal guidewire coupler 4401, may assist with navigation of the device in the tissue and around target tissue.

Any of the variations described herein may include a guidewire coupler (e.g., at the distal end or distal end region) of the device. In some variations this distal guidewire coupler is configured to connect end-to-end to the proximal end of a guidewire so that the guidewire can be used both to push and to pull the device that is coupled thereto. Thus, the coupler may have a side-entry that releasably secures the proximal end of the guidewire to the distal end of the NLR, as illustrated in FIG. 43. In some variations this device may include a releasable lock to lock guidewire in position.

FIG. 44 shows a slightly enlarged view of the distal end, and FIG. 45 is an even further enlarged view illustrating the proud electrodes extending from the surface (formed by tubing, as shown in FIG. 46 in this example) of the flexible distal end. Although not visible in this illustration the opposite side also includes a mirror-image of the proud electrodes.

FIG. 46, as described above, is a cross-sectional view through the flexible distal end region of the NLR device shown in FIGS. 43-45. In this example, the distal end region includes four channels 4600 for conductors (e.g., wires), two for the upper wires (+/−) and two for the lower wires (+/−), as well as a central channel 4601 hat may be used to hold a substrate. The substrate may modify or determine the stiffness/flexibility of the distal end. The positions (spacing) of the electrodes relative to each other and to the edges of the device may be important for controlling the broadcast field of the upper and lower bipolar fields emitted. For example, spacing the upper and lower electrodes from the edges between the upper and lower surfaces may help prevent wrap-around of the emitted field; wrap-around may result in stimulation of a nerve on the opposite side of the surface that is being stimulated, which may muddle or lead to confusing results. Some amount of wrap-around may be inevitable, but spacing may help minimize this effect.

Figure 47:
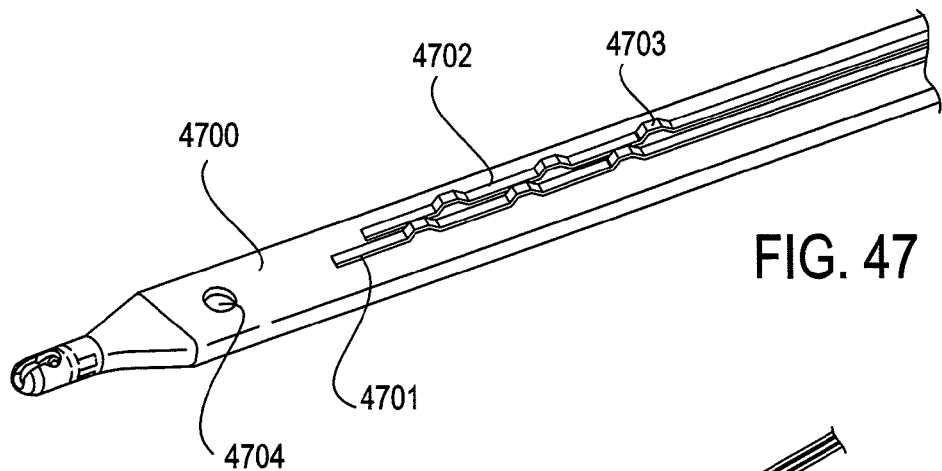
FIG. 47 illustrates another variation of a distal end of an NLR device (without the outer insulator tubing) including a substrate and three pairs of proud electrodes formed of two wires on the visible top surface.

FIG. 47 shows another variation of the distal end region of an NLR device. This variation is shown without the outer (electrically insulating) layer so that the substrate 4700 may be clearly illustrated, as well as the wires 4701 and 4702 forming the electrodes 4703. In this variation the distal end of the device is marked by a hole 4704 through the substrate that may be visible as a lighter region under fluoroscopy.

Figure 48:
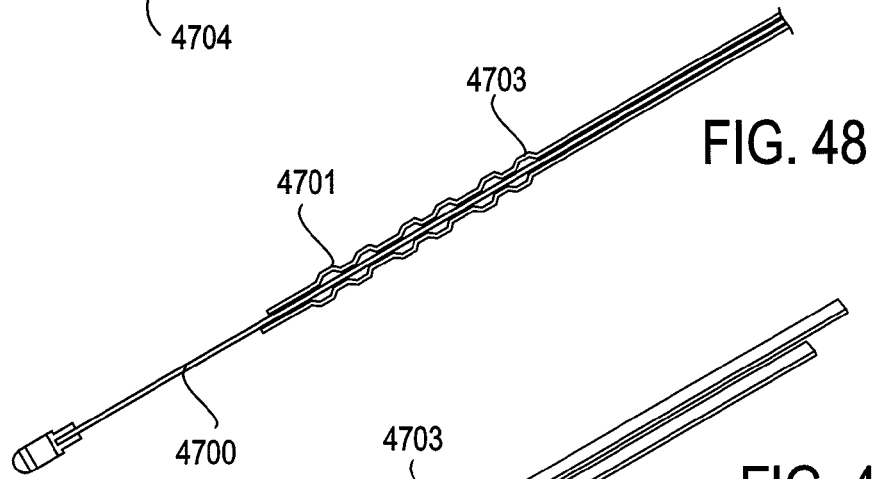
FIG. 48 shows a side-on view of the variation shown in FIG. 47.

FIG. 48 shows a side-on view of the structures illustrated in FIG. 47, and includes both the upper (top) pair of conductors forming the three pairs of proud electrodes on the top surface, and the pair of conductors forming three pairs of proud electrodes on the lower (bottom) surface of conductors forming the five proud electrodes each.

Figure 49:
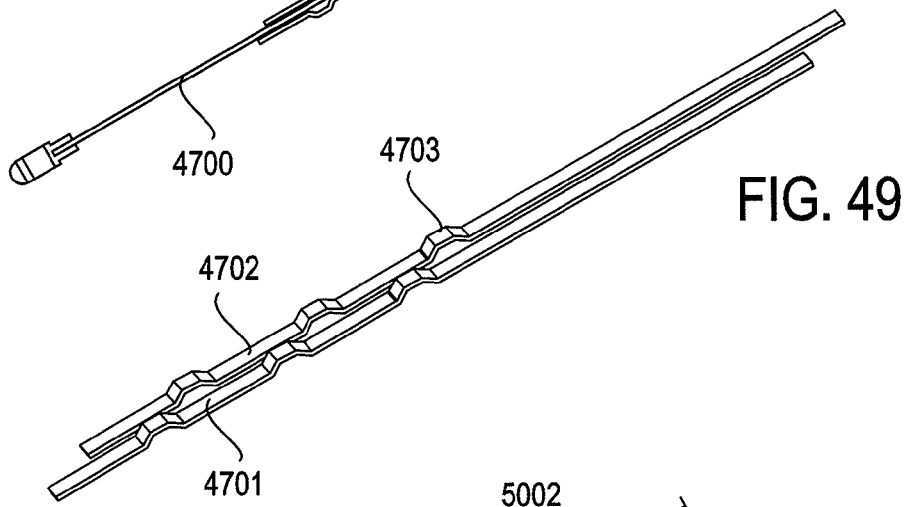
FIG. 49 shows an enlarged view of the conductors forming the three pairs of electrodes on the top surface.

FIG. 49 illustrates just the conductors forming the electrodes for the upper surface, in detail.

Figure 50:
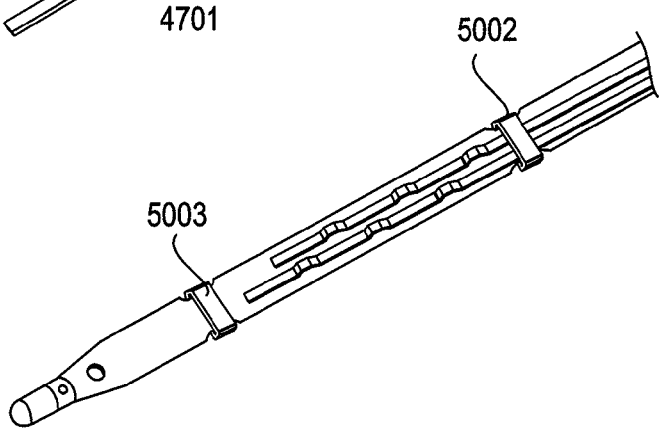
FIG. 50 is another view of a distal end of an NLR device similar to that shown in FIG. 47, also including a pair of ring coil markers on either side of the stimulation region.

Markers 5002 and 5003 may be present at the proximal and distal edges of the conductive region, as illustrated in the partial view shown in FIG. 50. In this example, a pair of markers (configured as ring coils are radioopaque markers positioned on either side of the conductive region, distally and proximally. The markers are formed of platinum iridium, although any appropriate radioopaque (e.g., electrodense) material may be used. In some variations, markers may be indicated by the absence of an electrodense material or region. For example, the marker may be a hole, gap, etc. in the device.

In some embodiments, the electrodes may be configured to apply and receive an electrical signal to and from the target tissue. In this embodiment, the signal may be a non-stimulating electrical output and may characterize the tissue (target tissue and non-target tissue) using electrical bio-impedance. Electrical bio-impedance is the response of living tissues to externally applied electrical current. Bio-impedance measurements are carried out while "sweeping" a frequency of the applied electrical signal. During these measurements, the electrodes may be static or may propagate through the body. Alternatively, the device may include a series of electrodes which are activated sequentially along the length of the device. The measured bio-impedance components (resistance, capacitance, phase, etc.) are frequency-dependent thus characterizing the tissue or tissue(s) interacting with the device and electrodes. Real-time analysis of the measured parameters enables determining what type of tissue (for example, whether a nerve) is nearby a device or portion of a device.

The impedance of the tissue may be calculated at different frequencies and/or tissue position (e.g. depth) such that the body tissue type may be identified. In a first embodiment, the tissue position may be varied by moving a single electrode pair through the tissue. Alternatively, the device may be positioned within the tissue and then a series of electrode pairs may be activated along a length of the device, each electrode being at a different position along the length of the device. The measured impedance may be continuously compared with impedance data (e.g. known impedance values for blood, muscle, nerve, fat, ligament, etc.).

Figure 51:
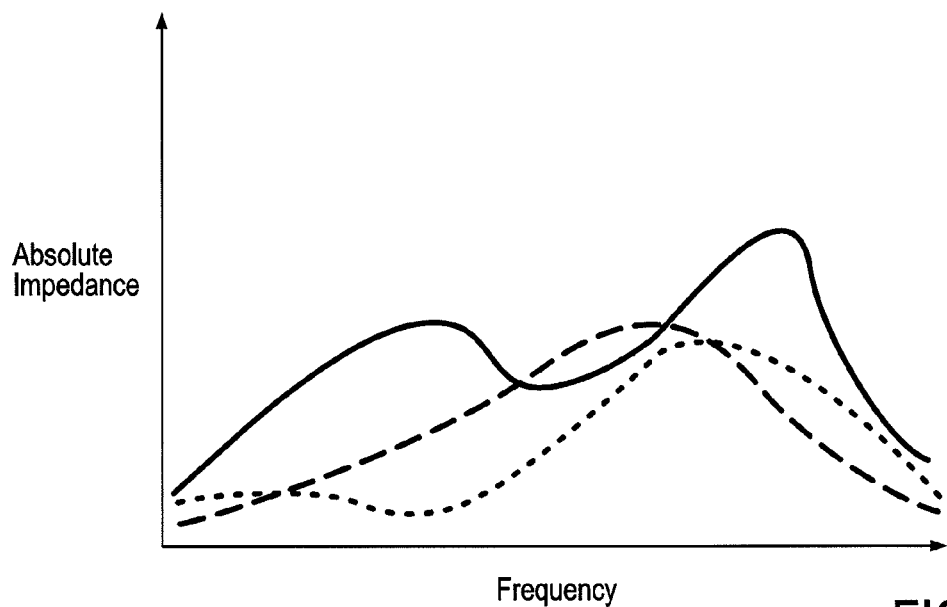
FIGS. 51-53 graphically illustrate the principles of a method of the neural localization device.

For example, FIG. 51 illustrates simulation data for three different tissue impedance profiles as a function of operating frequency, for three different tissues. This is a general representation of the frequency dependence of the impedance measured from different tissues. The complex impedance parts can be measured (capacitance/resistance), adding the phase information.

To characterize all the tissues in the immediate vicinity of the device, a theoretical model is calculated taking into account the general properties of each tissue such as the tissue thickness, geometry, density and the electric constants characteristic of the tissue, and the tissue dielectric properties such as the resistivity and the capacitance of the tissue. The general tissue properties might be found in the literature, while the tissue dielectric properties are measured as a function of an electromagnetic frequency. Data indicative of the expected values measured by the tissue characterization system is therefore calculated. The theoretical model of the tissue structure enables to predict the current behavior on the probing portion.

Figure 52:
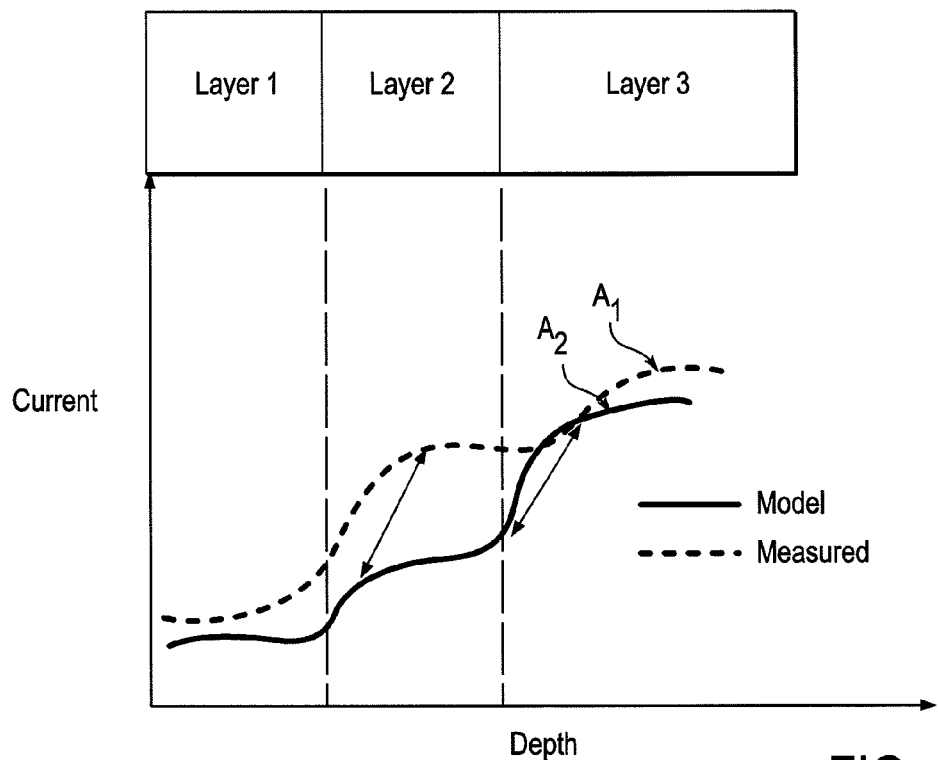

The measurements are continuously compared to the modeled data to determine the type of tissue adjacent to the device. For example, FIG. 52, illustrates the transition between two types of tissue, Layer 1/Layer 2 and Layer 2/Layer 3, having different impedance characteristics illustrated by a change in the impedance measurement as a function of depth within a body portion. Curve A1 represents the measured current as a function of depth through three different layers (different tissue types). Curve A2 represents the theoretical calculated current as a function of depth through the respectively three different layers. Arrows between the curves show the correspondence between the theoretical and the measured data.

Figure 53:
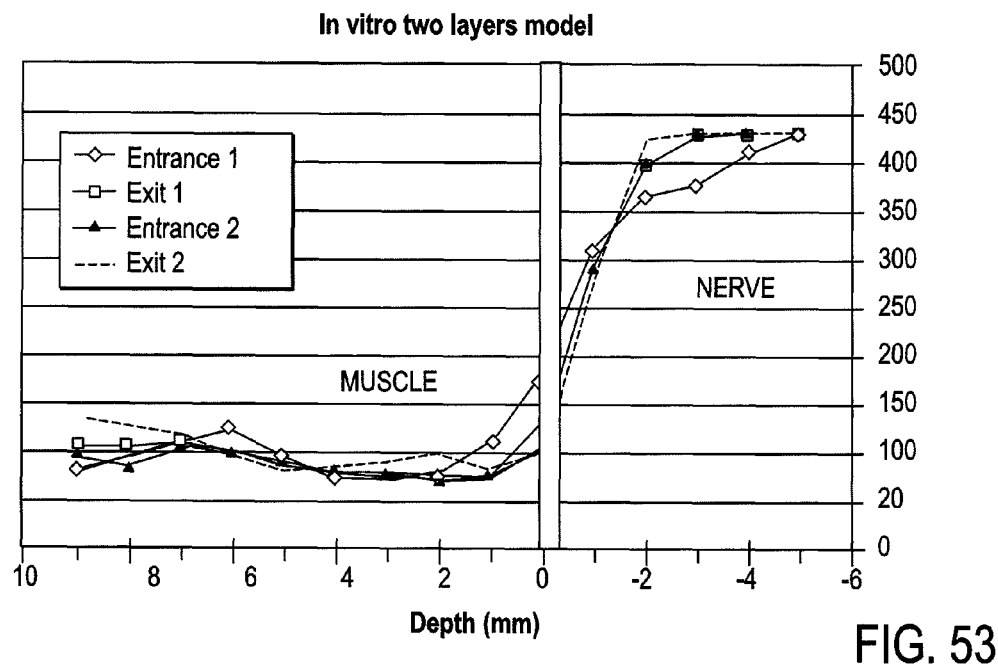

FIG. 53 represents hypothetical impedance measurements for a muscle-nerve bi-layer along a length of a device. The muscle-nerve transition point is marked as the zero (0) point in the graph. The impedance measurements reveal a significant difference between the muscle and nerve impedance. In this example, the muscle impedance may be in the range of about 70-130 ohm, while the nerve impedance may be in the range of about 350-430 ohm.

Figure 54:
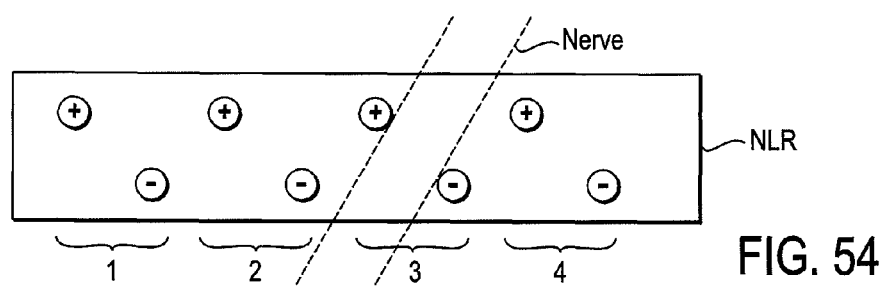
FIGS. 54-56B illustrate various embodiments of an NLR device and operation of various devices.
Figure 55:
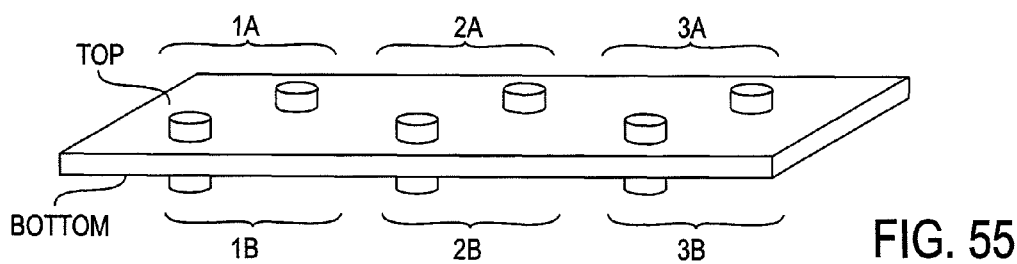

As shown in FIG. 54, the NLR device may include a plurality of electrode pairs (labeled 1-4) along the length of the device. As shown in FIG. 55, the NLR device includes a plurality of electrode pairs (labeled 1-3) along the length of the device on both the top surface of the device and the bottom surface of the device. As shown in FIG. 54, once the NLR device is positioned within a patient, a nerve may be adjacent to a portion of the device. In this example, the nerve is in the closest proximity to the electrode pair labeled 3. One the device is positioned, the device may activate a single electrode pair at a time. While each pair is activated, the impedance or other characteristic of the adjacent tissue may be indicated and/or recorded. For example, the electrode pairs 1, 2, and 4 may be adjacent to blood or muscle or fat and may indicate at least a first impedance measurement, while electrode pair 3 may be adjacent to the nerve and may indicate a second, distinct impedance measurement. For example, as shown in FIG. 53, depths 0 to −6 mm may correspond to electrode pair 3 (indicating nerve) while depths 10 to 0 mm may correspond to electrode pairs 1 and 2 (indicating muscle). As shown in FIG. 55, each of the electrode pairs along the top surface may be activated and then each of the electrode pairs along the bottom surface may be activated. Alternatively, the top and bottom surfaces may be alternated or the electrodes may be activated in any other suitable order. In some embodiments, all electrode pairs may be activated simultaneously such that the device is "searching" for the nerve. The device may then report back the reading from the electrode pair that indicates it is adjacent to the nerve. Based on which electrode pair indicates that it is adjacent to nerve, the user will be able to identify if the nerve is adjacent to the top surface (indicating it is not safe to proceed with tissue modification, for example) or the bottom surface (indicating it is safe to proceed with tissue modification, for example).

Figure 56A:
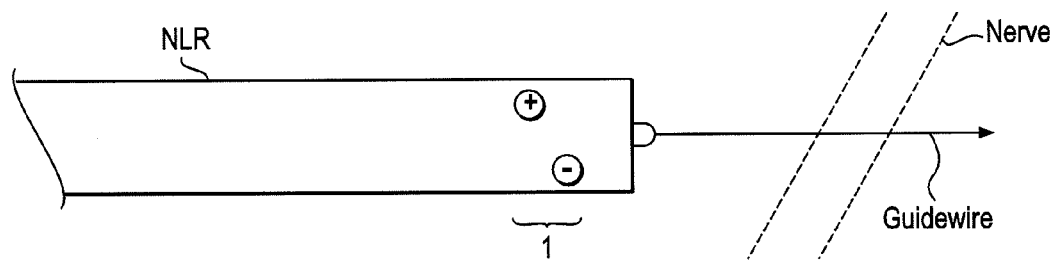
Figure 56B:
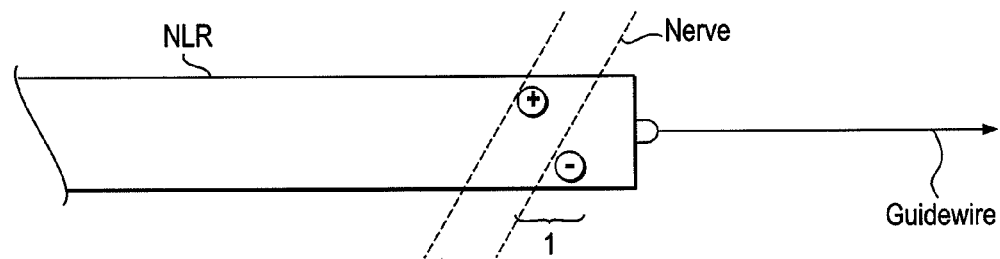

As shown in FIGS. 56A and 56B, rather than having multiple electrode pairs along the length of the device, the NLR device may include a single electrode pair 1. The electrode pair may be activated as the NLR device is pulled by the guidewire into position. For example, as shown in FIG. 56A, the NLR device and electrode pair are not adjacent to a nerve. Once again, as shown in FIG. 53, this may correspond to depths 10 to 0 mm. As shown in FIG. 56B, the NLR device has been pulled into position such that the NLR device and electrode pair are adjacent to a nerve. As shown in FIG. 53, this may correspond to depths 0 to −6 mm. In this embodiment, the NLR device may also includes an electrode pair (not shown) on the bottom surface of the device. This electrode pair may also be activated while the top electrode pair is activated or alternatively, the top and bottom pairs may be alternated as the device is advanced into position.

Figure 57:
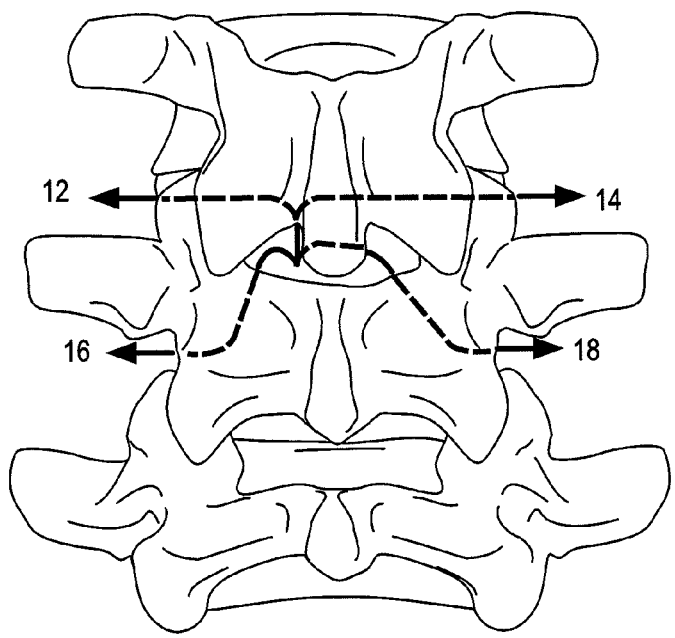
FIG. 57 is a posterior view of the spine indicating decompression paths at disk level and along the nerve root.

Also described herein is a method of increasing foraminal height by removing primarily boney tissue on the inferior edge of a pedicle, cephalad to a targeted nerve root. The devices, systems and methods may be configured to decompress spinal nerve roots on the unilateral or contralateral side from an access point. A probe or guide may be introduced into the spinal epidural space (or along or just within the ligamentum flavum) at an appropriate spinal level using image guidance and/or tracking (e.g., electromagnetic tracking). Introduction may be either via percutaneous puncture or open laminotomy. As shown in FIG. 57, a tissue modification device may be used to decompress an ipsilateral or contralateral proximal nerve (in a lateral recess). A guide or probe may be deployed immediately cephalad to the caudal segment pedicle on the appropriate side (e.g., location 10). This access point can be confirmed radiographically. If neural structures adjacent to the guide cannot be directly visualized, the relationship of these structures to the guide or tissue modification devices can be determined as described above.

Figure 58:
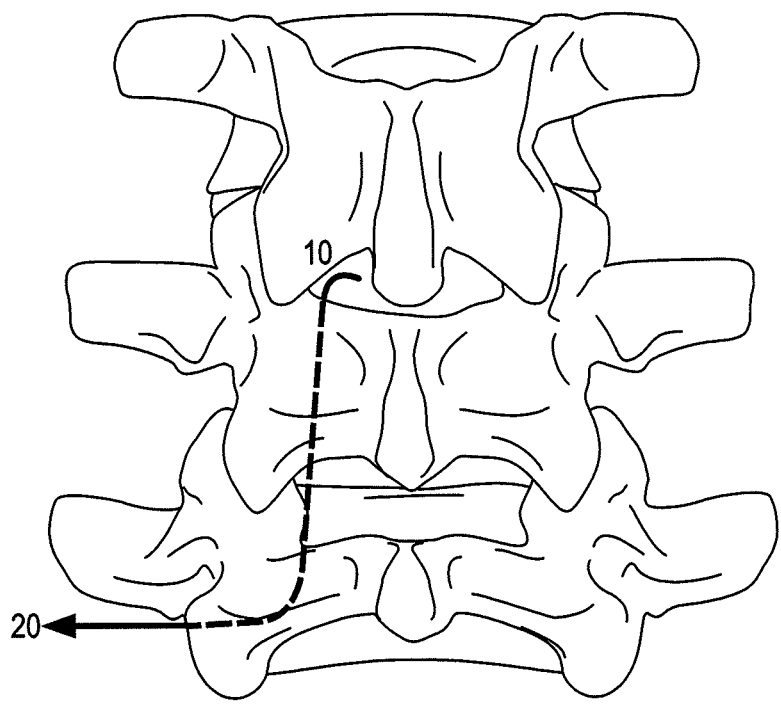
FIG. 58 is a posterior view of the spine indicating a decompression path for adjacent level lateral recess decompression.

As shown in FIG. 57, the guidewire may be threaded along a path from location 10 to where it exits through the foramen, as shown by at least one of arrows 12 (for ipsilateral decompression of the nerve root origin at the disk level) and 14 (for contralateral decompression of the nerve root origin at the disk level). Alternatively, as shown in FIG. 7, the guidewire may be threaded along a path from location 10 to where it exits through the foramen, as shown by at least one of arrows 16 (for ipsilateral decompression along the nerve root) and 18 (for contralateral decompression along the nerve root). In some embodiments, the probe/guide is removed once the guidewire has been positioned. As shown in FIG. 58, the devices described herein can used to decompress the ipsilateral (arrow 20) or contralateral (not shown), or both, regions adjacent the level proximal to the nerve root (lateral recess). A guide may be deployed in the same access point (location 10) as described above. As shown in FIG. 58, the guidewire can then be threaded along a path from location 10 to where it exits through the foramen, as shown by arrow 20 (for ipsilateral decompression of the adjacent nerve root origin).

Figure 59:
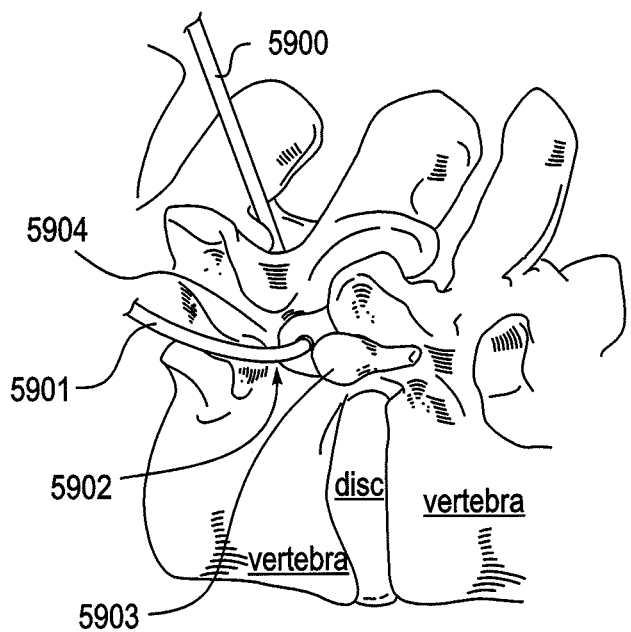
FIGS. 59-61 illustrate a method of increasing foraminal height.
Figure 60:
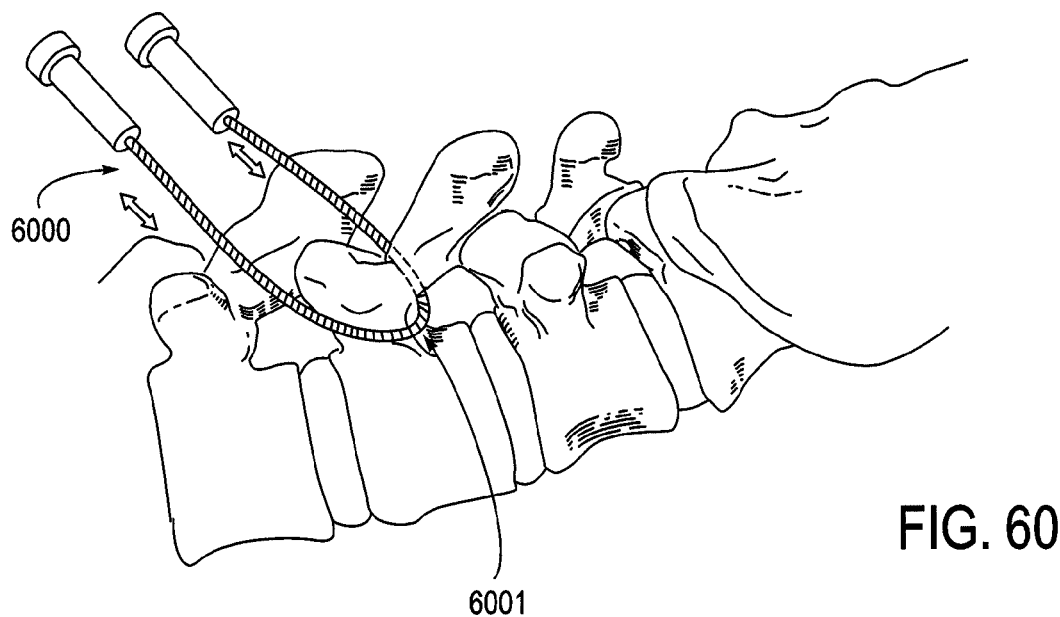

The guidewire may include a wire exchange tip on its proximal end, as described in more detail above. A flexible tissue modification device is attached to the proximal wire exchange tip, and a distal handle may be secured to guidewire at the distal wire tip. The device can then be introduced into the epidural space and then into the lateral recess by careful upward force applied to the distal handle. In some embodiments, the device is pulled by the guidewire on the path through the spinal anatomy. As described above, suitable paths include paths shown by arrows 12, 14, 16, 18, and/or 20 to decompress the nerve root origin at disk level and/or along the nerve root, respectively. As shown in FIG. 59, a probe 5900 may be inserted and a guidember 5901 deployed along a path through the spinal anatomy such that the tissue modification surface may be positioned adjacent to target bony tissue 5902 on the inferior edge of a pedicle 5904, cephalad to a targeted nerve root 5903 as described below. As shown in FIG. 60, a tissue modification device 6000 may be pulled by a guidewire (not shown) on the path through the spinal anatomy as shown in FIG. 59, such that the tissue modification surface is adjacent to the target bony tissue. The probe/guide may be reinserted to decompress the ipsilateral or contralateral distal (foraminal) portion of the nerve root, so that the same (or a different) tissue modification device may be used to decompress another region of the spine (or nerve root) using the same access or entry site.

Figure 61:
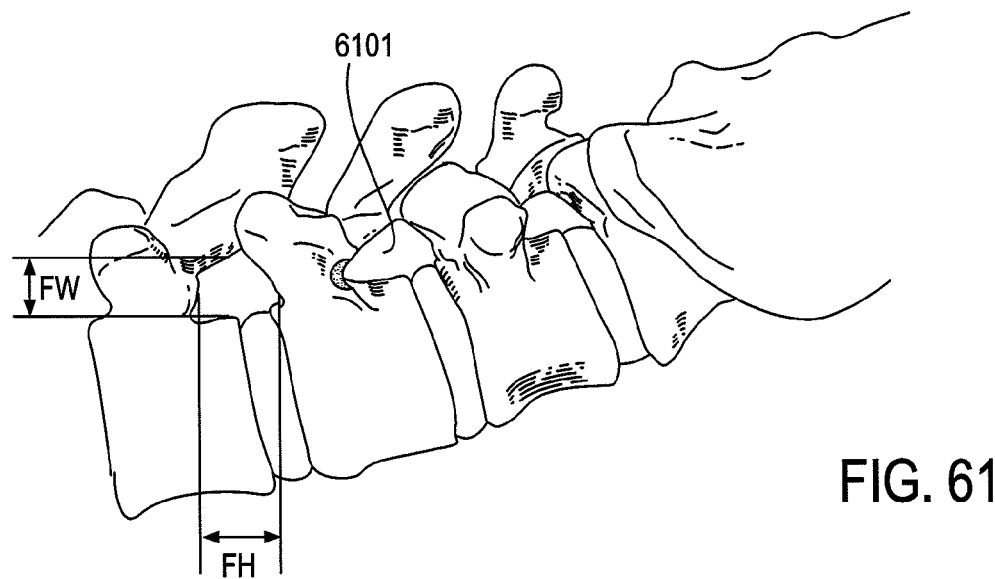

Once the device is in place as confirmed visually or radiographically, bimanual reciprocating strokes may be utilized to decompress dorsal impinging bone or soft tissue at the nerve root origin. As shown in FIGS. 59-61, bimanual reciprocating strokes may be utilized to increase foraminal height by removing primarily boney tissue on the inferior edge of a pedicle, cephalad to a targeted nerve root. As shown in FIG. 61, foraminal height (FH) may be defined as the distance between the inferior edge of the cephalad pedical and the superior edge of the caudal pedicle. Foraminal width (FW) may be defined as the distance from the posterior aspect of the disc or vertebra to the anterior aspect of the lamina and/or facet joint. The target boney tissue 6001 may be located on the inferior edge of the cephalad pedicle. In the example shown in FIG. 61, the targeted nerve root is exciting through foramen 6101.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of positioning a neural localization device to determine if a nerve is nearby, the method comprising:
passing a neural localization device along a first pathway, the neural localization device having a flexible ribbon-shaped body having a first set of electrodes on one face of the ribbon-shaped body and a second set of electrodes on an opposite face of the ribbon-shaped body;
energizing a first stimulation region of the neural localization device to emit a stimulation field in a first stimulation direction from the neural localization device;
determining a threshold stimulation location along the pathway, wherein the threshold stimulation location corresponds to a position along the pathway having the lowest stimulation level emitted in the first stimulation direction that evokes a response from a target neural tissue;
positioning the neural localization device at the threshold stimulation location;
determining a threshold stimulation level in a second stimulation direction from the neural localization device while the neural localization device is at the threshold stimulation location; and
comparing the stimulation level emitted in the first stimulation direction at the threshold stimulation location to the threshold stimulation level in the second stimulation direction to determine if the target neural tissue is in the first stimulation direction or in the second stimulation direction.

2. The method of claim 1, further comprising coupling the neural localization device to a guidewire.

3. The method of claim 1, wherein passing the neural localization device along the first pathway comprises passing a guidewire along the first pathway before passing the neural localization device.

4. The method of claim 1, wherein energizing the first stimulation region comprises applying stimulation by ramping a current from 0 mA to less than 100 mA.

5. The method of claim 1, wherein energizing the first stimulation region comprises repeatedly ramping a current between 0 mA and less than 100 mA.

6. The method of claim 1, wherein determining a threshold stimulation location along the pathway comprises moving the neural localization device forward and backward along the pathway while emitting the stimulation field in the first stimulation direction.

7. The method of claim 1, wherein determining a threshold stimulation location along the pathway comprises determining the minimum stimulation emitted in the first stimulation direction that evokes a response from a target neural tissue.

8. The method of claim 1, wherein determining the threshold stimulation level in the second stimulation direction from the neural localization device comprises increasing the current applied from the second stimulation direction until a response is detected.

9. The method of claim 1, wherein comparing the stimulation level emitted in the first stimulation direction to the threshold stimulation level in the second stimulation direction comprises comparing the minimum stimulation level required to evoke a response that is emitted in the first stimulation direction at the threshold stimulation direction to the threshold stimulation level emitted in the second stimulation direction.

10. A method of positioning a neural localization device to determine a location of a nerve relative to a device, the method comprising:

passing a distal end of a neural localization device in a first direction;

energizing a first stimulation region of the neural localization device to emit a stimulation field in a first stimulation direction from the neural localization device and evoking a response from a target neural tissue, wherein emitting the stimulation field includes ramping a current between a plurality of stimulation levels;

determining, at a first location, a minimum stimulation level that evokes the response from the target neural tissue from the first stimulation region;

energizing a second stimulation region of the neural localization device to emit a stimulation field in a second stimulation direction from the neural localization device while the neural localization device is in the first location;

determining, at the first location, a minimum stimulation level that evokes a response from the target neural tissue from the second stimulation region;

comparing the minimum stimulation level from the first stimulation region to the minimum stimulation level from the second stimulation region to determine if the target neural tissue is in the first stimulation direction or in the second stimulation direction;

moving the first stimulation region and the second stimulation region in the first stimulation direction to a second location;

energizing the first stimulation region at the second location to determine a second minimum stimulation level that evokes a response from the target neural tissue from the first stimulation region;

energizing the second stimulation region at the second location to determine a second minimum stimulation level that evokes a response from the target neural tissue from the second stimulation region; and comparing the second minimum stimulation level from the first stimulation region to the second minimum stimulation level from the second stimulation region to determine if the target neural tissue is in the first stimulation direction or in the second stimulation direction.

11. The method of claim 10, wherein the first stimulation region and the second stimulation region are moved in the first stimulation direction to a second location when a ratio of the minimum stimulation level from the first stimulation region to the minimum stimulation level from the second stimulation region is within a predetermined range.

12. The method of claim 10, wherein the first stimulation region and the second stimulation region are moved in the first stimulation direction to a second location when the step of comparing the minimum stimulation level from the first stimulation region to the minimum stimulation level from the second stimulation region to determine if the target neural tissue is in the first stimulation direction or in the second stimulation direction is inconclusive.

* * * * *